United States Patent
Weinstein et al.

(10) Patent No.: US 9,593,113 B2
(45) Date of Patent: Mar. 14, 2017

(54) IMIDE AND ACYLUREA DERIVATIVES AS MODULATORS OF THE GLUCOCORTICOID RECEPTOR

(71) Applicant: BRISTOL-MYERS SQUIBB COMPANY, Princeton, NJ (US)

(72) Inventors: David S. Weinstein, East Windsor, NJ (US); Hua Gong, King Of Prussia, PA (US); Michael G Yang, Narbeth, PA (US); Zili Xiao, East Windsor, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 14/911,485

(22) PCT Filed: Aug. 21, 2014

(86) PCT No.: PCT/US2014/052014
§ 371 (c)(1),
(2) Date: Feb. 11, 2016

(87) PCT Pub. No.: WO2015/027021
PCT Pub. Date: Feb. 26, 2015

(65) Prior Publication Data
US 2016/0185776 A1    Jun. 30, 2016

Related U.S. Application Data

(60) Provisional application No. 61/868,822, filed on Aug. 22, 2013.

(51) Int. Cl.
| | | |
|---|---|---|
| *C07D 471/04* | (2006.01) | |
| *C07D 311/90* | (2006.01) | |
| *C07D 311/80* | (2006.01) | |
| *C07D 491/04* | (2006.01) | |

(52) U.S. Cl.
CPC .......... *C07D 471/04* (2013.01); *C07D 311/80* (2013.01); *C07D 311/90* (2013.01); *C07D 491/04* (2013.01)

(58) Field of Classification Search
None
See application file for complete search history.

(56) References Cited

U.S. PATENT DOCUMENTS

| | | | |
|---|---|---|---|
| 2,746,992 A | 5/1956 | Goldberg et al. | |
| 5,478,853 A | 12/1995 | Regnier et al. | |
| 5,506,245 A | 4/1996 | Regnier et al. | |
| 5,594,001 A | 1/1997 | Teleha et al. | |
| 5,750,528 A | 5/1998 | Brown et al. | |
| 8,034,940 B2 * | 10/2011 | Weinstein ............ | C07D 277/46 546/80 |

FOREIGN PATENT DOCUMENTS

| | | |
|---|---|---|
| AT | 186643 B | 8/1956 |
| WO | WO 94/24131 A1 | 10/1994 |
| WO | WO 99/00535 A1 | 1/1999 |
| WO | WO 01/09137 A1 | 2/2001 |
| WO | WO 2004/054504 A2 | 7/2004 |
| WO | WO 2007/085558 A1 | 8/2007 |
| WO | WO 2008/021926 A2 | 2/2008 |
| WO | WO 2009/108525 A2 | 9/2009 |
| WO | WO 2011/115928 A1 | 9/2011 |
| WO | WO 2013/044092 A1 | 3/2013 |

OTHER PUBLICATIONS

CAS Registry No. 1350027-85-8, Entered STN: Dec. 7, 2011.
CAS Registry No. 1349707-09-0, Entered STN: Dec. 6, 2011.
CAS Registry No. 1349534-78-6, Entered STN: Dec. 6, 2011.
CAS Registry No. 1349465-96-8, Entered STN: Dec. 6, 2011.
CAS Registry No. 1349150-45-3, Entered STN: Dec. 5, 2011.
CAS Registry No. 1348306-04-6, Entered STN: Dec. 4, 2011.
CAS Registry No. 1348033-49-7, Entered STN: Dec. 4, 2011.
CAS Registry No. 1347914-89-9, Entered STN: Dec. 4, 2011.
CAS Registry No. 1347835-92-0, Entered STN: Dec. 4, 2011.
CAS Registry No. 1347721-70-3, Entered STN: Dec. 2, 2011.
CAS Registry No. 1347521-79-2, Entered STN: Dec. 2, 2011.
CAS Registry No. 1008119-40-1, Entered STN: Mar. 16, 2008.
CAS Registry No. 1008119-36-5, Entered STN: Mar. 16, 2008.
CAS Registry No. 1008119-34-3, Entered STN: Mar. 16, 2008.
CAS Registry No. 1008119-32-1, Entered STN: Mar. 16, 2008.
CAS Registry No. 1008119-27-4, Entered STN: Mar. 16, 2008.
CAS Registry No. 1008118-50-0, Entered STN: Mar. 16, 2008.
CAS Registry No. 1008117-95-0, Entered STN: Mar. 16, 2008.
CAS Registry No. 1008117-93-8, Entered STN: Mar. 16, 2008.
CAS Registry No. 1008117-90-5, Entered STN: Mar. 16, 2008.
CAS Registry No. 1008117-79-0, Entered STN: Mar. 16, 2008.
CAS Registry No. 1008117-77-8, Entered STN: Mar. 16, 2008.
CAS Registry No. 1008117-64-3, Entered STN: Mar. 16, 2008.
CAS Registry No. 1008117-62-1, Entered STN: Mar. 16, 2008.
CAS Registry No. 1008117-54-1, Entered STN: Mar. 16, 2008.
CAS Registry No. 1008117-52-9, Entered STN: Mar. 14, 2008.
CAS Registry No. 1008117-50-7, Entered STN: Mar. 14, 2008.

(Continued)

*Primary Examiner* — Brian J Davis
(74) *Attorney, Agent, or Firm* — Hong Liu

(57) ABSTRACT

Novel non-steroidal compounds are provided which are useful in treating diseases or disorders associated with modulation of the glucocorticoid receptor, AP-1, and/or NF-$_K$B activity, including metabolic and inflammatory and immune diseases or disorders, having the structure of formula (I): an enantiomer, diastereomer, or tautomer thereof, or a pharmaceutically-acceptable salt thereof, in which the variables are as defined in the specification.

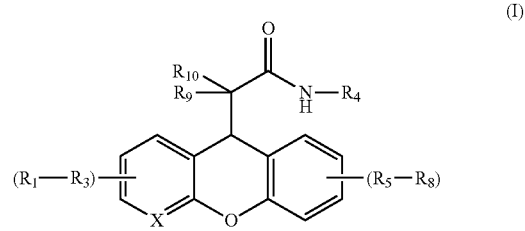

15 Claims, No Drawings

(56) References Cited

OTHER PUBLICATIONS

CAS Registry No. 1008117-47-2, Entered STN: Mar. 14, 2008.
CAS Registry No. 1008117-44-9, Entered STN: Mar. 14, 2008.
CAS Registry No. 1008117-41-6, Entered STN: Mar. 14, 2008.
CAS Registry No. 1008117-39-2, Entered STN: Mar. 14, 2008.
CAS Registry No. 1008117-37-0, Entered STN: Mar. 14, 2008.
CAS Registry No. 1008117-35-8, Entered STN: Mar. 14, 2008.
CAS Registry No. 1008117-33-6, Entered STN: Mar. 14, 2008.
Evdokimoff et al., "9-Substituted xanthene derivatives, III", Annali di Chimica (Rome, Italy) vol. 57(12), pp. 1520-1532 (1967).
Gong, Hua et al., "Discovery of acylurea isosteres of 2-acylaminothiadiazole in the azaxanthene series of glucocorticoid receptor agonists", Bioorganic & Medicinal Chemistry Letters, vol. 24, pp. 3268-3273 (2014).
Villani, Frank et al., "Benzopyranopyridine Derivatives.1. Aminoalkyl Derivatives of the Azaxanthenes as Bronchodilating Agents", Journal of Medicinal Chemistry, vol. 18(1), pp. 1-8 (1975).
Weinstein, David et al., Azaxanthene Based Selective Glucocorticoid Receptor Modulators: Design, Synthesis, and Pharmacological Evaluation of (S)-4(5-(14(1,3,4-Thiadiazol-2-yl)amino)-2-methyl-1-oxopropan-2-yl)-5H-chromeno[2,3-b]pyridine-2-yl)-2-fluoro-N,N-dimethylbenzamide (BMS-776532) and Its Methylene Homologue (BMS-791826), Journal of Medicinal Chemistry, vol. 54, pp. 7318-73333 (2011).

* cited by examiner

IMIDE AND ACYLUREA DERIVATIVES AS MODULATORS OF THE GLUCOCORTICOID RECEPTOR

CROSS REFERENCE TO RELATED APPLICATIONS

This application is entitled to priority pursuant to 35 U.S.C. §119(e) to U.S. provisional patent application No. 61/868,822, filed on Aug. 22, 2013, which is incorporated herein in its entirety.

FIELD OF THE INVENTION

The present invention relates to new non-steroidal compounds which are effective modulators of the glucocorticoid receptor, AP-1, and/or NF-κB activity and thus are useful in treating diseases or disorders including metabolic and inflammatory or immune associated diseases or disorders. The present invention also provides compositions thereof and methods for using such compounds and compositions to treat these and related diseases or disorders.

BACKGROUND OF THE INVENTION

The transcription factors NF-κB and AP-1 are involved in regulating the expression of a number of genes involved in mediating inflammatory and immune responses. NF-κB regulates the transcription of genes including TNF-α, IL-1, IL-2, IL-6, adhesion molecules (such as E-selectin) and chemokines (such as Rantes), among others. AP-1 regulates the production of the cytokines TNF-α, IL-1, IL-2, as well as, matrix metalloproteases. Drug therapies targeting TNF-α, a gene whose expression is regulated by both NF-κB and AP-1, have been shown to be highly efficacious in several inflammatory human diseases including rheumatoid arthritis and Crohn's disease. Accordingly, NF-κB and AP-1 play key roles in the initiation and perpetuation of inflammatory and immunological disorders. See Baldwin, A. S., *J. Clin. Invest.*, 107:3 (2001); Firestein, G. S. et al., *Arthritis and Rheumatism*, 42:609 (1999); and Peltz, G., *Curr. Opin. Biotech.*, 8:467 (1997).

There are many signaling molecules (kinases and phosphatases) upstream of AP-1 and NF-κB which are potential therapeutic drug targets. The kinase JNK plays an essential role in regulating the phosphorylation and subsequent activation of c-jun, one of the subunits which constitute the AP-1 complex (fos/c-jun). Compounds which inhibit JNK have been shown to be efficacious in animal models of inflammatory disease. See Manning, A. M. et al., *Nature Rev. Drug Disc.*, 2:554 (2003). A kinase critical to the activation of NF-κB is the IκB kinase (IKK). This kinase plays a key role in the phosphorylation of IκB. Once IκB is phosphorylated it undergoes degradation leading to the release of NF-κB which can translocate into the nucleus and activate the transcription of the genes described above. An inhibitor of IKK, BMS-345541, has been shown to be efficacious in animal models of inflammatory disease. See Burke, J. R., *Curr. Opin. Drug Discov. Devel.*, 6(5):720-728 (September 2003).

In addition to inhibiting signaling cascades involved in the activation of NF-κB and AP-1, the glucocorticoid receptor has been shown to inhibit the activity of NF-κB and AP-1 via direct physical interactions. The glucocorticoid receptor (GR) is a member of the nuclear hormone receptor family of transcription factors, and a member of the steroid hormone family of transcription factors. Affinity labeling of the glucocorticoid receptor protein allowed the production of antibodies against the receptor which facilitated cloning the glucocorticoid receptors. For results in humans see Weinberger et al., *Science*, 228:740-742 (1985); Weinberger et al., *Nature*, 318:670-672 (1986) and for results in rats see Miesfeld, R., *Nature*, 312:779-781 (1985).

Glucocorticoids which interact with GR have been used for over 50 years to treat inflammatory diseases. It has been clearly shown that glucocorticoids exert their anti-inflammatory activity via the inhibition by GR of the transcription factors NF-κB and AP-1. This inhibition is termed transrepression. It has been shown that the primary mechanism for inhibition of these transcription factors by GR is via a direct physical interaction. This interaction alters the transcription factor complex and inhibits the ability of NF-κB and AP-1 to stimulate transcription. See Jonat, C. et al., *Cell*, 62:1189 (1990); Yang-Yen, H. F. et al., *Cell*, 62:1205 (1990); Diamond, M. I. et al., *Science*, 249:1266 (1990); and Caldenhoven, E. et al., *Mol. Endocrinol.*, 9:401 (1995). Other mechanisms such as sequestration of co-activators by GR have also been proposed. See Kamei, Y. et al., *Cell*, 85:403 (1996); and Chakravarti, D. et al., *Nature*, 383:99 (1996).

In addition to causing transrepression, the interaction of a glucocorticoid with GR can cause GR to induce transcription of certain genes. This induction of transcription is termed transactivation. Transactivation requires dimerization of GR and binding to a glucocorticoid response element (GRE).

Recent studies using a transgenic GR dimerization defective mouse which cannot bind DNA have shown that the transactivation (DNA binding) activities of GR could be separated from the transrepressive (non-DNA binding) effect of GR. These studies also indicate that many of the side effects of glucocorticoid therapy are due to the ability of GR to induce transcription of various genes involved in metabolism, whereas, transrepression, which does not require DNA binding leads to suppression of inflammation. See Reichardt, H. M. et al., *Cell*, 93:531 (1998) and Reichardt, H. M., *EMBO J.*, 20:7168 (2001).

Compounds that modulate AP-1 and NF-κB activity would be useful in the treatment of inflammatory and immune diseases and disorders such as osteoarthritis, rheumatoid arthritis, multiple sclerosis, asthma, inflammatory bowel disease, transplant rejection and graft vs. host disease.

Also, with respect to the glucocorticoid receptor pathway, it is known that glucocorticoids are potent anti-inflammatory agents, however their systemic use is limited by side effects. Compounds that retain the anti-inflammatory efficacy of glucocorticoids while minimizing the side effects such as diabetes, osteoporosis and glaucoma would be of great benefit to a very large number of patients with inflammatory diseases.

Additionally concerning GR, the art is in need of compounds that antagonize transactivation. Such compounds may be useful in treating metabolic diseases associated with increased levels of glucocorticoid, such as diabetes, osteoporosis and glaucoma.

Additionally concerning GR, the art is in need of compounds that cause transactivation. Such compounds may be useful in treating metabolic diseases associated with a deficiency in glucocorticoid. Such diseases include Addison's disease.

DESCRIPTION OF THE INVENTION

The present invention relates to new non-steroidal compounds which are effective modulators of the glucocorticoid receptor, AP-1, and/or NF-κB activity and thus are useful in treating diseases or disorders including metabolic and inflammatory or immune associated diseases or disorders. The present invention also provides compositions and combinations thereof and methods for using such compounds, combinations and compositions to treat these and related diseases or disorders.

In accordance with one aspect of the invention (Embodiment 1), compounds are provided having the structure of formula I:

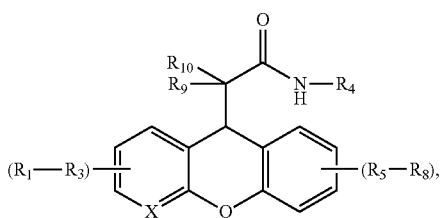

an enantiomer, diastereomer, tautomer, or a pharmaceutically-acceptable salt thereof, wherein:

X is selected from N and $CR_1$;

$R_1$, $R_2$, $R_3$, $R_5$, $R_6$, $R_7$, and $R_8$ are the same or different and at each occurrence are independently selected from hydrogen, halogen, $C_{1-8}$alkyl, substituted $C_{1-8}$alkyl, $C_{2-8}$alkenyl, substituted $C_{2-8}$alkenyl, $C_{2-8}$alkynyl, $C_{2-8}$substituted alkynyl, nitro, cyano, dialkylaminoalkoxy, alkoxyalkyloxyalkyloxy, $C_{3-7}$cycloalkyl, $C_{3-7}$cycloalkenyl, $C_{3-7}$cycloalkynyl, heterocyclo, aryl, and heteroaryl, wherein said cycloalkyl, cycloalkenyl, heterocyclo, aryl, and heteroaryl are each substituted with zero to three halogen, $C_{1-6}$alkyl, $C_{1-6}$hydroxyalkyl, $C_{1-6}$haloalkyl, $C_{1-6}$alkoxy, $C_{1-6}$haloalkoxy, —$OR_{12}$, =O, —$NR_{12}R_{13}$, —$C(=O)R_{12}$, —$C(=O)OR_{12}$, —$C(=O)NR_{12}R_{13}$, —$OC(=O)NR_{12}$, $R_{13}$, —$NR_{12}C(O)NR_{12}R_{13}$, —$OC(=O)R_{12}$, —$NR_{12}C(=O)R_{13}$, —$NR_{12}C(O)OR_{13}$, —$NR_{12}C(S)OR_{13}$, —$S(O)_pR_{14}$, —$NR_{12}SO_2R_{14}$, $SO_2NR_{12}R_{13}$, $C_{3-7}$cycloalkyl, 3- to 6-membered heterocyclo, phenyl, and 5- to 6-membered heteroaryl optionally substituted with $C_{1-3}$alkyl, $C_{1-3}$hydroxyalkyl, $C_{1-3}$haloalkyl, $C_{1-3}$alkoxy, or $C_{1-3}$haloalkoxy;

$R_4$ is $C(O)R_{11}$;

$R_9$ and $R_{10}$ are the same or different and at each occurrence are independently $C_{1-6}$alkyl; or $R_9$ and $R_{10}$ are taken together with the atom to which they are attached to form a $C_{3-7}$cycloalkyl, $C_{3-7}$cycloalkenyl, or heterocyclo group;

$R_{11}$ at each occurrence is independently selected from $C_{1-6}$alkyl, —$OR_{15}$, —$NR_{15}R_{16}$, $C_{3-7}$cycloalkyl, 3- to 6-membered heterocyclo, phenyl, and 5- to 6-membered heteroaryl optionally substituted with $C_{1-3}$ alkyl, $C_{1-3}$hydroxyalkyl, $C_{1-3}$ haloalkyl, $C_{1-3}$alkoxy, or $C_{1-3}$haloalkoxy;

$R_{12}$ and $R_{13}$ are the same or different and at each occurrence are independently selected from (i) hydrogen, $C_{1-8}$alkyl, substituted $C_{1-8}$alkyl, $C_{2-8}$alkenyl, substituted $C_{2-8}$alkenyl, $C_{2-8}$alkynyl, substituted $C_{2-8}$alkynyl, $C_{3-7}$cycloalkyl, $C_{3-7}$cycloalkenyl, aryl, heteroaryl, and heterocyclo; or (ii) where possible, $R_{12}$ is taken together with $R_{13}$ to form a heteroaryl or heterocyclo ring each optionally substituted with OH, oxo, $C_{1-4}$alkoxy, $C_{1-4}$ alkyl, halogen, and $C_{1-4}$haloalkyl;

$R_{14}$ at each occurrence is independently selected from $C_{1-8}$alkyl, substituted $C_{1-8}$alkyl, $C_{2-8}$alkenyl, substituted $C_{2-8}$alkenyl, $C_{2-8}$alkynyl, substituted $C_{2-8}$alkynyl, $C_{3-7}$cycloalkyl, $C_{3-7}$cycloalkenyl, aryl, heteroaryl, and heterocyclo; $R_{15}$ and $R_{16}$ are the same or different and at each occurrence are independently selected from (i) hydrogen, $C_{1-8}$alkyl, substituted $C_{1-8}$alkyl, $C_{2-8}$alkenyl, substituted $C_{2-8}$alkenyl, $C_{2-8}$alkynyl, substituted $C_{2-8}$alkynyl, $C_{3-7}$cycloalkyl, $C_{3-7}$cycloalkenyl, aryl, heteroaryl, and heterocyclo; or (ii) where possible, $R_{15}$ is taken together with $R_{16}$ to form a heteroaryl or heterocyclo ring; p is 0, 1 and 2; and provided the following compounds are excluded:

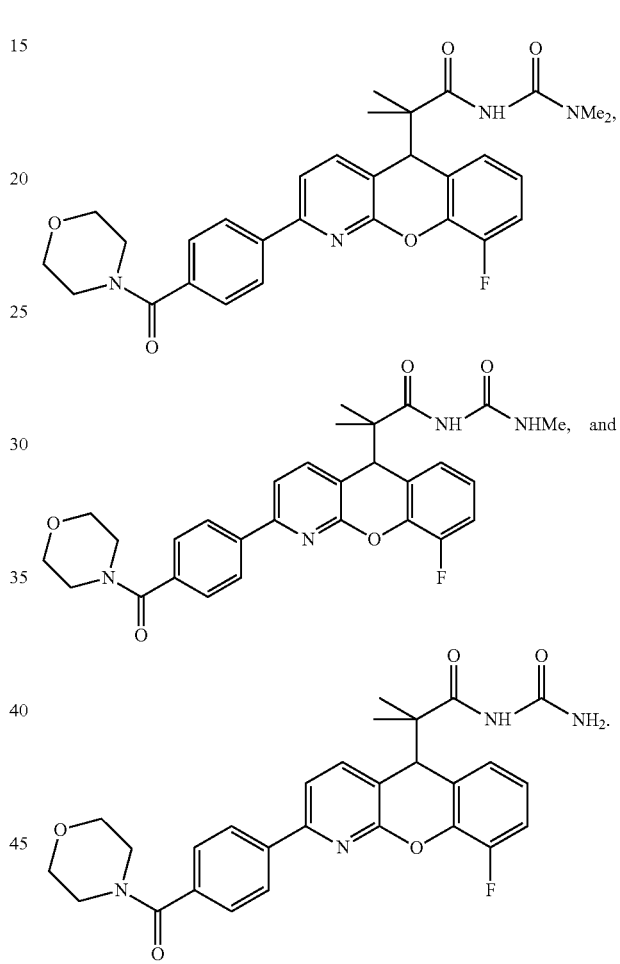

Other Embodiments of the present invention are as described below.

Embodiment 2: a compound as defined in Embodiment 1, having the following formula II:

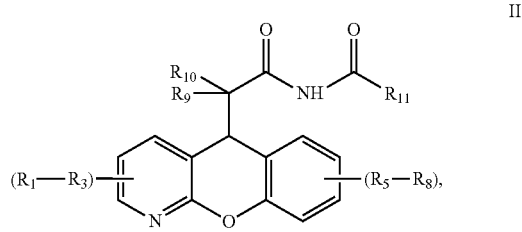

or an enantiomer, diastereomer, tautomer, or a pharmaceutically-acceptable salt thereof, wherein:

$R_1$, $R_2$, and $R_3$ are the same or different and at each occurrence are independently selected from halogen, $C_{1-8}$alkyl, cyano, $C_{3-7}$cycloalkyl, 3- to 10-membered heterocyclo, 5- to 10-membered aryl, and 5- to 10-membered heteroaryl, wherein said alkyl, alkoxy, cycloalkyl, heterocyclo, aryl, and heteroaryl are each substituted with zero to three substituents independently selected from halogen, $C_{1-6}$alkyl, $C_{1-6}$hydroxyalkyl, $C_{1-6}$haloalkyl, $C_{1-6}$alkoxy, $C_{1-6}$haloalkoxy, —$OR_{12}$, —$NR_{12}R_{13}$, —$C(=O)R_{12}$, —$C(=O)OR_{12}$, —$C(=O)NR_{12}R_{13}$, —$OC(=O)NR_{12}$, $R_{13}$, —$NR_{12}C(O)NR_{12}R_{13}$, —$OC(=O)R_{12}$, —$NR_{12}C(=O)R_{13}$, —$NR_{12}C(O)OR_{13}$, —$NR_{12}C(S)OR_{13}$, —$S(O)_pR_{14}$, —$NR_{12}SO_2R_{14}$, $SO_2NR_{12}R_{13}$, $C_{3-7}$cycloalkyl, 3- to 6-membered heterocyclo, phenyl, and 5- to 6-membered heteroaryl optionally substituted with $C_{1-3}$alkyl, $C_{1-3}$hydroxyalkyl, $C_{1-3}$haloalkyl, $C_{1-3}$alkoxy, or $C_{1-3}$haloalkoxy;

$R_5$, $R_6$, $R_7$, and $R_8$ are the same or different and at each occurrence are independently selected from hydrogen, halogen, and $C_{1-6}$alkyl;

$R_{11}$ at each occurrence is independently selected from $C_{1-6}$alkyl, —$NR_{15}R_{16}$, $C_{3-7}$cycloalkyl, and 3- to 6-membered heterocycle;

$R_{12}$ and $R_{13}$ are the same or different and at each occurrence are independently selected from (i) hydrogen, $C_{1-6}$alkyl, $C_{1-6}$hydroxyalkyl, $C_{1-6}$haloalkyl, $C_{1-6}$alkoxy, $C_{1-6}$haloalkoxy, $C_{3-7}$cycloalkyl, phenyl, 5- to 6-membered heteroaryl, and 5- to 6-membered heterocyclo; or (ii) where possible, $R_{12}$ is taken together with $R_{13}$ to form a 5- to 6-membered heteroaryl or 4- to 6-membered heterocyclo ring optionally substituted with OH, oxo, $C_{1-4}$alkoxy, $C_{1-4}$alkyl, halogen, and $C_{1-4}$haloalkyl;

$R_{14}$ at each occurrence is independently selected from $C_{1-6}$alkyl, $C_{1-6}$hydroxyalkyl, $C_{1-6}$haloalkyl, $C_{1-6}$alkoxy, $C_{1-6}$haloalkoxy, $C_{3-7}$cycloalkyl, phenyl, 5- to 6-membered heteroaryl, and 5- to 6-membered heterocycle; and $R_{15}$, and $R_{16}$ are the same or different and at each occurrence are independently selected from (i) hydrogen, $C_{1-8}$alkyl, substituted $C_{1-8}$alkyl, $C_{2-8}$alkenyl, substituted $C_{2-8}$alkenyl, $C_{2-8}$alkynyl, substituted $C_{2-8}$alkynyl, $C_{3-7}$cycloalkyl, $C_{3-7}$cycloalkenyl, aryl, heteroaryl, and heterocyclo; or (ii) where possible, $R_{15}$ is taken together with $R_{16}$ to form a heteroaryl or heterocyclo ring.

Embodiment 3: a compound as defined in Embodiments 1-2, having the following formula III:

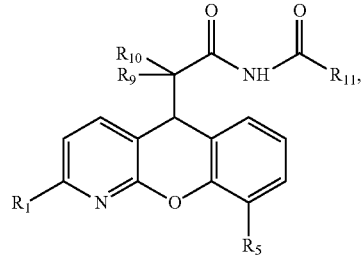

III or an enantiomer, diastereomer, tautomer, or a pharmaceutically-acceptable salt thereof, wherein:

$R_1$ is independently selected from 5- to 10-membered aryl and 5- to 10-membered heteroaryl, wherein said aryl and heteroaryl group are each substituted with zero to three substituents independently selected from halogen, $C_{1-6}$hydroxyalkyl, —$OR_{12}$, —$NR_{12}R_{13}$, —$C(=O)R_{12}$, —$C(=O)OR_{12}$, —$C(=O)NR_{12}$, $R_{13}$, —$NR_{12}C(=O)R_{13}$, —$S(O)_2R_{14}$, —$NR_{12}SO_2R_{14}$, phenyl, and 5- to 6-membered heteroaryl optionally substituted with $C_{1-3}$alkyl;

$R_5$ is independently selected from is hydrogen and halogen;

$R_9$ and $R_{10}$ are $C_{1-3}$alkyl;

$R_{12}$ and $R_{13}$ are the same or different and at each occurrence are independently selected from (i) hydrogen, $C_{1-6}$alkyl, $C_{1-6}$haloalkyl, and 5- to 6-membered heterocyclo; or (ii) where possible, $R_{12}$ is taken together with $R_{13}$ to form a 4- to 6-membered heterocyclo ring optionally substituted with $C_{1-3}$alkyl and oxo; and $R_{14}$ at each occurrence is independently $C_{1-6}$alkyl.

Embodiment 4: a compound as defined in Embodiments 1-3, or an enantiomer, diasteremer, tautomer, or a pharmaceutically-acceptable salt thereof, wherein:

$R_{11}$ at each occurrence is independently selected from $C_{1-6}$alkyl, $C_{3-7}$cycloalkyl, and —$NR_{15}R_{16}$; and $R_{15}$ and $R_{16}$ are the same or different and at each occurrence are independently selected from (i) hydrogen, $C_{1-8}$alkyl, substituted $C_{1-8}$alkyl wherein the substituent is selected from OH and aryl optionally substitute with $C_{1-4}$alkoxy, $C_{3-7}$cycloalkyl, $C_{3-7}$cycloalkenyl, aryl, heteroaryl, and heterocyclo; or (ii) where possible, $R_{15}$ is taken together with $R_{16}$ to form a heteroaryl or heterocyclo ring.

Embodiment 5: the compound as defined in Embodiments 1-4, or an enantiomer, diastereomer, tautomer, or a pharmaceutically-acceptable salt thereof, wherein:

$R_1$ is phenyl, pyridyl or pyrimidinyl, each of which is substituted with zero to three substituents independently selected from halogen, $C_{1-6}$hydroxyalkyl, —$OR_{12}$, —$NR_{12}R_{13}$, —$C(=O)R_{12}$, —$C(=O)OR_{12}$, —$C(=O)NR_{12}$, $R_{13}$, —$NR_{12}C(=O)R_{13}$, —$S(O)_2R_{14}$, —$NR_{12}SO_2R_{14}$, and 5- to 6-membered heteroaryl substituted with $C_{1-3}$alkyl group.

Embodiment 6: a compound as defined in Embodiments 1-5, or an enantiomer, diasteremer, tautomer, or a pharmaceutically-acceptable salt thereof, wherein:

$R_1$ is phenyl, pyridyl or pyrimidinyl, each of which is substituted with zero to three substituents independently selected from F, Cl, —$OCF_3$, —$NH_2$,

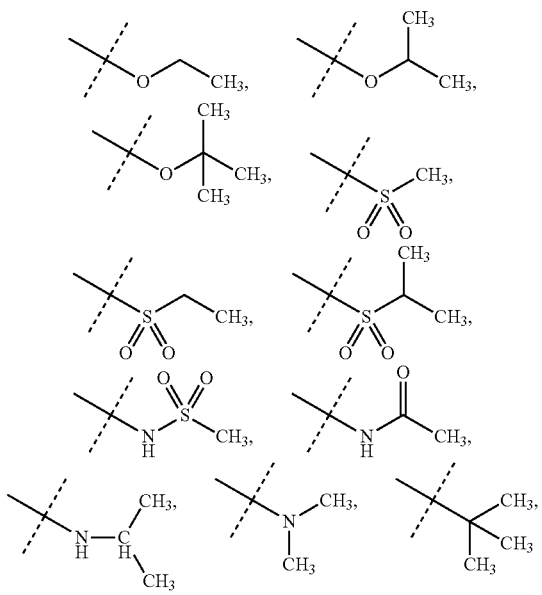

-continued

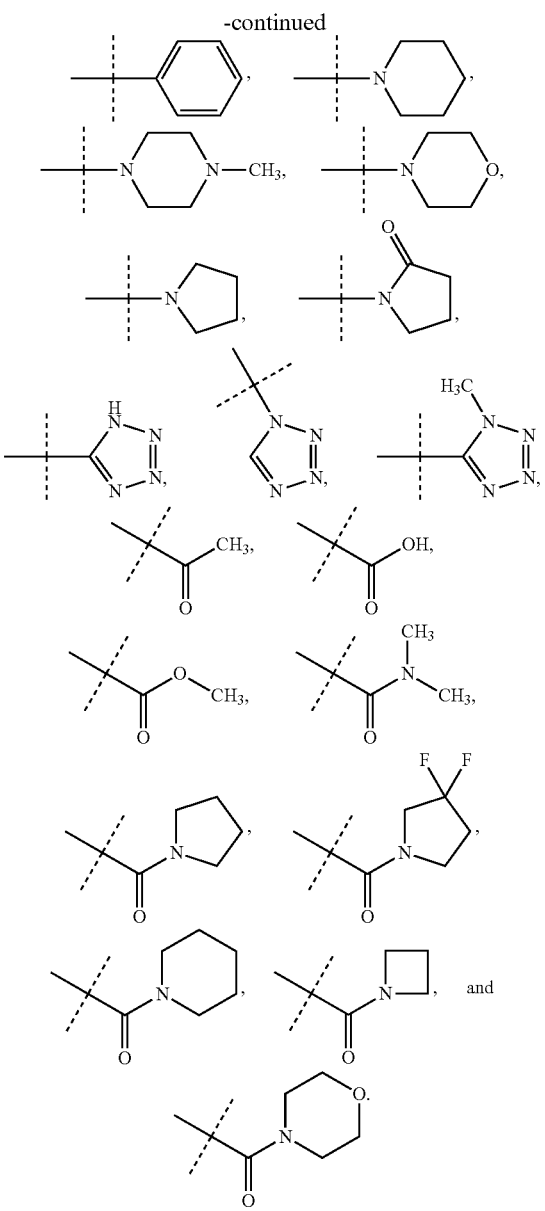

Embodiment 7: a compound as defined in Embodiments 1-6, or an enantiomer, diastereomer, tautomer, or a pharmaceutically-acceptable salt thereof, wherein:

$R_1$ is phenyl, pyridyl or pyrimidinyl, each of which is substituted with zero to three substituents independently selected from halogen, $C_{1-6}$hydroxyalkyl, —$OR_{12}$, —$NR_{12}R_{13}$, —$C(=O)R_{12}$, —$C(=O)OR_{12}$, —$C(=O)NR_{12}$, $R_{13}$, —$NR_{12}C(=O)R_{13}$, —$S(O)_2R_{14}$, —$NR_{12}SO_2R_{14}$, and 5- to 6-membered heteroaryl substituted with $C_{1-3}$alkyl; and $R_{11}$ at each occurrence is independently selected from $C_{1-6}$alkyl, and $C_{3-7}$cycloalkyl.

Embodiment 8: a compound as defined in Embodiments 1-7, or an enantiomer, diastereomer, tautomer, or a pharmaceutically-acceptable salt thereof, wherein:

$R_1$ is phenyl, pyridyl or pyrimidinyl, each of which is substituted with zero to three substituents independently selected from halogen, $C_{1-6}$hydroxyalkyl, —$OR_{12}$, —$NR_{12}R_{13}$, —$C(=O)R_{12}$, —$C(=O)OR_{12}$, —$C(=O)NR_{12}$, $R_{13}$, —$NR_{12}C(=O)R_{13}$, —$S(O)_2R_{14}$, —$NR_{12}SO_2R_{14}$, and 5- to 6-membered heteroaryl substituted with $C_{1-3}$alkyl;

$R_{11}$ at each occurrence is independently selected from —$NR_{15}R_{16}$ and 3- to 6-membered heterocycle; and $R_{15}$ and $R_{16}$ are the same or different and at each occurrence are independently selected from (i) hydrogen, $C_{1-8}$alkyl, substituted $C_{1-8}$alkyl wherein the substituent is selected from OH and aryl optionally substitute with $C_{1-4}$alkoxy, $C_{3-7}$cycloalkyl, $C_{3-7}$cycloalkenyl, aryl, heteroaryl, and heterocyclo; or (ii) where possible, $R_{15}$ is taken together with $R_{16}$ to form a heteroaryl or heterocyclo ring.

Embodiment 9: a compound as defined in Embodiments 1-8, having the following formula IV:

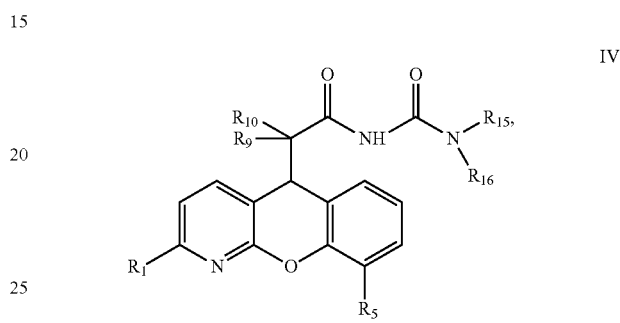

or an enantiomer, diastereomer, tautomer, or a pharmaceutically-acceptable salt thereof, wherein:

$R_1$ is phenyl, pyridyl or pyrimidinyl, each of which is substituted with zero to three substituents independently selected from F, Cl, —$OCF_3$, —$NH_2$,

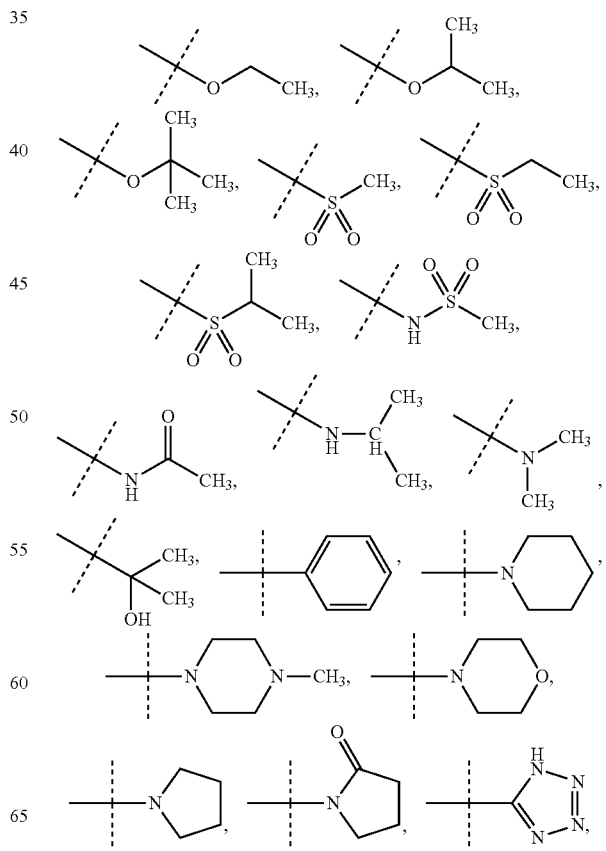

-continued

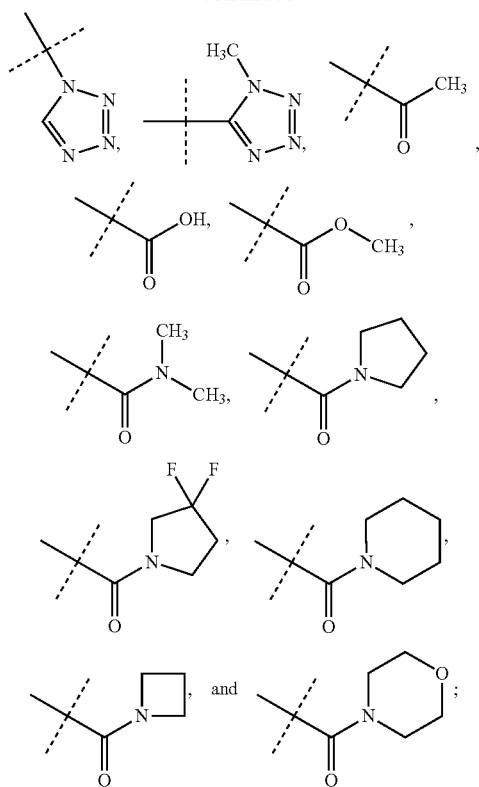

R₅ is independently selected from hydrogen and halogen;
R₉ and R₁₀ are C₁₋₃alkyl; and
R₁₅ and R₁₆ are the same or different and at each occurrence are independently selected from (i) hydrogen, methyl, ethyl, propyl, butyl, C₁₋₃alkyl substituted with OH or phenyl optionally substitute with methoxy, cyclopropyl, cyclobutyl, cyclopentyl, cyclohexyl, phenyl, and heteroaryl; or (ii) where possible, R₁₅ is taken together with R₁₆ to form

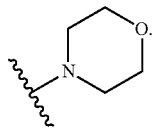 [SMILES: *N1CCOCC1]

Embodiment 10: a compound as defined in Embodiments 1-9, or an enantiomer, diastereomer, tautomer, or a pharmaceutically-acceptable salt thereof, wherein:
R₁ is

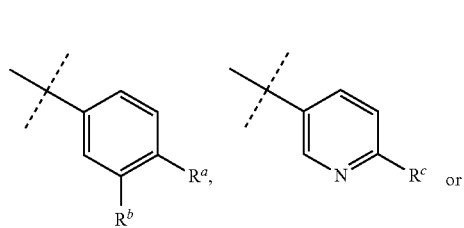

-continued

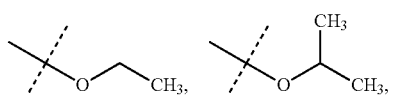

$R^a$ is H, —OCF₃, —NH₂,

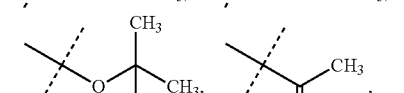

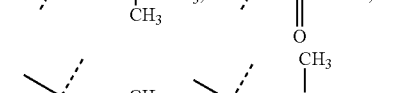

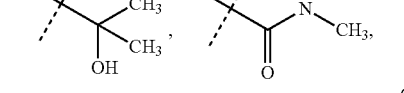

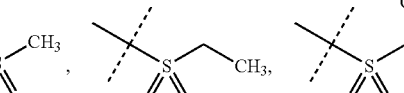

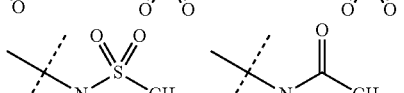

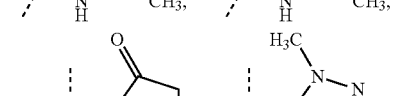

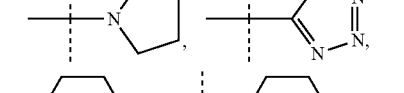

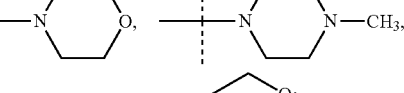

$R^b$ is H, F, or Cl; and

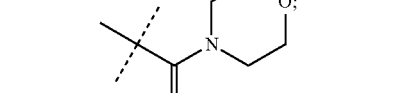

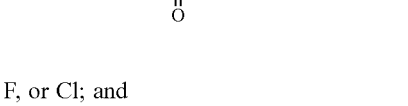

$R^c$ is H, F,

Embodiment 11: a compound as defined in Embodiment 1, having the following formula V:

V

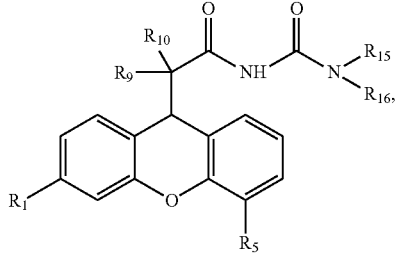

or an enantiomer, diastereomer, tautomer, or a pharmaceutically-acceptable salt thereof, wherein:

$R_1$ at each occurrence are independently selected from hydrogen, halogen, $C_{1-8}$alkyl, substituted $C_{1-8}$alkyl, $C_{2-8}$alkenyl, substituted $C_{2-8}$alkenyl, $C_{2-8}$alkynyl, $C_{2-8}$substituted alkynyl, nitro, cyano, dialkylaminoalkoxy, alkoxyalkyloxyalkyloxy, $C_{3-7}$cycloalkyl, $C_{3-7}$cycloalkenyl, $C_{3-7}$cycloalkynyl, heterocyclo, aryl, and heteroaryl, wherein said cycloalkyl, cycloalkenyl, heterocyclo, aryl, and heteroaryl are each substituted with zero to three halogen, $C_{1-6}$alkyl, $C_{1-6}$hydroxyalkyl, $C_{1-6}$haloalkyl, $C_{1-6}$alkoxy, $C_{1-6}$haloalkoxy, —$OR_{12}$, =O, —$NR_{12}R_{13}$, —C(=O)$R_{12}$, —C(=O)$OR_{12}$, —C(=O)$NR_{12}R_{13}$, —OC(=O)$NR_{12}$, $R_{13}$, —$NR_{12}$C(O)$NR_{12}R_{13}$, —OC(=O)$R_{12}$, —$NR_{12}$C(=O)$R_{13}$, —$NR_{12}$C(O)$OR_{13}$, —$NR_{12}$C(S)$OR_{13}$, —S(O)$_p R_{14}$, —$NR_{12}$SO$_2 R_{14}$, SO$_2 NR_{12}R_{13}$, $C_{3-7}$cycloalkyl, 3- to 6-membered heterocyclo, phenyl, and 5- to 6-membered heteroaryl optionally substituted with $C_{1-3}$alkyl, $C_{1-3}$hydroxyalkyl, $C_{1-3}$haloalkyl, $C_{1-3}$alkoxy, or $C_{1-3}$haloalkoxy;

$R_9$ and $R_{10}$ are the same or different and at each occurrence are independently $C_{1-6}$alkyl; or $R_9$ and $R_{10}$ are taken together with the atom to which they are attached to form a $C_{3-7}$cycloalkyl, $C_{3-7}$cycloalkenyl, or heterocyclo group;

$R_{12}$ and $R_{13}$ are the same or different and at each occurrence are independently selected from (i) hydrogen, $C_{1-8}$alkyl, substituted $C_{1-8}$alkyl, $C_{2-8}$alkenyl, substituted $C_{2-8}$alkenyl, $C_{2-8}$alkynyl, substituted $C_{2-8}$alkynyl, $C_{3-7}$cycloalkyl, $C_{3-7}$cycloalkenyl, aryl, heteroaryl, and heterocyclo; or (ii) where possible, $R_{12}$ is taken together with $R_{13}$ to form a heteroaryl or heterocyclo ring each optionally substituted with OH, oxo, $C_{1-4}$alkoxy, $C_{1-4}$alkyl, halogen, and $C_{1-4}$haloalkyl;

$R_{14}$ at each occurrence is independently selected from $C_{1-8}$alkyl, substituted $C_{1-8}$alkyl, $C_{2-8}$alkenyl, substituted $C_{2-8}$alkenyl, $C_{2-8}$alkynyl, substituted $C_{2-8}$alkynyl, $C_{3-7}$cycloalkyl, $C_{3-7}$cycloalkenyl, aryl, heteroaryl, and heterocyclo;

$R_{15}$ and $R_{16}$ are the same or different and at each occurrence are independently selected from (i) hydrogen, $C_{1-8}$alkyl, substituted $C_{1-8}$alkyl, $C_{2-8}$alkenyl, substituted $C_{2-8}$alkenyl, $C_{2-8}$alkynyl, substituted $C_{2-8}$alkynyl, $C_{3-7}$cycloalkyl, $C_{3-7}$cycloalkenyl, aryl, heteroaryl, and heterocyclo; or (ii) where possible, $R_{15}$ is taken together with $R_{16}$ to form a heteroaryl or heterocyclo ring; p is 0, 1 and 2.

Embodiment 12: a compound, or an enantiomer, diastereomer, tautomer, or a pharmaceutically-acceptable salt thereof, selected from Examples 1-84.

Embodiment 13: a compound as defined in Embodiments 1-11, or an enantiomer, diastereomer, tautomer, or a pharmaceutically-acceptable salt thereof, wherein:

$R_1$, $R_2$, $R_4$, $R_5$, $R_6$, $R_7$, and $R_8$ are the same or different and at each occurrence are independently selected from (i) hydrogen, halogen, alkyl, substituted alkyl, alkenyl, substituted alkenyl, alkynyl, substituted alkynyl, alkoxy, substituted alkoxy, nitro, cyano, $OR_{12}$, —$NR_{12}R_{13}$, —C(=O)$R_{12}$, —CO$_2 R_{12}$, —C(=O)$NR_{12}R_{13}$, —OC(=O)$NR_{12}$, $R_{13}$,

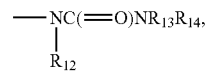

—OC(=O)$R_{12}$, —$NR_{12}$C(=O)$R_{13}$, —$NR_{12}$C(O)$OR_{13}$, —$NR_{12}$C(S)$OR_{13}$, —S(O)$_p R_{14}$, $NR_{12}$SO$_2 R_{14}$, dialkylaminoalkoxy, alkoxyalkyloxyalkyloxy, SO$_2 NR_{12}R_{13}$, $C_{3-6}$cycloalkyl, $C_{3-6}$cycloalkenyl, $C_{3-6}$cycloalkynyl, heterocyclo, aryl, and heteroaryl; and/or (ii) where possible, together with the atoms to which they are attached, each one of $R_1$, $R_2$, $R_4$, $R_5$, $R_7$, and $R_8$ is taken together with any one of $R_1$, $R_2$, $R_4$, $R_5$, $R_7$, and $R_8$ located on an adjacent atom to form a fused ring;

$R_{12}$ and $R_{13}$ are the same or different and at each occurrence are independently selected from hydrogen, alkyl, substituted alkyl, alkenyl, substituted alkenyl, alkynyl, substituted alkynyl, cycloalkyl, cycloalkenyl, aryl, heteroaryl, and heterocyclo; and p is 0, 1 or 2.

Embodiment 14: a compound as defined in Embodiments 1-3, or an enantiomer, diastereomer, tautomer, or a pharmaceutically-acceptable salt thereof, wherein one of $R_1$, $R_2$, and $R_3$ is substituted aryl or substituted heteroaryl.

Embodiment 15: the compound as defined in Embodiments 1-4, or an enantiomer, diastereomer, tautomer, or a pharmaceutically-acceptable salt, thereof, wherein $R_1$ is selected from hydrogen, alkyl, alkenyl, aryl, substituted aryl, cyano, CF$_3$, alkoxy, halogen, hydroxyl, dialkylamino, monoalkylamino, dialkylaminoalkoxy, alkoxyalkoxyalkoxy, and a 4- to 7-membered heterocyclo having one to three heteroatoms selected from O, S and N. Preferred compounds are those where $R_1$ is hydrogen, $C_{1-6}$alkyl, halogen, cyano, —SC$_{1-6}$alkyl, $C_{2-6}$alkenyl, (un)substituted phenyl, (C$_{1-6}$alkyl)$_{1-2}$amino, and a 5- to 6-membered heterocyclo having one to three heteroatoms selected from O, S, and N. Especially preferred compounds are those where $R_1$ is substituted phenyl.

Embodiment 16: a compound as defined in Embodiments 1-5, or an enantiomer, diastereomer, tautomer, or a pharmaceutically-acceptable salt thereof, wherein $R_5$ is selected from hydrogen, haloalkyl, alkoxy, haloalkoxy, halogen, amino, dialkylamino, heterocyclo, phenyl, and halophenyl. Preferably, $R_5$ is halogen.

Embodiment 17: a compound as defined in Embodiments 1-6, or an enantiomer, diastereomer, tautomer, or a pharmaceutically-acceptable salt thereof, wherein:

$R_1$ is selected from 5- to 10-membered aryl and 5- to 10-membered heteroaryl, wherein said aryl and heteroaryl group are each substituted with zero to three substituents independently selected from halogen, $C_{1-6}$hydroxyalkyl, —$OR_{12}$, —$NR_{12}R_{13}$, —C(=O)$R_{12}$, —C(=O)$OR_{12}$, —C(=O)$NR_{12}$, $R_{13}$, —$NR_{12}$C(=O)$R_{13}$, —S(O)$_2 R_{14}$, —$NR_{12}$SO$_2 R_{14}$, and 5- to 6-membered heteroaryl substituted with $C_{1-3}$alkyl group; and $R_5$ is fluoro, chloro, or dimethylamino.

Embodiment 18: a compound as defined in Embodiments 1-7, or an enantiomer, diastereomer, tautomer, or a pharmaceutically-acceptable salt thereof, wherein:

$R_9$ and $R_{10}$ are each independently selected from methyl, or combined with the carbon they are attached to form cyclopropyl, cyclobutyl, and cyclopentyl, and especially wherein $R_9$ and $R_{10}$ are each methyl.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements (including individual variable definitions) of an embodiment are meant to be combined with any and all other elements from any of the embodiments to describe additional embodiments. The present invention also provides a pharmaceutical composition comprising a compound of formula I, or an enantiomer, diastereomer, or a pharmaceutically-acceptable salt, and a pharmaceutically acceptable carrier therefore.

Other embodiments of the present invention are 1) a method of treating a disease or disorder comprising administering to a patient in need of treatment a therapeutically effective amount of a compound of formula I, 2) a compound of formula I for use in treating a disease or disorder, and 3) use of a compound of formula I in the manufacture of a medicament for treating a disease or disorder, wherein the disease or disorder is selected from an endocrine disorder, rheumatic disorder, collagen disease, dermatologic disease, allergic disease, ophthalmic disease, respiratory disease, hematologic disease, gastrointestinal disease, inflammatory disease, immune disease, neoplastic disease and metabolic disease.

In still another embodiment, the present invention provides a method of treating endocrine disorder, rheumatic disorder, collagen disease, dermatologic disease, allergic disease, ophthalmic disease, respiratory disease, hematologic disease, gastrointestinal disease, inflammatory disease, immune disease, neoplastic disease and metabolic disease, a disease associated with the expression product of a gene whose transcription is stimulated or repressed by glucocorticoid receptors, or a disease associated with AP-1- and/or NFκB-induced transcription, or a disease associated with AP-1 and/or NFκB dependent gene expression, wherein the disease is associated with the expression of a gene under the regulatory control of AP-1 and/or NF-κB (particularly AP-1), including inflammatory and immune diseases and disorders as described hereinafter, which includes the step of administering a therapeutically effective amount of a compound of formula I of the invention to a patient.

Other embodiments of the present invention are 1) a method of treating a disease or disorder comprising administering to a patient in need of treatment a therapeutically effective amount of a compound of formula I, 2) a compound of formula I for use in treating a disease or disorder, and 3) use of a compound of formula I in the manufacture of a medicament for treating a disease or disorder wherein the disease or disorder is selected from a metabolic disease or an inflammatory or immune disease comprising the administration to a patient in need of treatment, a therapeutically effective amount of a compound of formula I.

A more preferred embodiment of the present invention provides 1) a method of treating a disease or disorder comprising administering to a patient in need of treatment a therapeutically effective amount of a compound of formula I, 2) a compound of formula I for use in treating a disease or disorder, and 3) use of a compound of formula I in the manufacture of a medicament for treating a disease or disorder wherein the disease or disorder is selected from a metabolic disease wherein the disease is a metabolic disease selected from Type I diabetes, Type II diabetes, juvenile diabetes, and obesity.

Other preferred embodiments of the present invention are 1) a method of treating a disease or disorder comprising administering to a patient in need of treatment a therapeutically effective amount of a compound of formula I, 2) a compound of formula I for use in treating a disease or disorder, and 3) use of a compound of formula I in the manufacture of a medicament for treating a disease or disorder, wherein the disease or disorder is an inflammatory or immune disease selected from transplant rejection of kidney, liver, heart, lung, pancreas, bone marrow, cornea, small bowel, skin allografts, skin homografts, heart valve xenograft, serum sickness, and graft vs. host disease, rheumatoid arthritis, psoriatic arthritis, multiple sclerosis, asthma, inflammatory bowel disease, Crohn's disease, ulcerative colitis, pyoderma gangrenum, systemic lupus erythematosis, myasthenia gravis, psoriasis, dermatitis, dermatomyositis, eczema, seborrhoea, pulmonary inflammation, eye uveitis, hepatitis, Graves' disease, Hashimoto's thyroiditis, autoimmune thyroiditis, Behcet's or Sjögren's syndrome, pernicious or immunohaemolytic anemia, atherosclerosis, Addison's disease, idiopathic adrenal insufficiency, autoimmune polyglandular disease, glomerulonephritis, scleroderma, morphea, lichen planus, vitiligo, alopecia areata, autoimmune alopecia, autoimmune hypopituitarism, Guillain-Barre syndrome, alveolitis, contact hypersensitivity, delayed-type hypersensitivity, contact dermatitis, urticaria, skin allergies, respiratory allergies, hay fever, gluten-sensitive enteropathy, osteoarthritis, acute pancreatitis, chronic pancreatitis, acute respiratory distress syndrome, Sezary's syndrome, restenosis, stenosis, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetitformis, severe erythema multiforme, exfoliative dermatitis, seborrheic dermatitis, seasonal or perennial allergic rhinitis, bronchial asthma, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, regional enteritis, autoimmune vasculitis, sepsis, and chronic obstructive pulmonary disease.

Especially preferred embodiments are 1) a method of treating a disease or disorder comprising administering to a patient in need of treatment a therapeutically effective amount of a compound of formula I, 2) a compound of formula I for use in treating a disease or disorder, and 3) use of a compound of formula I in the manufacture of a medicament for treating a disease or disorder where the disease or disorder is selected from transplant rejection, rheumatoid arthritis, psoriatic arthritis, multiple sclerosis, asthma, inflammatory bowel disease, systemic lupus erythematosis, and psoriasis. Another embodiment of the present invention involves a method for treating a disease or disorder associated with the expression product of a gene whose transcription is stimulated or repressed by glucocorticoid receptors, or a method of treating a disease or disorder associated with AP-1- and/or NF-κB—(particularly AP-1-) induced transcription, or a method for treating a disease or disorder associated with AP-1 and/or NF-κB (particularly AP-1) dependent gene expression, wherein the disease is associated with the expression of a gene under the regulatory control of AP-1 and/or NF-κβ (particularly AP-1), such as inflammatory and immune disorders, cancer and tumor disorders, such as solid tumors, lymphomas and leukemia, and fungal infections such as mycosis fungoides.

In still another embodiment, the present invention provides a pharmaceutical combination comprising one or more compounds of Formula I and an immunosuppressant, an anticancer agent, an anti-viral agent, an anti-inflammatory agent, an anti-fungal agent, an anti-biotic, an anti-vascular hyperproliferation agent, an anti-depressant agent, a lipid-lowering agent, a lipid modulating agent, an antidiabetic agent, an anti-obesity agent, an antihypertensive agent, a platelet aggregation inhibitor, and/or an antiosteoporosis agent, wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide, wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent, wherein the lipid lowering agent is an MTP inhibitor, an HMG CoA reductase inhibitor, a squalene synthetase inhibitor, a fibric acid derivative, an upregulator of LDL receptor activity, a lipoxygenase inhibitor, or an ACAT inhibitor, wherein the antihypertensive agent is an ACE inhibitor, angiotensin II receptor antagonist, NEP/ACE inhibitor, calcium channel blocker and/or β-adrenergic blocker.

Even more preferred combinations are those wherein the antidiabetic agent is 1, 2, 3 or more of metformin, glyburide, glimepiride, glipyride, glipizide, chlorpropamide, gliclazide, acarbose, miglitol, pioglitazone, troglitazone, rosiglitazone, insulin, Gl-262570, isaglitazone, JTT-501, NN-2344, L895645, YM-440, R-119702, AJ9677, repaglinide, nateglinide, KAD1129, AR-HO39242, GW-409544, KRP297, AC2993, LY315902, P32/98 and/or NVP-DPP-728A, wherein the anti-obesity agent is orlistat, ATL-962, AJ9677, L750355, CP331648, sibutramine, topiramate, AXOKINE®, dexamphetamine, phentermine, phenylpropanolamine, and/or mazindol, wherein the lipid lowering agent is pravastatin, lovastatin, simvastatin, atorvastatin, cerivastatin, fluvastatin, itavastatin, visastatin, fenofibrate, gemfibrozil, clofibrate, avasimibe, TS-962, MD-700, cholestagel, niacin and/or LY295427, wherein the antihypertensive agent is an ACE inhibitor which is captopril, fosinopril, enalapril, lisinopril, quinapril, benazepril, fentiapril, ramipril or moexipril; an NEP/ACE inhibitor which is omapatrilat, [S[(R*,R*)]-hexahydro-6-[(2-mercapto-1-oxo-3-phenylpropyl) amino]-2,2-dimethyl-7-oxo-1H-azepine-1-acetic acid (gemopatrilat) or CGS 30440;

an angiotensin II receptor antagonist which is irbesartan, losartan or valsartan;

amlodipine besylate, prazosin HCl, verapamil, nifedipine, nadolol, propranolol, carvedilol, or clonidine HCl, wherein the platelet aggregation inhibitor is aspirin, clopidogrel, ticlopidine, dipyridamole or ifetroban;

the immunosuppressant is a cyclosporin, mycophenolate, interferon-beta, deoxyspergolin, FK-506 or Ant.-IL-2;

the anti-cancer agent is azathiprine, 5-fluorouracel, cyclophosphamide, cisplatin, methotrexate, thiotepa, or carboplatin;

the anti-viral agent is abacavir, aciclovir, ganciclovir, zidanocin, or vidarabine; and the antiinflammatory drug is ibuprofen, celecoxib, rofecoxib, aspirin, naproxen, ketoprofen, diclofenac sodium, indomethacin, piroxicam, prednisone, dexamethasone, hydrocortisone, or triamcinolone diacetate.

The term "disease associated with GR transactivation", as used herein, refers to a disease associated with the transcription product of a gene whose transcription is transactivated by a GR. Such diseases include, but are not limited to: osteoporosis, diabetes, glaucoma, muscle loss, facial swelling, personality changes, hypertension, obesity, depression, and AIDS, the condition of wound healing, primary or secondary adrenocortical insufficiency, and Addison's disease.

The term "treat", "treating", or "treatment", in all grammatical forms, as used herein refers to the prevention, reduction, or amelioration, partial or complete alleviation, or cure of a disease, disorder, or condition, wherein prevention indicates treatment of a person at risk for developing such a disease, disorder or condition.

The terms "glucocorticoid receptor" and "GR", as used herein, refer either to a member of the nuclear hormone receptor ("NHR") family of transcription factors which bind glucocorticoids and either stimulate or repress transcription, or to GR-beta.

These terms, as used herein, refer to glucocorticoid receptor from any source, including but not limited to: human glucocorticoid receptor as disclosed in Weinberger et al., *Science*, 228:740-742 (1985), and in Weinberger et al., *Nature*, 318:670-672 (1986); rat glucocorticoid receptor as disclosed in Miesfeld, R., *Nature*, 312:779-781 (1985); mouse glucocorticoid receptor as disclosed in Danielson, M. et al., *EMBO J.*, 5:2513; sheep glucocorticoid receptor as disclosed in Yang, K. et al., *J. Mol. Endocrinol.*, 8:173-180 (1992); marmoset glucocorticoid receptor as disclosed in Brandon, D. D. et al., *J. Mol. Endocrinol.*, 7:89-96 (1991); and human GR-beta as disclosed in Hollenberg, S. M. et al., *Nature*, 318:635 (1985); Bamberger, C. M. et al., *J. Clin. Invest.*, 95:2435 (1995).

The term, "disease or disorder associated with AP-1 and/or NF-κB" as used herein, refers to a disease associated with the expression product of a gene under the regulatory control of AP-1 and/or NF-κB. Such diseases include, but are not limited to: inflammatory and immune diseases and disorders; cancer and tumor disorders, such as solid tumors, lymphomas and leukemia; and fungal infections such as mycosis fungoides.

The term "inflammatory or immune associated diseases or disorders" is used herein to encompass any condition, disease, or disorder that has an inflammatory or immune component, including, but not limited to, each of the following conditions: transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, autoimmune diseases, such as rheumatoid arthritis, psoriatic arthritis, multiple sclerosis, Type I and Type II diabetes, juvenile diabetes, obesity, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Graves' disease, Hashimoto's thyroiditis, autoimmune thyroiditis, Behcet's or Sjögren's syndrome (dry eyes/mouth), pernicious or immunohaemolytic anemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, vitiligo (depigmentation of the skin), alopecia areata, autoimmune alopecia, autoimmune hypopituitarism, Guillain-Barre syndrome, and alveolitis; T-cell mediated hypersensitivity diseases, including contact hypersensitivity, delayed-type hypersensitivity, contact dermatitis (including that due to poison ivy), urticaria, skin allergies, respiratory allergies (hay fever, allergic rhinitis) and gluten-sensitive enteropathy (Celiac disease); inflammatory diseases such as osteoarthritis, acute pancreatitis, chronic pancreatitis, acute respiratory distress syndrome, Sezary's syndrome and vascular diseases which have an inflammatory and or a proliferatory component such as restenosis, stenosis and arthrosclerosis. Inflammatory or immune associated diseases or disorders also includes, but is not limited to: endocrine disorders, rheumatic disorders, collagen diseases, dermatologic disease, allergic disease, ophthalmic disease, respiratory disease, hematologic disease, gastrointestinal disease, inflammatory disease, autoimmune disease, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter. Preparation of homochiral examples may be carried out by techniques known to one skilled in the art. For example, homochiral compounds (intermediates or final example compounds) may be prepared by separation of racemic products by chiral phase preparative HPLC. Alternatively, intermediates or example compounds may be prepared by methods known to give enantiomerically enriched products. These include, but are not limited to, the incorporation of chiral auxiliary functionalities into racemic intermediates which serve to control the diaststereoselectivity of transformations, providing enantio-enriched products upon cleavage of the chiral auxiliary.

The compounds of the invention may be prepared by the exemplary processes described in the following reaction Schemes A and B. Exemplary reagents and procedures for these reactions appear hereinafter. Starting materials are commercially available or can be readily prepared by one of ordinary skill in the art. For all of the schemes, the groups $R_1$-$R_3$, $R_5$-$R_8$, $R_9$-$R_{10}$, $R_{11}$, and $R_{15}$-$R_{16}$ are as described herein for a compound of formula I, unless otherwise indicated.

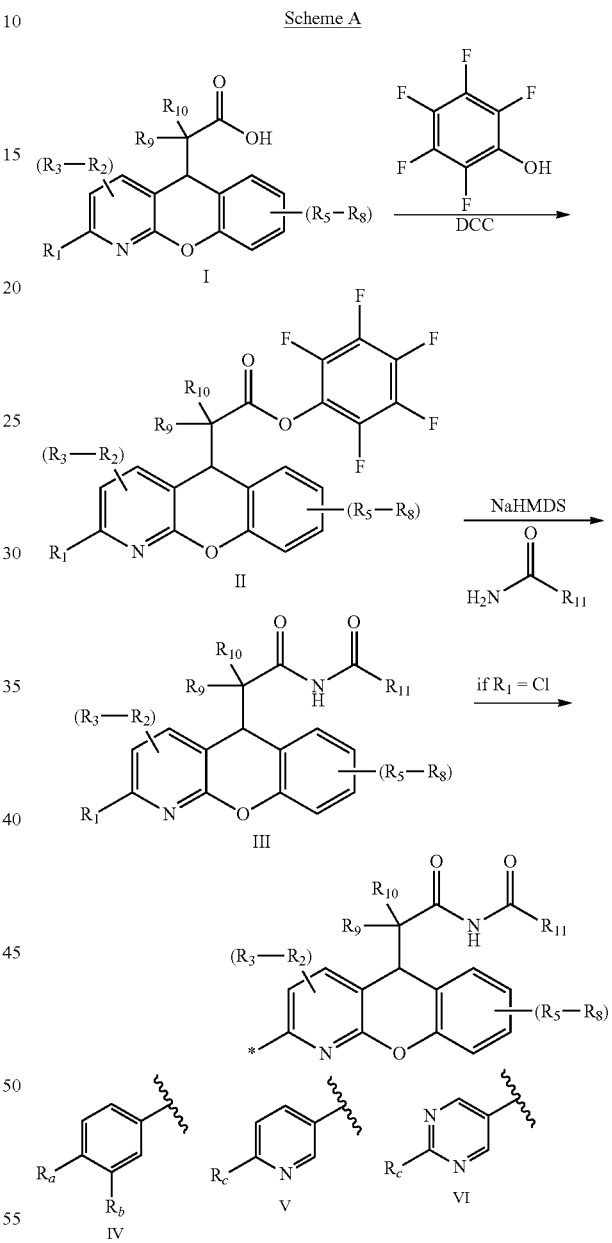

Scheme A

Unsymmetrical linear (acyclic) imides may be prepared as illustrated in Scheme A. The preparation of carboxylic acid I has been described (US 2009/0075995 A1). Following the method of Andrus et al. (*Tetrahedron Lett.*, 5465-5468 (1988)), activation of the acid I with carbodiimide (N,N'-dicyclohexylcarbodiimide or the like) followed by treatment with pentafluorophenol gives an activated pentafluorophenyl ester II. Condensation of ester II with an amide anion, which is separately generated from treatment of an alkyl or cycloalkyl amide with an appropriately strong base such as sodium hexamethyldisilazide) gives acyclic urea III. In cases where $R_1$ is chloro, arylation to give example compounds IV-VI may be effected by methods which have also been described in US 2009/0075995 A1.

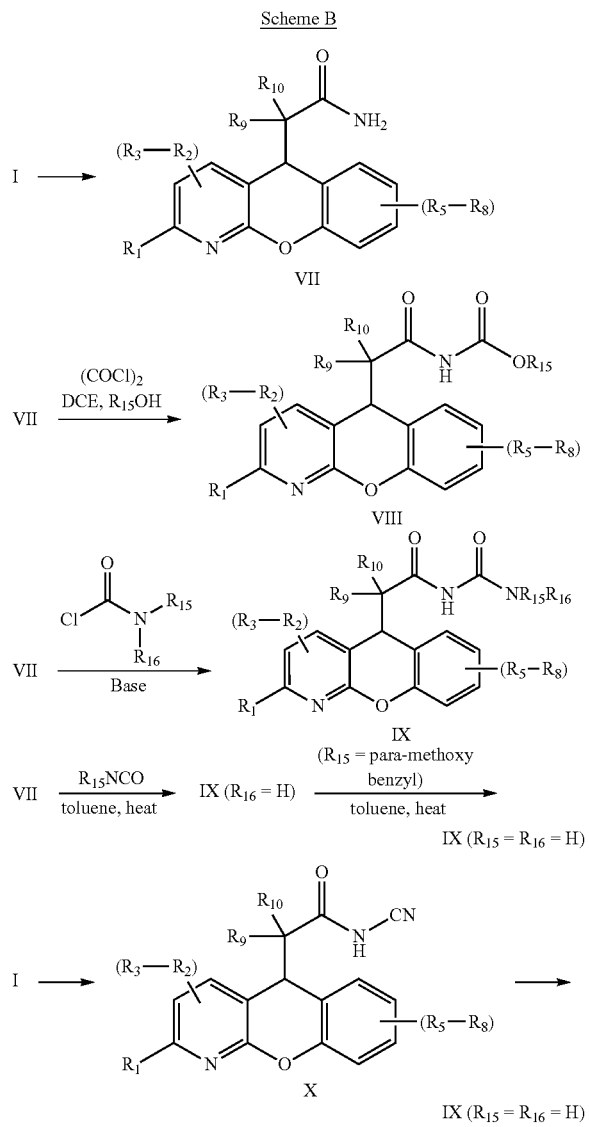

Acylurea and acylcarbamate compounds of the invention may be prepared as shown in Scheme B. Primary amides VII may be prepared from carboxylic acid I by any of a number of different methods of condensing carboxylic acids with ammonia sources to provide primary amides. For example, activation of the acid may be achieved with (O-(7-azabenzotriazol-1-yl)-N,N,N',N'-tetramethyluronium hexafluorophosphate (HATU) in the presence of a tertiary amine base such as diisopropylethyl amine in a polar aprotic solvent such as DMF followed by condensation with ammonium chloride to provide the primary carboxamide VII. Acyl carbamates (VIII) may be prepared in a manner similar to that described by Weikert et al. (*J. Med. Chem.,* 34(5):1630-1633 (1991)) and Deng et al. (*Tetrahedron Lett.,* 46:7993-7996 (2005)). Thus, activation of the primary amide VII with oxalyl chloride in a suitable solvent (such as dichloroethane or the like) followed by quenching with a suitable alcohol to give acyl carbamate VIII. Secondary or tertiary acylureas (IX, where at least one or $R_{15}$ or $R_{16}$ is not hydrogen) may be obtained from amide VII by condensation with a carbamoyl chloride in the presence of a base suitably strong enough to deprotonate the primary amide (e.g., sodium hexamethyldisilazide or the like). Alternatively, secondary acylureas (IX, $R_{16}$=H, $R_{15}$ is not hydrogen) may be prepared by condensation of amides VII with an isocyanate in an appropriately inert solvent (such as toluene), typically at elevated temperature. In cases where $R_{15}$ is a protecting group such as para-methoxy benzyl (PMB), the protecting group may be cleaved to provide primary acyl ureas (IX, where both $R_{15}$ and $R_{16}$ are hydrogen). Cleavage of the PMB protecting group may be effected under strongly acidic (e.g., exposure to trifluoroacetic acid) or oxidative (e.g., exposure to 2,3-dichloro-5,6-dicyano-1,4-benzoquinone) conditions, as described by Oikawa et al. (*Tetrahedron Lett.,* 25:5393 (1984)). Primary acylureas may also be prepared according to the method of Xiao et al. (*Tetrahedron Lett.,* 5843-5844 (2010)). Thus, conversion of carboxylic acid I to an activated ester (e.g., with BOP reagent in the presence of diisopropyl ethyl amine) and condensation with cyanamide provides acylcyanamide X. Acylcyanamide X may be hydrolyzed to primary acylureas IX ($R_{15}$ and $R_{16}$ are hydrogen) under strongly acidic conditions. Thus, treatment with 4N HCl in water and an appropriate organic co-solvent (such as 1,4-dioxane or the like) provides primary acylurea example compounds of the invention.

DEFINITIONS

The following are definitions of terms used in this specification and appended claims. The initial definition provided for a group or term herein applies to that group or term throughout the specification and claims, individually or as part of another group, unless otherwise indicated.

The term "alkyl" refers to straight or branched chain hydrocarbon groups having 1 to 12 carbon atoms, preferably 1 to 6 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy ($C_{0-2}$)alkyl or ($C_{0-2}$)hydroxyalkyl includes hydroxy, hydroxymethyl and hydroxyethyl.

The term "substituted alkyl" refers to an alkyl group as defined above having one, two, or three substituents selected from the group consisting of halo (e.g., trifluoromethyl), alkenyl, substituted alkenyl, alkynyl, nitro, cyano, oxo (=O), $OR_a$, $SR_a$, (=S), —$NR_aR_b$, —N(alkyl)$_3^+$, —$NR_aSO_2$, —$NR_aSO_2R_c$, —$SO_2R_c$—$SO_2NR_aR_b$, —$SO_2NR_aC$(=O)$R_b$, $SO_3H$, —PO(OH)$_2$, —OC(O)$R_a$, —C(=O)$R_a$, —CO$_2R_a$, —C(=O)$NR_aR_b$, —C(=O) ($C_{1-4}$alkylene)$NR_aR_b$, —C(=O)$NR_a$(SO$_2$)$R_b$, —CO$_2$($C_{1-4}$ alkylene)$NR_aR_b$, —$NR_aC$(=O)$R_b$, —$NR_aCO_2R_b$, —$NR_a$ ($C_{1-4}$alkylene)CO$_2R_b$, =N—OH, =N—O-alkyl, aryl, cycloalkyl, heterocyclo, and/or heteroaryl, wherein $R_a$ and $R_b$ are selected from hydrogen, alkyl, alkenyl, CO$_2$H, CO$_2$ (alkyl), $C_{3-7}$cycloalkyl, phenyl, benzyl, phenylethyl, naphthyl, a four- to seven-membered heterocyclo, or a five- to six-membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being selected from the group consisting of $(C_{1-6})$alkyl, $(C_{2-6})$alkenyl, hydroxy, halogen, cyano, nitro, =O (as valence allows), $CF_3$, $O(C_{1-6}$alkyl), $OCF_3$, $C(=O)H$, $C(=O)(C_{1-6}$alkyl), $CO_2H$, $CO_2(C_{1-6}$alkyl), $NHCO_2(C_{1-6}$alkyl), —$S(C_{1-6}$alkyl), —$NH_2$, $NH(C_{1-6}$alkyl), $N(C_{1-6}$alkyl$)_2$, $N(CH_3)_3^+$, $SO_2(C_{1-6}$alkyl), $C(=O)(C_{1-4}$alkylene)$NH_2$, $C(=O)(C_{1-4}$alkylene)NH(alkyl), $C(=O)(C_{1-4}$alkylene)$N(C_{1-4}$alkyl$)_2$, $C_{3-7}$cycloalkyl, phenyl, benzyl, phenylethyl, phenyloxy, benzyloxy, naphthyl, a four- to seven-membered heterocyclo or cycloalkyl, or a five- to six-membered heteroaryl. When a substituted alkyl is substituted with an aryl (including, for example, phenyl and naphthyl), heterocyclo, cycloalkyl, or heteroaryl group, said ringed systems are as defined below and thus may have zero, one, two, or three substituents, also as defined below.

One skilled in the field will understand that, when the designation "$CO_2$" is used herein, this is intended to refer to the group

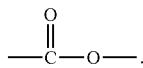

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl$(C_{0-4})$alkyl includes a substituted lower alkyl having at least one aryl substituent and also includes an aryl directly bonded to another group, i.e., aryl$(C_0)$alkyl.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., $\{-CH_2-\}_n$, wherein n is 1 to 12, preferably 1-8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substituents as defined above for substituted alkyl groups.

The term "heteroalkylene" is used herein to refer to saturated and unsaturated bivalent straight or branched chain hydrocarbon groups having 2 to 12 carbon atoms, preferably 2 to 8 carbon atoms, wherein one or two carbon atoms in the straight chain are replaced by heteroatom(s) selected from —O—, —S—, —S(=O)—, —SO_2—, —NH—, and —NHSO_2—. Thus, the term "heteroalkylene" includes bivalent alkoxy, thioalkyl, and aminoalkyl groups, as defined below, as well as alkylene and alkenylene groups having a combination of heteroatoms in the alkyl chain. As an illustration, a "heteroalkylene" herein may comprise groups such as —S—$(CH_2)_{1-5}$NH—$CH_2$—, —O—$(CH_2)_{1-5}$S(=O)—$CH_2$—, —$NHSO_2$—$CH_2$—, —$CH_2$—NH—, and so forth. Preferably, a heteroalkylene does not have two adjacent atoms simultaneously selected from —O— and —S—. When a subscript is used with the term heteroalkylene, e.g., as in $C_{2-3}$heteroalkylene, the subscript refers to the number of carbon atoms in the group in addition to heteroatoms. Thus, for example, a $C_{1-2}$heteroalkylene may include groups such as —NH—$CH_2$—, —$CH_2$—NH—$CH_2$—, —$CH_2$—$CH_2$—NH—, —S—$CH_2$—, —$CH_2$—S—$CH_2$—, —O—$CH_2$—NH—$CH_2$—, $CH_2$—O—$CH_2$ and so forth.

The term "substituted heteroalkylene" refers to a heteroalkylene group as defined above wherein at least one of the nitrogen or carbon atoms in the heteroalkylene chain is bonded to (or substituted with) a group other than hydrogen. Carbon atoms in the heteroalkylene chain may be substituted with a group selected from those recited above for substituted alkyl groups, or with a further alkyl or substituted alkyl group. Nitrogen atoms of the heteroalkylene chain may be substituted with a group selected from alkyl, alkenyl, alkynyl, cyano, or $A_1$-Q-$A_2$-$R_h$, wherein $A_1$ is a bond, $C_{1-2}$alkylene, or $C_{2-3}$alkenylene; Q is a bond, —C(=O)—, —C(=O)NR_d—, —C(=S)NR_d—, —SO_2—, —SO_2NR_d—, —CO_2—, or —NR_dCO_2—; $A_2$ is a bond, $C_{1-3}$alkylene, $C_{2-3}$alkenylene, —$C_{1-4}$alkylene-NR_d—, —$C_{1-4}$alkylene-NR_dC(=O)—, —$C_{1-4}$alkylene-S—, —$C_{1-4}$alkylene-SO_2—, or —$C_{1-4}$alkylene-O—, wherein said $A_2$ alkylene groups are branched or straight chain and optionally substituted as defined herein for substituted alkylene; $R_h$ is hydrogen, alkyl, substituted alkyl, alkenyl, substituted alkenyl, aryl, heteroaryl, heterocyclo, or cycloalkyl; and $R_d$ is selected from hydrogen, alkyl, and substituted alkyl, as defined herein, provided, however, that for a substituted heteroalkylene $R_h$ is not hydrogen when $A_1$, Q and $A_2$ are each bonds. When $R_h$ is aryl, heteroaryl, cycloalkyl, or heterocyclo, these rings are, in turn, optionally substituted with one to three groups as defined below in the definitions for these terms.

The term "alkoxy" refers to an oxygen atom substituted by alkyl or substituted alkyl, as defined herein. For example, the term "alkoxy" or includes the group —O—$C_{1-6}$alkyl.

The term "alkylthio" refers to a sulfur atom that is substituted by an alkyl or substituted alkyl group as defined herein. For example, the term "thioalkyl" includes the group —S—$C_{1-6}$alkyl, and so forth.

The term "alkylamino" refers to an amino group substituted with an alkyl group or substituted alkyl group as defined above. For example, the term "alkylamino" includes the group —NR—$C_{1-12}$alkyl (where R is preferably hydrogen but may include alkyl or substituted alkyl as defined above).

When a subscript is used with reference to an alkoxy, thioalkyl or aminoalkyl, the subscript refers to the number of carbon atoms that the group may contain in addition to heteroatoms. Thus, for example, monovalent $C_{1-2}$aminoalkyl includes the groups —$CH_2$—$N(CH_3)_2$, and —$(CH_2)_2$—$NH_2$. A lower aminoalkyl comprises an aminoalkyl having one to four carbon atoms. The term $(C_{1-4}$alkyl$)_{0-2}$amino includes the groups $NH_2$, —$NH(C_{1-4}$alkyl), and —$N(C_{1-4}$alkyl$)_2$. "Amino" used by itself refers to the group $NH_2$. A "substituted amino" refers to an amino group substituted as described above for the nitrogen atom of a heteroalkylene chain and includes, for example, the terms alkylamino and acylamino (—$NR_dC(O)R_e$). Where amino is designated as mono-substituted without further definition, the extra nitrogen valence is hydrogen. For example, the term "alkylaminocarbonyl(halo)$_{0-1}$aryl" describes a group of the general formula:

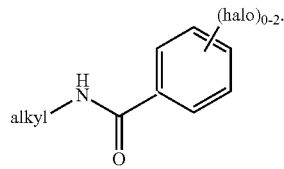

The alkoxy, thioalkyl, or aminoalkyl groups may be monovalent or bivalent. By "monovalent" it is meant that the group has a valency (i.e., ability to combine with another group), of one, and by "bivalent" it is meant that the group has a valency of two. Thus, for example, a monovalent alkoxy includes groups such as —O—C$_{1-12}$alkyl, whereas a bivalent alkoxy includes groups such as —O—C$_{1-12}$alkylene-.

It should be understood that the selections for all groups, including for examples, alkoxy, thioalkyl, and aminoalkyl, will be made by one skilled in the field to provide stable compounds. Thus, for example, in compounds of formula I, when G is attached to a nitrogen atom (N*) of ring A and is selected from an alkoxy or alkylthio group, the alkoxy and alkylthio groups will have at least one carbon atom bonded directly to ring A (at N*), with the oxygen or sulfur atoms being at least one atom away from said nitrogen atom.

The term "carbonyl" refers to a bivalent carbonyl group —C(=O)—. When the term "carbonyl" is used together with another group, such as in "heterocyclocarbonyl", this conjunction defines with more specificity at least one of the substituents that the substituted carbonyl will contain. For example, "heterocyclocarbonyl" refers to a carbonyl group as defined above where at least one of the substituents is a heterocyclo, such as morpholinyl.

The term "acyl" refers to a carbonyl group linked to an organic radical, more particularly, the group C(=O)R$_e$. The group R$_e$ can be selected from alkyl, alkenyl, alkynyl, aminoalkyl, substituted alkyl (i.e., substituted alkylene), substituted alkenyl, substituted alkynyl, cycloalkyl, heterocyclo, aryl, or heteroaryl, as defined herein. When R$_e$ is aryl, heteroaryl, cycloalkyl, or heterocyclo, these rings are, in turn, optionally substituted with one to three groups as defined below in the definitions for these terms.

The term "alkoxycarbonyl" refers to a carboxy group

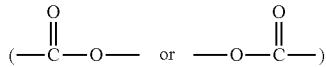

linked to an organic radical (CO$_2$R$_e$), as well as the bivalent groups —CO$_2$—, —CO$_2$R$_e$-which are linked to organic radicals in compounds of formula I, wherein R$_e$ is as defined above for acyl. The organic radical to which the carboxy group is attached may be monovalent (e.g., —CO$_2$-alkyl or —OC(=O)alkyl), or bivalent (e.g., —CO$_2$-alkylene, —OC(=O)alkylene, etc.) Accordingly, in compounds of formula I, when it is recited that G can be "alkoxycarbonyl", this is intended to encompass a selection for G of —CO$_2$— and also the groups —CO$_2$R$_e$— or —R$_e$CO$_2$—, wherein in this instance, the group R$_e$ will be selected from bivalent groups, e.g., alkylene, alkenylene, alkynylene, bivalent aminoalkyl, substituted alkylene, substituted alkenylene, or substituted alkynylene.

The term "sulfonyl" refers to a sulphoxide group (—S(O)$_2$—) linked to an organic radical in compounds of formula I, more particularly, the monovalent group —S(O)$_2$—R$_e$. Likewise, the term "sulfinyl" refers to a the group (—S(O)—) linked to an organic radical in compounds of formula I, more particularly, the monovalent group —S(O)—R$_e$. Additionally, the sulfonyl or sulfinyl group may be bivalent, in which case R$_e$ is a bond. The group R$_e$ is selected from those recited above for acyl and alkoxycarbonyl groups, with the exception that R$_e$ is not hydrogen.

The term "cycloalkyl" refers to fully saturated and partially unsaturated hydrocarbon rings (and therefore includes hydrocarbon rings also known as "cycloalkenyl rings") of 3 to 9, preferably 3 to 7 carbon atoms. The term "cycloalkyl" includes such rings having zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), OR$_a$, SR$_a$, (=S), —NR$_a$R$_b$, —N(alkyl)$_3^+$, —NR$_a$SO$_2$, —NR$_a$SO$_2$R$_c$, —SO$_2$R$_c$—SO$_2$NR$_a$R$_b$, —SO$_2$NR$_a$C(=O)R$_b$, SO$_3$H, —PO(OH)$_2$, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$ alkylene)NR$_a$R$_b$, —NR$_a$C(=O)R$_b$, —NR$_a$CO$_2$R$_b$, —NR$_a$(C$_{1-4}$ alkylene)CO$_2$R$_b$, =N—OH, =N—O-alkyl, aryl, cycloalkyl, heterocyclo, and/or heteroaryl, wherein R$_a$, R$_b$ and R$_c$ are as defined above for substituted alkyl groups, and are also in turn optionally substituted as recited above in the definition for substituted alkyl groups. The term "cycloalkyl" also includes such rings having a second ring fused thereto (e.g., including benzo, heterocyclo, or heteroaryl rings) or having a carbon-carbon bridge of 3 to 4 carbon atoms. When a cycloalkyl is substituted with a further ring (or has a second ring fused thereto), said ring in turn is optionally substituted with one to two of (C$_{1-4}$)alkyl, (C$_{2-4}$)alkenyl, (C$_{2-4}$)alkynyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3^+$, SO$_2$ (C$_{1-4}$alkyl), C(=O)(C$_{1-4}$alkylene)NH$_2$, C(=O)(C$_{1-4}$alkylene)NH(alkyl), C(=O)(C$_{1-4}$alkylene)N(C$_{1-4}$alkyl)$_2$ and/or phenyl optionally substituted with any of the preceding groups. As valence allows, if said further ring is cycloalkyl or heterocyclo it is additionally optionally substituted with =O (oxo).

Accordingly, in compounds of formula I, the term "cycloalkyl" includes cyclopropyl, cyclobutyl, cyclopentyl, cyclohexyl, cycloheptyl, bicyclooctyl, etc., as well as the following ring systems,

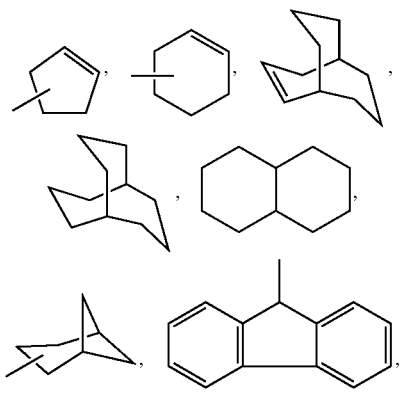

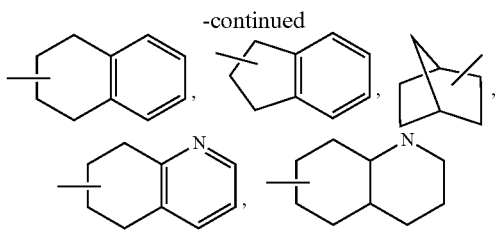

and the like, which optionally may be substituted at any available atoms of the ring(s). Preferred cycloalkyl groups include cyclopropyl, cyclopentyl, cyclohexyl, and

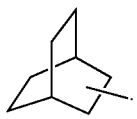

The term "halo" or "halogen" refers to chloro, bromo, fluoro and iodo.

The term "haloalkyl" means a substituted alkyl having one or more halo substituents. For example, "haloalkyl" includes mono-, bi-, and trifluoromethyl.

The term "haloalkoxy" means an alkoxy group having one or more halo substituents. For example, "haloalkoxy" includes $OCF_3$.

The term "aryl" refers to phenyl, biphenyl, fluorenyl, 1-naphthyl and 2-naphthyl. The term "aryl" includes such rings having zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), $SO_3H$, —$NR_aR_b$, —$N(alkyl)_3^+$, —$NR_aSO_2$, —$NR_aSO_2R_c$, —$SO_2R_c$, —$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_{1-4}alkylene)NR_aR_b$, —$C(=O)NR_a(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to two of $(C_{1-4})$alkyl, $(C_{2-4})$alkenyl, $(C_{2-4})$alkynyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, —$S(C_{1-4}alkyl)$, —$NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, $C(=O)(C_{1-4}alkylene)N(C_{1-4}alkyl)_2$ and/or phenyl optionally substituted with any of the preceding groups. As valence allows, if said further ring is cycloalkyl or heterocyclo it is additionally optionally substituted with =O (oxo).

Thus, examples of aryl groups include:

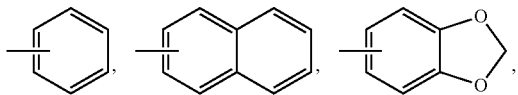

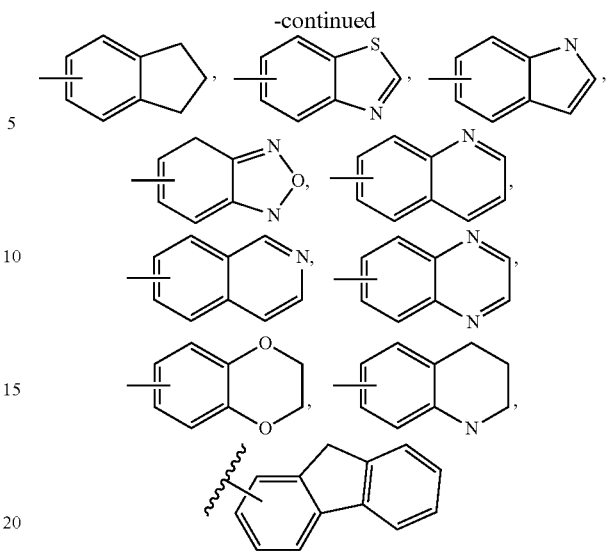

(fluorenyl) and the like, which optionally may be substituted at any available carbon or nitrogen atom. A preferred aryl group is optionally-substituted phenyl.

The terms "heterocycloalkyl", "heterocyclo" or "heterocyclic" may be used interchangeably and refer to substituted and unsubstituted non-aromatic 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom. The heterocyclo ring may contain zero, one, two or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), —$NR_aR_b$, —$N(alkyl)_3^+$, —$NR_aSO_2$, —$NR_aSO_2R_c$, —$SO_2R_c$—$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_{1-4}alkylene)NR_aR_b$, —$C(=O)NR_a(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above. When a heterocyclo is substituted with a further ring, said ring in turn is optionally substituted with one to two of $(C_{1-4})$alkyl, $(C_{2-4})$alkenyl, $(C_{2-4})$alkynyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, —$S(C_{1-4}alkyl)$, —$NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, $C(=O)(C_{1-4}alkylene)N(C_{1-4}alkyl)_2$ and/or phenyl optionally substituted with any of the preceding groups. As valence allows, if said further ring is cycloalkyl or heterocyclo it is additionally optionally substituted with =O (oxo).

Monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

Heterocyclo groups in compounds of formula I include

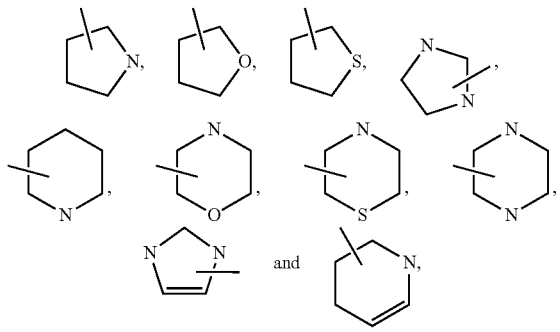

which optionally may be substituted.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (0, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), —$NR_aR_b$, —$N(alkyl)_3^+$, —$NR_aSO_2$, —$NR_aSO_2R_c$, —$SO_2R_c$—$SO_2NR_aR_b$, —$SO_2NR_aC(=O)R_b$, $SO_3H$, —PO(OH)$_2$, —$C(=O)R_a$, —$CO_2R_a$, —$C(=O)NR_aR_b$, —$C(=O)(C_{1-4}alkylene)NR_aR_b$, —$C(=O)NR_a(SO_2)R_b$, —$CO_2$ $(C_{1-4}$ alkylene)$NR_aR_b$, —$NR_aC(=O)R_b$, —$NR_aCO_2R_b$, —$NR_a(C_{1-4}alkylene)CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. When a heteroaryl is substituted with a further ring, said ring in turn is optionally substituted with one to two of $(C_{1-4})$alkyl, $(C_{2-4})$alkenyl, $(C_{2-4})$alkynyl, halogen, hydroxy, cyano, nitro, $CF_3$, $O(C_{1-4}alkyl)$, $OCF_3$, $C(=O)H$, $C(=O)(C_{1-4}alkyl)$, $CO_2H$, $CO_2(C_{1-4}alkyl)$, $NHCO_2(C_{1-4}alkyl)$, —$S(C_{1-4}alkyl)$, —$NH_2$, $NH(C_{1-4}alkyl)$, $N(C_{1-4}alkyl)_2$, $N(C_{1-4}alkyl)_3^+$, $SO_2(C_{1-4}alkyl)$, $C(=O)(C_{1-4}alkylene)NH_2$, $C(=O)(C_{1-4}alkylene)NH(alkyl)$, $C(=O)(C_{1-4}alkylene)N(C_{1-4}alkyl)_2$ and/or phenyl optionally substituted with any of the preceding groups. As valence allows, if said further ring is cycloalkyl or heterocyclo it is additionally optionally substituted with =O (oxo).

Monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of formula I, preferred heteroaryl groups include

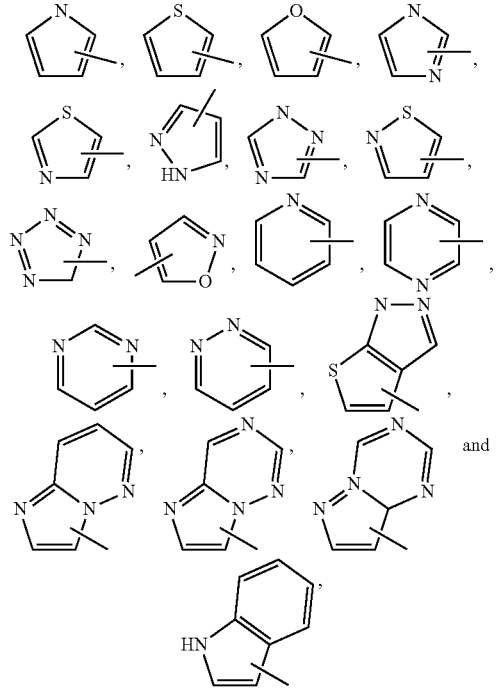

and the like, which optionally may be substituted at any available carbon or nitrogen atom. Aromatic rings may also be designated by an unbroken circle in the ring.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) unless otherwise specifically indicated the reference is intended to include rings having 0 to 3, preferably 0-2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

When the term "optionally substituted" is used herein to refer to a ring or group, the ring or group may be substituted or unsubstituted.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I can form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s)" may include zwitterions (inner salts), e.g., when a compound of formula I contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Prodrugs and solvates (e.g., hydrates) of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", *A Textbook of Drug Design and Development*, pp. 113-191, Krogsgaard-Larsen, P. et al., eds., Harwood Academic Publishers (1991); and c) Bundgaard, H., *Adv. Drug Deliv. Rev.*, 8:1-38 (1992); each of which is incorporated herein by reference.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans- and cis-isomers and may contain one or more chiral centers, therefore existing in enantiomeric and diastereomeric forms. The invention includes all such isomers, as well as mixtures of cis- and trans-isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers or diastereomers as starting materials. When enantiomeric or diastereomeric products are prepared, they can be separated by conventional methods for example, chromatographic or fractional crystallization.

Combinations

Where desired, the compounds of structure I may be used in combination with one or more other types of therapeutic agents such as immunosuppressants, anticancer agents, antiviral agents, anti-inflammatory agents, anti-fungal agents, antibiotics, anti-vascular hyperproliferation agents, anti-depressive agents, hypolipidemic agents or lipid-lowering agents or lipid modulating agents, antidiabetic agents, anti-obesity agents, antihypertensive agents, platelet aggregation inhibitors, and/or anti-osteoporosis agents, which may be administered orally in the same dosage form, in a separate oral dosage form or by injection.

The immunosuppressants which may be optionally employed in combination with compounds of formula I of the invention include cyclosporine, for example cyclosporin A, mycophenolate, interferon-beta, deoxyspergolin, FK-506 or Ant.-IL-2.

The anti-cancer agents which may be optionally employed in combination with compounds of formula I of the invention include azathiprine, 5-fluorouracil, cyclophosphamide, cisplatin, methotrexate, thiotepa, carboplatin, and the like.

The anti-viral agents which may be optionally employed in combination with compounds of formula I of the invention include abacavir, aciclovir, ganciclovir, zidanocin, vidarabine, and the like.

The anti-inflammatory agents which may be optionally employed in combination with compounds of formula I of the invention include non-steroidal anti-inflammatory drugs (NSAIDs) such as ibuprofen, cox-2 inhibitors such as celecoxib, rofecoxib, aspirin, naproxen, ketoprofen, diclofenac sodium, indomethacin, piroxicam, steroids such as prednisone, dexamethasone, hydrocortisone, triamcinolone diacetate, gold compounds, such as gold sodium thiomalate, TNF-α inhibitors such as tenidap, anti-TNF antibodies or soluble TNF receptor, and rapamycin (sirolimus or RAPAMUNE®) or derivatives thereof, infliximab (REMICADE®, Centocor, Inc.). CTLA-4Ig, LEA29Y, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins such as etanercept, fusion proteins constructed from CD40 and/or CD154gp39 (e.g., CD40Ig and CD8gp39), inhibitors, such as nuclear translocation inhibitors, of NF-kappa B function, such as deoxyspergualin (DSG).

The anti-fungal agents which may be optionally employed in combination with compounds of formula I of the invention include fluconazole, miconazole, amphotericin B, and the like.

The antibiotics which may be optionally employed in combination with compounds of formula I of the invention include penicillin, tetracycline, amoxicillin, ampicillin, erythromycin, doxycycline, vancomycin, minocycline, clindamycin or cefalexin.

The anti-vascular hyperproliferation agents which may be optionally employed with compounds of formula I of the invention include methotrexate, leflunomide, FK506 (tacrolimus, PROGRAF®).

The hypolipidemic agent or lipid-lowering agent or lipid modulating agents which may be optionally employed in combination with the compounds of formula I of the invention may include 1, 2, 3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na$^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. Nos. 5,595,872, 5,739,135, 5,712,279, 5,760,246, 5,827,875 and 5,885,983, and U.S. application Ser. No. 09/175,180, filed Oct. 20, 1998, now U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135, 5,712,279 and 5,760,246.

The most preferred MTP inhibitor is 9-[4-[4-[[2-(2,2,2-trifluoroethoxy)benzoyl]amino]-1-piperidinyl]butyl]-N-(2,2,2-trifluoroethyl)-9H-fluorene-9-carboxamide

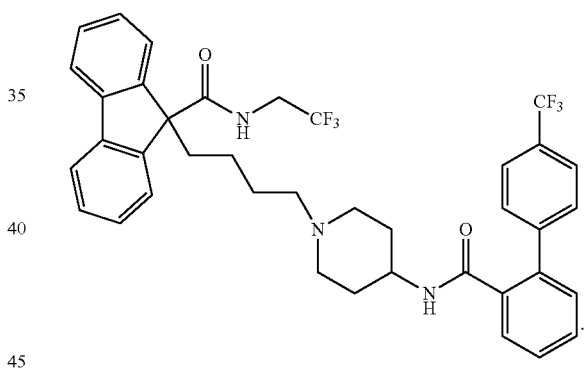

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0142146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al., *J. Med. Chem.*, 31(10):1869-1871 (1988), including isoprenoid (phosphinyl-methyl)phosphonates as well as other known squalene synthetase inhibitors, for example, as disclosed in U.S. Pat. Nos. 4,871,721 and 4,924,024 and in Biller, S. A. et al., *Current Pharmaceutical Design,* 2:1-40 (1996).

In addition, other squalene synthetase inhibitors suitable for use herein include the terpenoid pyrophosphates disclosed by Ortiz de Montellano, P. et al., *J. Med. Chem.*, 20:243-249 (1977), the farnesyl diphosphate analog A and presqualene pyrophosphate (PSQ-PP) analogs as disclosed by Corey et al., *J. Am. Chem. Soc.,* 98:1291-1293 (1976), phosphinylphosphonates reported by McClard, R. W. et al., *J. Am. Chem. Soc.,* 109:5544 (1987), and cyclopropanes reported by Capson, T. L., Ph.D., dissertation, Dept. Med. Chem., Univ. Utah, Abstract, Table of Contents, pp. 16, 17, 40-43, 48-51, Summary (June 1987).

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex, Policexide) and cholestagel (Sankyo/Geltex), as well as LIPOSTABIL® (Rhone-Poulenc), EISAI® E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277, 082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The hypolipidemic agent may be an ACAT inhibitor such as disclosed in *Drugs of the Future,* 24:9-15 (1999), (Avasimibe); Nicolosi et al., "The ACAT inhibitor, Cl-1011 is effective in the prevention and regression of aortic fatty streak area in hamsters", *Atherosclerosis* (Shannon, Irel)., 137(1):77-85 (1998), Ghiselli, G., "The pharmacological profile of FCE 27677: a novel ACAT inhibitor with potent hypolipidemic activity mediated by selective suppression of the hepatic secretion of ApoB 100-containing lipoprotein", *Cardiovasc. Drug Rev.,* 16(1):16-30 (1998); Smith, C. et al., "RP 73163: a bioavailable alkylsulfinyl-diphenylimidazole ACAT inhibitor", *Bioorg. Med. Chem. Lett.,* 6(1):47-50 (1996); Krause, B. R. et al., Chapter 6: "ACAT Inhibitors: Physiologic Mechanisms for Hypolipidemic and Anti-Atherosclerotic Activities in Experimental Animals", *Inflammation: Mediators and Pathways,* pp. 173-198, Ruffolo, Jr., R. R. et al., eds., CRC Press, Inc. (1995); Sliskovic et al., "ACAT inhibitors: potential anti-atherosclerotic agents", *Curr. Med. Chem.,* 1(3):204-225 (1994); Stout, D. M., "Inhibitors of Acyl-CoA: Cholesterol O-Acyl Transferase (ACAT) as Hypocholesterolemic Agents. 6. The First Water-Soluble ACAT Inhibitor with Lipid-Regulating Activity Inhibitors of Acyl-CoA:Cholesterol Acyltransferase (ACAT). 7. Development of a Series of Substituted N-Phenyl-Y-[(1-phenylcyclopentyl)-methyl]ureas with Enhanced Hypocholestrolemic Activity", *Chemtracts-Organic Chemistry,* 8:359-362 (1995), or TS-962 (acetamide, N-[2,6-bis (1-methylethyl)phenyl]-2-(tetradecylthio)-) (Taisho Pharmaceutical Co. Ltd).

The hypolipidemic agent may be an upregulator of LD2 receptor activity such as MD-700 (1(3H)-isobenzofuranone, 3-(13-hydroxy-10-oxotetradecyl)-5,7-dimethoxy) (Taisho Pharmaceutical Co. Ltd.) and LY295427 (cholestan-3-ol, 4-(2-propenyl)-, (3a,4a,5a)-) (Eli Lilly).

The hypolipidemic agent may be a cholesterol absorption inhibitor preferably Schering-Plough's ezetimibe (SCH58235) and SCH48461 as well as those disclosed in *Atherosclerosis,* 115:45-63 (1995) and *J. Med. Chem.,* 41:973 (1998).

The hypolipidemic agent may be an ileal Na$^+$/bile acid cotransporter inhibitor such as disclosed in *Drugs of the Future,* 24:425-430 (1999).

The lipid-modulating agent may be a cholesteryl ester transfer protein (CETP) inhibitor such as Pfizer's CP 529, 414 (torcetrapib) (WO 00/38722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD-4522.

The above-mentioned U.S. patents are incorporated herein by reference. The amounts and dosages employed will be as indicated in the *Physicians' Desk Reference* and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the *Physicians' Desk Reference.*

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the *Physicians' Desk Reference*, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al., "Attenuation of diet-induced atherosclerosis in rabbits with a highly selective 15-lipoxygenase inhibitor lacking significant antioxidant properties", *Brit. J. Pharmacol.*, 120:1199-1206 (1997), and Cornicelli et al., "15-Lipoxygenase and its Inhibition: A Novel Therapeutic Target for Vascular Disease", *Current Pharmaceutical Design*, 5:11-20 (1999).

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of formula I may be 1, 2, 3 or more antidiabetic agents or antihyperglycemic agents including insulin secretagogues or insulin sensitizers, or other antidiabetic agents preferably having a mechanism of action different from the compounds of formula I of the invention, which may include biguanides, sulfonyl ureas, glucosidase inhibitors, PPAR γ agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Wellcome's GL-262570 (farglitazar), englitazone (CP-68722, Pfizer) or darglitazone (CP-86325, Pfizer, isaglitazone (MIT/J&J), JTT-501 (reglitazar) (JPNT/P&U), L-895645 (Merck), R-119702 (rivoglitazone) (Sankyo/WL), NN-2344 (balaglitazone) (Dr. Reddy/NN), or YM-440 ((Z)-1,4-bis-4-[(3,5-dioxo-1,2,4-oxadiazolidin-2-yl-methyl)]-phenoxybut-2-ene) (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (exenatide) (Amylin) and LY-315902 (8-37-glucagon-like peptide I (human), N-[3-(1H-imidazol-4-yl)-1-oxopropyl]-26-L-arginine-34-[N6-(1-oxooctyl)-L-lysine]-) (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the *Physicians' Desk Reference* (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the *Physicians' Desk Reference*.

Where present GLP-1 peptides may be administered in oral buccal formulations, by nasal administration or parenterally as described in U.S. Pat. No. 5,346,701 (TheraTech), U.S. Pat. Nos. 5,614,492 and 5,631,224 which are incorporated herein by reference.

The other antidiabetic agent may also be a PPAR α/γ dual agonist such as AR-HO39242 (tesaglitazar) (Astra/Zeneca), GW-409544 (Glaxo-Wellcome), KRP297 (benzamide, 5-[(2,4-dioxo-5-thiazolidinyl)methyl]-2-methoxy-N-[[4-(trifluoromethyl)phenyl]methyl]-(Kyorin Merck) as well as those disclosed by Murakami et al., "A Novel Insulin Sensitizer Acts As a Coligand for Peroxisome Proliferation-Activated Receptor Alpha (PPAR alpha) and PPAR gamma. Effect on PPAR alpha Activation on Abnormal Lipid Metabolism in Liver of Zucker Fatty Rats", *Diabetes*, 47:1841-1847 (1998).

The antidiabetic agent may be an SGLT2 inhibitor such as disclosed in U.S. application Ser. No. 09/679,027, filed Oct. 4, 2000, employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000, employing dosages as set out herein. Preferred are the compounds designated as preferred in the above application.

The antidiabetic agent may be a DP4 inhibitor such as disclosed in U.S. application Ser. No. 09/788,173, filed Feb. 16, 2001, WO 99/38501, WO 99/46272, WO 99/67279 (PROBIODRUG), WO 99/67278 (PROBIODRUG), WO 99/61431 (PROBIODRUG), saxagliptin (preferred), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al., *Biochemistry*, 38(36): 11597-11603 (1999), TSL-225 (tryptophyl-1,2,3,4-tetrahydro-isoquinoline-3-carboxylic acid (disclosed by Yamada et al., *Bioorg. Med. Chem. Lett.*, 8:1537-1540 (1998), 2-cyanopyrrolidides and 4-cyanopyrrolidides as disclosed by Ashworth et al., *Bioorg. Med. Chem. Lett.*, 6(22): 1163-1166 and 2745-2748 (1996) employing dosages as set out in the above references.

The meglitinide which may optionally be employed in combination with the compound of formula I of the invention may be repaglinide, nateglinide (Novartis) or KAD1229 (mitiglinide) (PF/Kissei), with repaglinide being preferred.

The compound of formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of formula I may be AJ9677 (rafabegron) (Takeda/Dainippon), L750355 (benezenesulfonamide, N-[4-[2-[[(2S)-3-[(6-amino-3-pyridinyl)oxy]-2-hydroxypropyl]amino]ethyl]phenyl]-4-(1-methylethyl)-) (Merck), or CP331684 (4-[2-[[2-(6-aminopyridin-3-yl)-2(R)-hydroxyethyl]-amino]ethoxy]phenyl] acetic acid) (Pfizer) or other known beta 3 agonists as disclosed in U.S. Pat. Nos. 5,541,204, 5,770,615, 5,491,134, 5,776,983 and 5,488,064, with AJ9677, L750,355 (benzenesulfonamide, N-[4-[2-[[(2S)-3-[(6-amino-3-pyridinyl)oxy]-2-hydroxypropyl]amino]ethyl]phenyl]-4-(1-methylethyl)-) and CP331684 being preferred.

The lipase inhibitor which may be optionally employed in combination with a compound of formula I may be orlistat or ATL-962 (Alizyme), with orlistat being preferred.

The serotonin (and dopamine) reuptake inhibitor which may be optionally employed in combination with a compound of formula I may be sibutramine, topiramate (Johnson & Johnson) or AXOKINE® (Regeneron), with sibutramine and topiramate being preferred.

The thyroid receptor agonist which may be optionally employed in combination with a compound of formula I may be a thyroid receptor ligand as disclosed in WO 97/21993 (U. Cal SF), WO 99/00353 (KaroBio), WO 00/039077 (KaroBio), and U.S. Provisional Application Ser. No. 60/183,223, filed Feb. 17, 2000, with compounds of the KaroBio applications and the above U.S. provisional application being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

The antihypertensive agents which may be employed in combination with the compound of formula I of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al. mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in *Clin. Exp. Pharmacol. Physiol.*, 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in *Chemical Abstracts,* 102:72588v, and *Jpn. J. Pharmacol.,* 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in *Eur. Ther. Res.,* 39:671 (1986); 40:543 (1986); ramipril (Hoechst) disclosed in European Patent No. 79-022 and *Curr. Ther. Res.,* 40:74 (1986); Ru 44570 (Hoechst) disclosed in *Arzneimittelforschung,* 34:1254 (1985), cilazapril (Hoffman-LaRoche) disclosed in *J. Cardiovasc. Pharmacol.,* 9:39 (1987); R 31-2201 (Hoffman-LaRoche) disclosed in *FEBS Lett.,* 165:201 (1984); lisinopril (Merck), indalapril (delapril) disclosed in U.S. Pat. No. 4,385,051; indolapril (Schering) disclosed in *J. Cardiovasc. Pharmacol.,* 5:643, 655 (1983), spirapril (Schering) disclosed in *Acta Pharmacol. Toxicol.,* 59(Supp. 5):173 (1986); perindopril (Servier) disclosed in *Eur. J. Clin. Pharmacol.,* 31:519 (1987); quinapril (Warner-Lambert) disclosed in U.S. Pat. No. 4,344,949 and CI925 (Warner-Lambert) ([3S-[2[R(*)R(*)]]3R(*)]-2-[2-[[1-(ethoxy-carbonyl)-3-phenyl-propyl]amino]-1-oxopropyl]-1,2,3,4-tetrahydro-6,7-dimethoxy-3-isoquinolinecarboxylic acid HCl) disclosed in *Pharmacologist,* 26:243, 266 (1984), WY-44221 (Wyeth) disclosed in *J. Med. Chem.,* 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, 5,552,397, 5,504,080, 5,612,359 and 5,525,723, European Patent Application Nos. 0599444, 0481522, 0599444, 0595610, 0534363 A2, 534396, 534492 and 0629627 A2.

Preferred are those NEP/ACE inhibitors and dosages thereof which are designated as preferred in the above patents/applications which U.S. patents are incorporated herein by reference; most preferred are omapatrilat, BMS-189921 ([S—(R*,R*)]-hexahydro-6-[(2-mercapto-1-oxo-3-phenylpropyl)amino]-2,2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from about 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the *Physicians' Desk Reference* (PDR).

Other examples of preferred antihypertensive agents suitable for use herein include omapatrilat (Vanlev) amlodipine besylate (NORVASC®), prazosin HCl (MINIPRESS®), verapamil, nifedipine, nadolol, diltiazem, felodipine, nisoldipine, isradipine, nicardipine, atenolol, carvedilol, sotalol, terazosin, doxazosin, propranolol, and clonidine HCl (CATAPRES®).

Diuretics which may be employed in combination with compounds of formula I include hydrochlorothiazide, torasemide, furosemide, spironolactono, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula I of the invention include parathyroid hormone or bisphosphonates, such as MK-217 (alendronate) (FOSAMAX®).

Dosages employed for the above drugs will be as set out in the *Physicians' Desk Reference.*

PHARMACEUTICAL FORMULATIONS

The pharmaceutical composition of the invention includes a pharmaceutically acceptable carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-to-copherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the modulators of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the invention may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds of the invention may, for example, be administered in a form suitable for immediate release or extended release. Immediate release or extended release may be achieved by the use of suitable pharmaceutical compositions including the compounds of the invention, or, particularly in the case of extended release, by the use of devices such as subcutaneous implants or osmotic pumps. The compounds of the invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the compound(s) of the invention with fast dissolving diluents such as mannitol, lactose, sucrose and/or cyclodextrins. Also included in such formulations may be high molecular weight excipients such as celluloses (AVICEL®) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human from about 0.1 to 500 mg/kg of body weight of active compound per day, or between 0.5 and 2000 mg per day which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The compounds of formula I of the invention are glucocorticoid receptor modulators as shown either by their ability to bind glucocorticoid receptors in GR binding assays, or by their ability to inhibit AP-1 activity as indicated in cellular transrespressional assays, and cause none to minimal transactivation as indicated in cellular transcriptional assays.

Compounds of the invention, including the compounds described in the examples hereof, have been tested in at least one of the assay(s) described below and have glucocorticoid receptor (GR)/Dexamethasone (Dex) inhibition activity (>25% at 10 µM) and/or AP-1 inhibition activity ($EC_{50}$ less than 15 µM).

Identical and/or similar assays are described in U.S. application Ser. No. 10/621,807, filed Jul. 17, 2003 which is incorporated in its entirety herein by reference.

GR Binding Assays

Glucocorticoid Receptor Binding Assay (I)

In order to assess the affinity of test compounds for the human glucocorticoid receptor, a commercially available kit was used (Glucocorticoid Receptor Competitor Assay Kit, Invitrogen Part #2893). Briefly, purified human recombinant full-length glucocorticoid receptor (2 nM) was mixed with fluorescently labeled glucocorticoid (1 nM Fluormone GS Red) in the presence or absence of test compound. After two hour incubation at room temperature in the dark, the fluorescence polarization (FP) of the samples was measured. The FP of a mixture of receptor, fluorescent probe (i.e., Fluormone GS Red) and 5 µM dexamethasone represented background fluorescence or 100% inhibition, whereas, the FP of the mixture without dexamethasone (but in the presence of vehicle) was taken to be 100% binding. The percentage inhibition of test compounds were then compared to the sample with 5 µM dexamethasone and expressed as % relative binding activity with dexamethasone being 100% and no inhibition is 0%. Test compounds were analyzed in the concentration range from 8.5E-05 µM to 5 µM.

Glucocorticoid Receptor Binding Assay (II)

In order to measure the binding of compounds on the glucocorticoid receptor a commercially available kit was used (Glucocorticoid receptor competitor assay kit, PanVera Co., Madison, Wis., P2816). Briefly, a cell lysate containing recombinantly expressed human full-length glucocorticoid receptor was mixed with a fluorescently labeled glucocorticoid (1 nM Fluormone GS1) in the presence or absence of test compound. After one hour at room temperature, the fluorescence polarization (FP) of the samples were measured. The FP of a mixture of receptor, fluorescent probe (i.e., Fluormone GS1) and 1 mM dexamethasone represented background fluorescence or 100% inhibition, whereas, the FP of the mixture without dexamethasone was taken to be 100% binding. The percentage inhibition of test molecules were then compared to the sample with 1 mM dexamethasone and expressed as % relative binding activity with dexamethasone being 100% and no inhibition is 0%. Test molecules were analyzed in the concentration range from 2.4 nM to 40 µM.

Site I binding assays for any NHR (Nuclear Hormone Receptor) are conducted similarly to the above. An appropriate cell lysate or purified NHR is used as the source of the NHR. The fluorescent probe and unlabeled competitor are appropriate for the specific NHR, i.e., are ligands for the specific NHR.

Cellular Transrepressional Assay

To measure the ability of test molecules to inhibit AP-1 induced transcriptional activity we utilized an A549 cell which was stably transfected with a plasmid containing 7×AP-1 DNA binding sites (pAP-1-Luc plasmid, Stratagene Co., La Jolla, Calif.) followed by the gene for luciferase. Cells were activated with 10 ng/ml of phorbol myristic acid (PMA) plus or minus test molecules for 7 hours. After 7 hours a luciferase reagent was added to measure luciferase enzymatic activity in the cell. After a 10 minute incubation of luciferase reagent with cells, luminescence was measured in a TOPCOUNT® luminescence counter. Repression of AP-1 activity was calculated as the percentage decrease in the signal induced by PMA alone. Test molecules were analyzed in the concentration range from 0.1 nM to 40 µM. $EC_{50}$s were determined by using standard curve fitting methods such as Excel fit (Microsoft Co.). An $EC_{50}$ is the test molecule concentration at which there is a 50% repression of the maximal inhibition of transcription, i.e., a 50% reduction of AP-1 activity.

Other reporters and cell lines also may be used in a cellular transrepressional assay. A similar assay is performed in which NF-κB activity is measured. A plasmid containing NF-κB DNA binding sites is used, such as pNF-κB-Luc, (Stratagene, LaJolla, Calif.), and PMA or another stimulus, such as TNF-α or lipopolysaccharide, is used to activate the NF-κB pathway. NF-κB assays similar to that described in Yamamoto K. et al., *J. Biol. Chem.*, 270(52):31315-31320 (Dec. 29, 1995) may be used.

The cellular transrepressional assays described above may be used to measure transrepression by any NHR. One of skill in the art will understand that assays may require the addition of components, such as a stimulus (e.g., PMA, lipopolysaccharide, TNF-α, etc) which will induce transcription mediated by AP-1 or NF-κB.

Additionally, AR mediated transrepression may be measured by the assay described in Palvimo, J. J. et al., *J. Biol. Chem.*, 271(39):24151-24156 (Sep. 27, 1996), and PR mediated transrepression may be measured by the assay described in Kalkhoven, E. et al., *J. Biol. Chem.*, 271(11): 6217-6224 (Mar. 15, 1996).

Examples of compounds of the present invention prepared by methods described in the general schemes are given in the preparations and examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diaststereoselectivity of transformations, providing enantio-enriched products upon cleavage of the chiral auxiliary.

EXAMPLES

The following Examples illustrate embodiments of the inventive compounds and starting materials, and are not intended to limit the scope of the claims. For ease of reference, the following abbreviations are used herein:

Abbreviations $AlCl_3$=aluminum chloride
$Ac_2O$=acetic anhydride
AcONa=sodium acetate
bp=boiling point
$CH_3CN$=acetonitrile
DCC=dicyclohexylcarbodiimide
DCE=dichloroethane
DCM=dichloromethane
DMAP=4-dimethylaminopyridine
DIPEA or DIEA=N,N-diisopropylethylamine
DME=1,2-dimethoxyethane
DMF=dimethyl formamide
EDCI=1-3-dimethylaminopropyl)-3-ethylcarbodiimide
$Et_2O$=diethyl ether
HOBT=1-hydroxybenzotriazole
EtOAc=ethyl acetate
EtOH=ethanol
g=gram(s)
HCl=hydrochloric acid
KOH=potassium hydroxide
$K_2CO_3$=potassium carbonate
l=liter
$LiAlH_4$=lithium aluminum hydride
MeCN=acetonitrile
MeOH=methanol
$MgSO_4$=magnesium sulfate
NaH=sodium hydride
$Na_2SO_4$=sodium sulfate NaOH=sodium hydroxide
NMP=1-methyl-2-pyrrolidinone
PBr$_3$=phosphorus tribromide
(Ph$_3$P)$_4$Pd=tetrakis(triphenylphosphine)palladium(0)
PS=polystyrene
SOCl$_2$=thionyl chloride
TEA=triethylamine
mg=milligram(s)
ml=milliliter
μl=microliter
mmol=millimole
μmol=micromole
mol=mole
mp=melting point
RT=room temperature The preparations set out below are for the synthesis of reagents that were not obtained from commercial sources and were employed for the preparation of compounds of formula I of the invention.

Reverse-phase preparative high performance liquid chromatography ("HPLC") was performed with Shimadzu 8A liquid chromatographs using YMC S5 ODS columns (20×100, 20×250, or 30×250 millimeter ("mm")). Gradient elution was performed with methanol ("MeOH")/water mixtures in the presence of 0.1% trifluoroacetic acid ("TFA").

Analytical HPLC Method Employed in Characterization of Examples

Analytical HPLC was performed on Shimadzu LC10AS liquid chromatographs using the following methods:
Method 1 (used in all cases, unless otherwise indicated):
Linear gradient of 0 to 100% Mobile Phase B over 4 minutes ("min"), with 1 minute ("min") hold at 100% B.
Ultraviolet ("UV") visualization at 220 nanometers ("nm")
Column: YMC S5 ODS 4.6×50 mm
Flow rate: 4 milliliters ("mL")/min
Mobile Phase A: 0.2% phosphoric acid, 90% water, 10% methanol
Mobile Phase B: 0.2% phosphoric acid, 90% methanol, 10% water
Method 2:
Linear gradient of 10 to 100% Mobile Phase B over 12 min, with 3 min hold at 100% B.
Ultraviolet ("UV") visualization at 220 nm and 254 nm
Column: SunFire C18 4.6×150 mm, 3.5μ
Flow rate: 1 mL/min
Mobile Phase A: 0.05% TFA in water:acetonitrile (95:5)
Mobile Phase B: 0.05% TFA in water:acetonitrile (5:95)
Method 3:
Linear gradient of 10 to 100% Mobile Phase B over 12 min, with 3 min hold at 100% B.
Ultraviolet ("UV") visualization at 220 nm and 254 nm
Column: XBridge Phenyl 4.6×150 mm, 3.5μ, SC 863
Flow rate: 1 mL/min
Buffer: 0.05% TFA in water
Mobile Phase A: Buffer:acetonitrile (95:5)
Mobile Phase B: Buffer:acetonitrile (5:95)
Method 4:
Linear gradient of 10 to 100% Mobile Phase B over 25 min, with 5 min hold at 100% B.
Ultraviolet ("UV") visualization at 220 nm and 254 nm
Column: XBridge Phenyl 4.6×150 mm, 3.5μ, SC 863
Flow rate: 1 mL/min
Buffer: 0.05% TFA in water
Mobile Phase A: Buffer:acetonitrile (95:5)
Mobile Phase B: Buffer:acetonitrile (5:95)
Method 5:
Linear gradient of 10 to 100% Mobile Phase B over 25 min, with 5 min hold at 100% B.
Ultraviolet ("UV") visualization at 220 nm and 254 nm
Column: SunFire C18 4.6×150 mm, 3.5μ
Flow rate: 1 mL/min
Mobile Phase A: 0.05% TFA in water:acetonitrile (95:5)
Mobile Phase B: 0.05% TFA in water:acetonitrile (5:95)
Method 6:
Linear gradient of 0 to 100% Mobile Phase B over 12 minutes ("min"), with 8 minute ("min") hold at 100% B.
Ultraviolet ("UV") visualization at 220 nanometers ("nm") and 254 nm.
Column: XBridge Phenyl 4.6×150 mm, 3.5μ
Flow rate: 1 milliliters ("mL")/min
Mobile Phase A: 10 MM NH$_4$HCO$_3$ in water pH: 9.5 adjusted using diluted ammonia.
Mobile Phase B: Methanol 100%

Analytical LCMS Methods 7 to 9 were performed on Agilent Technologies 6140 quadrupole LC/MS as described below:
Method 7:
Linear gradient of 0 to 100% Mobile Phase B over 2 minutes ("min").
Ultraviolet ("UV") visualization at 220 nanometers ("nm") and 254 nm.
Column: ZORBAX® SB C18 (4.6×50) mm, 5 μm
Flow rate: 5 milliliters ("mL")/min
Mobile Phase A: 0.1% TFA in methanol:water (10:90)
Mobile Phase B: 0.1% TFA in methanol:water (90:10)
Method 8:
Linear gradient of 0 to 100% Mobile Phase B over 2 minutes ("min"), with 0.5 minute ("min") hold at 100% B.
Ultraviolet ("UV") visualization at 220 nm and 254 nm
Column: PUROSPHER® Star RP-18 (4×55) mm, 3 μm
Flow rate: 2.5 mL/min
Mobile Phase A: 20 MM NH$_4$OAc in water:acetonitrile (90:10)
Mobile Phase B: 20 MM NH$_4$OAc in water:acetonitrile (10:90)
Method 9:
Linear gradient of 0 to 100% Mobile Phase B over 1.5 minutes ("min"), with 1.7 minute ("min") hold at 100% B.
Ultraviolet ("UV") visualization at 220 nm and 254 nm
Column: Ascentis Express C18 (2.1×50) mm, 2.7 μm
Flow rate: 1 mL/min
Mobile Phase A: 10 MM Ammonium formate in water:acetonitrile (98:02)
Mobile Phase B: 10 MM Ammonium formate in water:acetonitrile (98:02)

Preparation 1

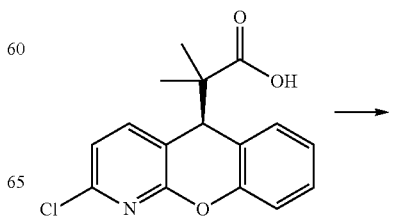

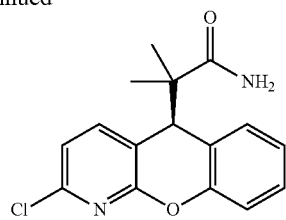

To a solution of (S)-2-(2-chloro-5H-chromeno[2,3-b]pyridine-5-yl)-2-methylpropanoic acid (500 mg, 1.65 mmol) in anhydrous DMF (5 mL) was added ammonium carbonate (475 mg, 4.95 mmol), EDCI hydrochloride (630 mg, 3.30 mmol), 1-hydroxy benzotriazole (445 mg, 3.30 mmol) and N,N-diisopropylethylamine (1.06 mL, 5.77 mmol). The reaction mixture was stirred at room temperature for overnight. Then the reaction mixture was concentrated and partitioned between water and EtOAc. The organic layer was washed with brine, dried over sodium sulfate and concentrated to provide the product (480 mg, 98% yield) as a white solid. MS (E+) m/z: 303 (M+H); LCMS retention time: 1.41 min (Method 9).

Preparation 2

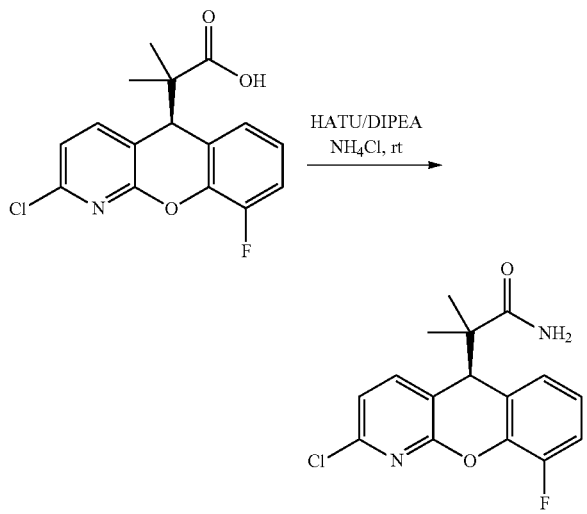

To a solution of (S)-2-(2-chloro-9-fluoro-5H-chromeno [2,3-b]pyridin-5-yl)-2-methylpropanoic acid (500 mg, 1.554 mmol) (prepared as described in WO 2008/021926) in DMF (5 mL) was added HATU (709 mg, 1.865 mmol), DIEA (0.814 mL, 4.66 mmol), and ammonium chloride (249 mg, 4.66 mmol). The resulting mixture was heated to 80° C. and kept stirring for 12 h. Saturated aqueous sodium bicarbonate was added to the reaction mixture, which was then extracted with ethyl acetate. The organic layer was dried over sodium sulfate and concentrated, then purified by flash column chromatography (40 g silica gel, 10% MeOH/dichloromethane) to give the product (416 mg, 84% yield) as a white solid. MS (E+) m/z: 346.1 (M+H); LC retention time: 2.90 min.

Preparation 3

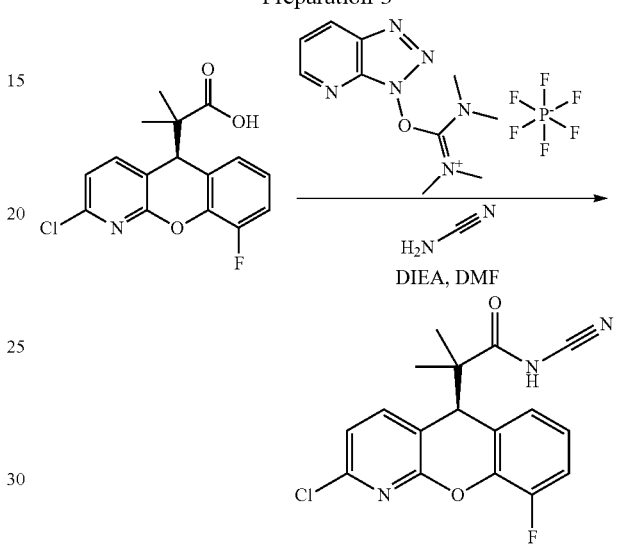

To a solution of (S)-2-(2-chloro-9-fluoro-5H-chromeno [2,3-b]pyridin-5-yl)-2-methylpropanoic acid (300 mg, 0.932 mmol) (prepared as described in WO 2008/021926) in DMF (3 mL) was added HATU (425 mg, 1.12 mmol), DIEA (0.489 mL, 2.80 mmol), and cyanamide (78 mg, 1.865 mmol). The resulting mixture was stirred at room temperature for 12 h. Saturated aqueous sodium bicarbonate was added to the reaction mixture, which was then extracted with ethyl acetate. The organic layer was dried over sodium sulfate and concentrated, then purified by flash column chromatography (40 g silica gel, 10% MeOH/dichloromethane) to give the product (276 mg, 86% yield) as a white solid. MS (E+) m/z: 321 (M+H); LC retention time: 2.57 min. $^1$H NMR (400 MHz, MeOD) δ ppm 7.68 (1H, d), 7.25 (1H, d, J=7.9 Hz), 7.06-7.19 (2H, m), 6.99 (1H, d, J=7.5 Hz), 4.39 (1H, s), 0.93 (6H, s).

Preparation 4

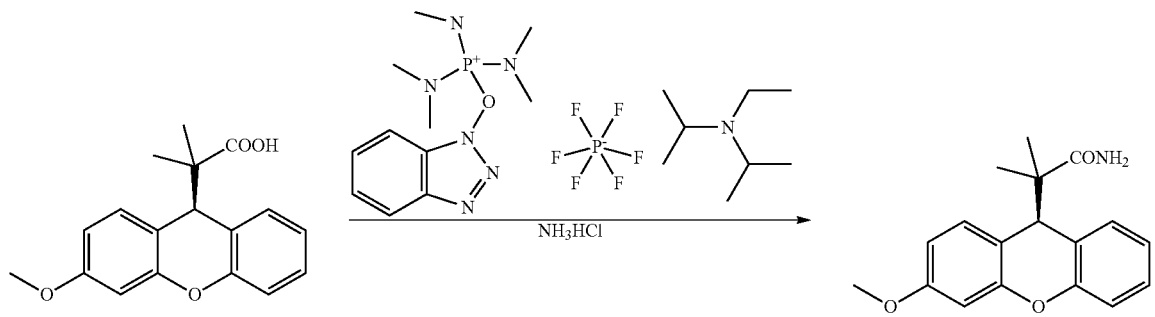

To a solution of (S)-2-(3-methoxy-9H-xanthen-9-yl)-2-methylpropanoic acid (30 mg, 0.101 mmol) (prepared as described in WO 2008/021926) in DMF (1 mL) was added DIEA (0.053 mL, 0.302 mmol), BOP (66.7 mg, 0.151 mmol) and ammonium chloride (16.14 mg, 0.302 mmol). The resulting mixture was stirred at room temperature for 12 h, then purified by preparative HPLC to provide the product (20 mg, 67% yield) as a white solid. LC retention time: 3.15 min.

Preparation 5

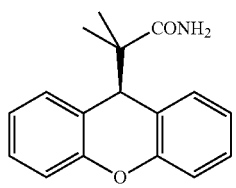

9H-Xanthen-9-yl)-2-methylpropanoic acid was prepared as described in WO 2008/021926. The product of Preparation Am was prepared in a manner similar to the preparation of the product of Preparation A1. LC retention time: 3.17 min.

Preparation 6

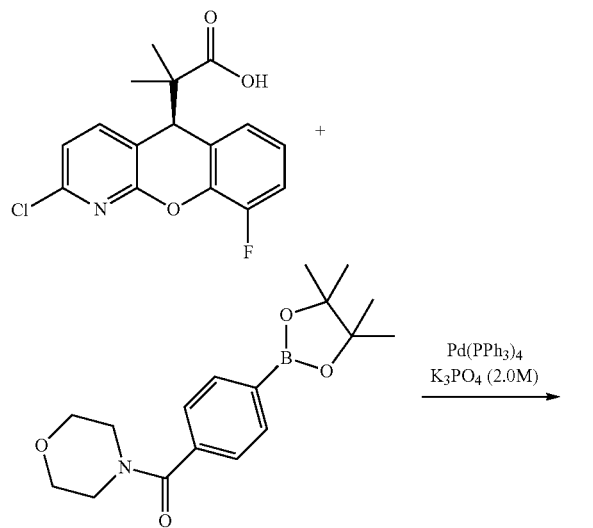

To a solution of (S)-2-(2-chloro-9-fluoro-5H-chromeno[2,3-b]pyridin-5-yl)-2-methylpropanoic acid (prepared as described in WO 2008/021926) (500 mg, 1.554 mmol) in DMF (5 ml) was added morpholino(4-(4,4,5,5-tetramethyl-1,3,2-dioxaborolan-2-yl)phenyl)methanone (986 mg, 3.11 mmol) and potassium phosphate tribasic monohydrate (2.331 ml, 4.66 mmol). Argon was bubbled through the mixture for 10 min. Palladium tetrakis (90 mg, 0.078 mmol) was then added. Argon was bubbled through for another 5 min. The reaction vessel was then sealed and heated at 90° C. for 6 h. The reaction mixture was then filtered (PTFE, 0.5 g), then acidified to pH 2.0. The filtrate was extracted with ethyl acetate, and the combined organic layers were washed sequentially with 1N HCl and water, then dried over sodium sulfate and concentrated. Purification by flash column chromatography 40 g silica gel, 50% to 100% ethyl acetate in hexanes) provided the product (620 mg, 90% yield) as a white solid. LC retention time: 2.99 min.

Preparation 7

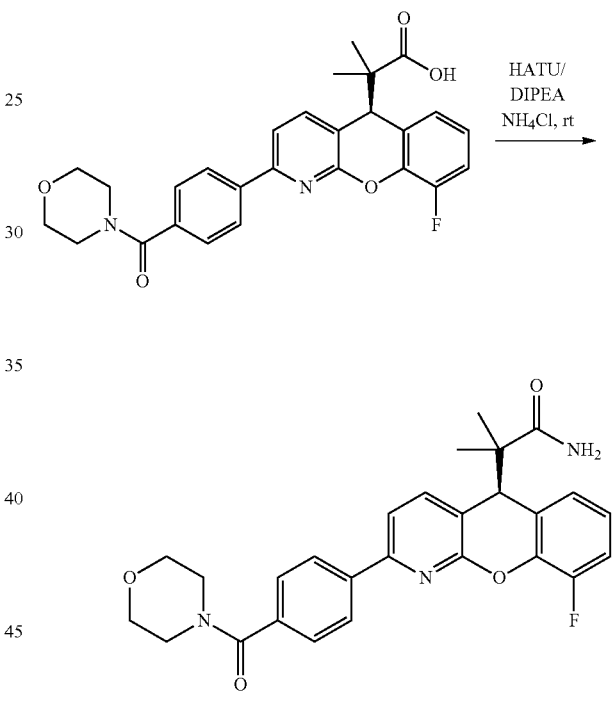

To a solution of the product of Preparation 6 (100 mg, 0.210 mmol) in DMF (1.5 mL) was added HATU (96 mg, 0.252 mmol), DIEA (0.110 mL, 0.630 mmol), and ammonium chloride (33.7 mg, 0.630 mmol), sequentially. The reaction mixture was stirred at room temperature for 12 h, then quenched with the addition of saturated aqueous sodium bicarbonate. The mixture was then extracted with ethyl acetate. The organic layer was dried over sodium sulfate and concentrated. Preparative HPLC provided the title compound (95 mg, 77% yield) as a white solid. MS (E+) m/z: 476 (M+H); LC retention time: 2.74 min. Proton NMR (400 MHz, CDCl$_3$) δ ppm 1.00-1.14 (m, 6H) 3.39-3.93 (m, 8H) 4.59 (s, 1H) 7.04-7.19 (m, 3H) 7.50 (d, J=8.28 Hz, 2H) 7.59 (s, 1H) 7.61 (s, 1H) 7.76 (d, J=7.78 Hz, 1H) 8.11 (d, 2H).

Preparation 8

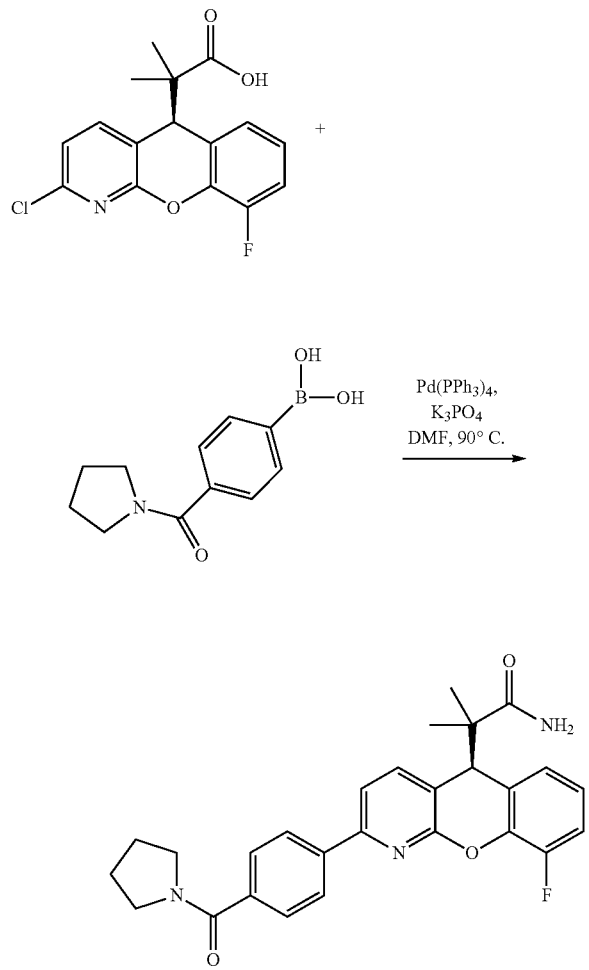

To a solution of the product of Preparation 2 (60 mg, 0.187 mmol) in anhydrous DMF (2 mL) was added 4-(pyrrolidine-1-carbonyl)phenylboronic acid (49.2 mg, 0.224 mmol) and potassium phosphate tribasic monohydrate (0.281 mL, 0.561 mmol) and tetrakis triphenylphosphine palladium(0) (21.62 mg, 0.019 mmol). Nitrogen was bubbled through the reaction mixture for 10 min, and then reaction vessel was then sealed. The reaction mixture was stirred at 90° C. for 4 h. The reaction mixture was then filtered and extracted with EtOAc. The organic layer was then washed with saturated aqueous sodium bicarbonate NaHCO$_3$, dried (Na$_2$SO$_4$) and concentrated. Purification by flash column chromatography (40 g silica gel, 50-80% EtOAc/hexanes) provided the product (70 mg, 81% yield) as a white solid. MS (E+) m/z: 460 (M+H); LC retention time: 2.97 min.

Preparations 9 to 18

The following compounds were prepared from the title compound of Preparation 2 in a similar manner to that used for the preparation of the title compound of Preparation 8. The product of Preparation 15 was prepared using the boronate product of Preparation 22.

| Preparation | X | R | HPLC Retention Time, min |
|---|---|---|---|
| 9 | CH | SO$_2$Et | 2.97 |
| 10 | CH | SO$_2$iPr | 3.12 |
| 11 | CH | SO$_2$Me | 2.82 |
| 12 | N | morpholine-N-* | 2.26 |
| 13 | CH | OiPr | 3.63 |
| 14 | CF | OiPr | 3.66 |
| 15 | CH | C(CH$_3$)$_2$OH | 3.17 |
| 16 | CH | H | |
| 17 | CH | iBu | |
| 18 | N | CO$_2$H | 2.35 |

Preparations 19 and 20

The following compounds were prepared from the title compound of Preparation 2 in a similar manner to that used for the preparation of the title compound of Preparation 8.

| Preparation | R | HPLC Retention Time, min |
|---|---|---|
| 19 | 4-methylpiperazin-1-yl-pyrimidin-2-yl-* | 2.20 |
| 20 | pyridin-3-yl-* | |

Preparation 21

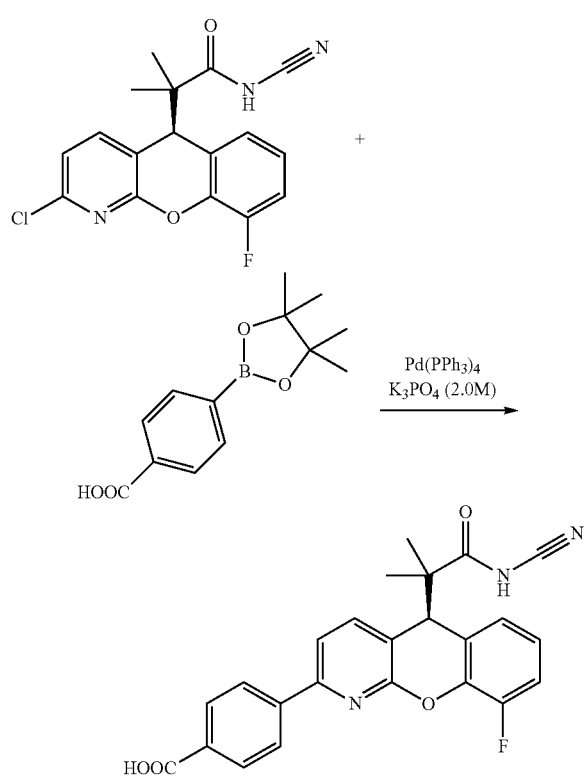

The product was prepared from Preparation 3 in a manner similar to the preparation of the product of Preparation 8. The product was yielded as a white solid. MS (E+) m/z: 432.1 (M+H); LC retention time: 3.17 min. $^1$H NMR (400 MHz, MeOD) δ ppm 8.00-8.13 (4H, m), 7.77 (2H, s), 7.07-7.20 (2H, m), 7.01 (1H, d, J=7.5 Hz), 4.43 (1H, s), 0.98 (6H, s).

Preparation 22

Step 1

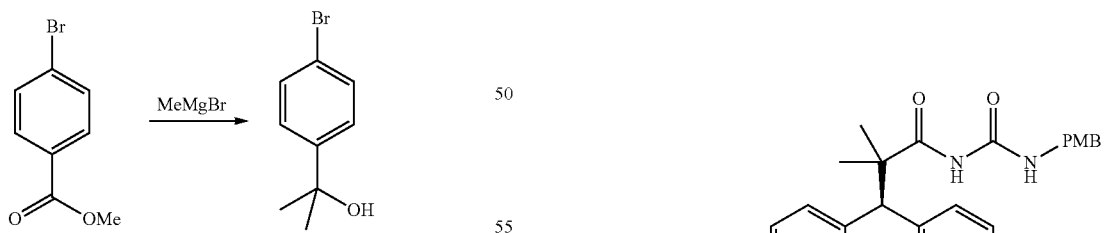

To a solution of methyl 4-bromobenzoate (5 g, 23.25 mmol) in THF (50 mL) at 0° C. was added methylmagnesium bromide (23.25 mL, 69.8 mmol) (3M in diethyl ether) dropwise. The resulted mixture was stirred at room temperature for 5 h. Aqueous citric acid (1M) was added, and the mixture stirred for 1 h, then extracted with ethyl acetate. The organic layer was dried over sodium sulfate, concentrated, and purified by flash column chromatography (80 g silica gel, 20%-50% EtOAc/hexanes) to provide the product of Step 1 (4.5 g, 90% yield) as a colorless oil. LC retention time: 2.63 min.

Step 2

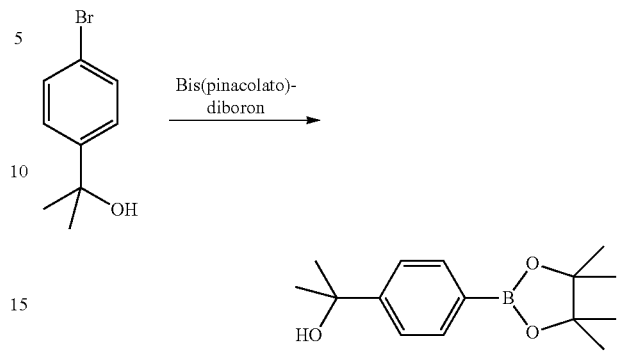

To a solution of 2-(4-bromophenyl)propan-2-ol (3 g, 13.95 mmol) in 1,4-dioxane (30 mL) was added potassium acetate (4.11 g, 41.8 mmol) and PdCl$_2$(dppf) (0.510 g, 0.697 mmol). The mixture was degassed with argon over 15 min, after which time bis(pinacolato)diboron (8.85 g, 34.9 mmol) was added under argon stream and the mixture was heated for 5 h at 80° C. The mixture was filtered over CELITE®, then partitioned between ethyl acetate and water. The organic layer was dried over sodium sulfate, concentrated, and purified by flash column chromatography (40 g silica gel, 50% dichloromethane/EtOAc) to provide the product of Step 2 (2.5 g, 68% yield) as a white solid. LC retention time: 3.02 min.

Preparation 23

To a solution of the product of Preparation 2 (100 mg, 0.312 mmol) in toluene (1 mL) was added 1-(isocyanatomethyl)-4-methoxybenzene (0.067 mL, 0.468 mmol). The resulting mixture was heated to 90° C. for 12 h, then purified by preparative HPLC to provide the product as a white solid. LC retention time: 3.65 min.

Preparation 24

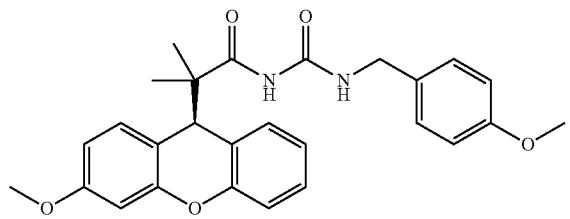

The product of Preparation 24 was prepared from the product of Preparation 4 in the same manner as the product of Preparation 23. MS (E+) m/z: 461 (M+H); LC retention time: 3.94 min.

Preparation 25

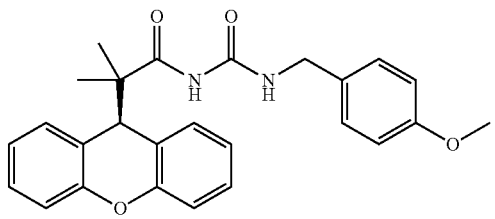

The product of Preparation 25 was prepared from the product of Preparation 5 in the same manner as the product of Preparation 23. MS (E+) m/z: 431 (M+H); LC retention time: 3.93 min.

Preparation 26

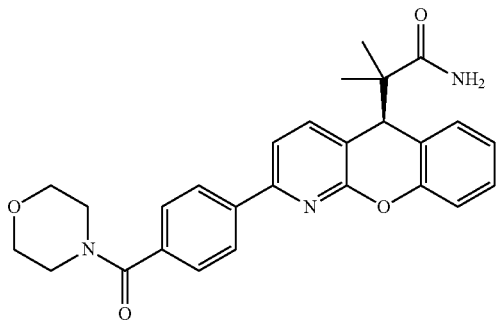 [SMILES: CC(C)(C(N)=O)[C@H]1c2ccccc2Oc2nc(-c3ccc(C(=O)N4CCOCC4)cc3)ccc21]

The title compound was prepared in a manner similar to the preparation of the product of Preparation 8.

Preparations 27 to 34

The following compounds were prepared in a similar manner to that used for the preparation of the title compound of Preparation 26. The product of Preparation 33 was prepared using the boronate product of Preparation 22.

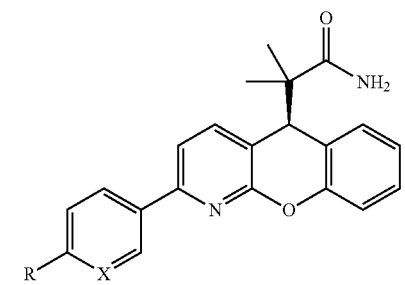

| Preparation | X | R |
| --- | --- | --- |
| 27 | CH | OiPr |
| 28 | CH | H |
| 29 | CH | iBu |
| 30 | CH | SO$_2$Et |
| 31 | CH | pyrrolidine-carbonyl |
| 32 | CF | morpholine-carbonyl |
| 33 | CH | C(CH$_3$)$_2$OH |
| 34 | CF | OiPr |

Preparation 35

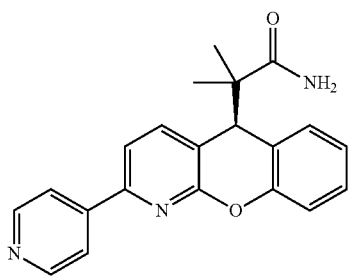 [SMILES: CC(C)(C(N)=O)[C@H]1c2ccccc2Oc2nc(-c3ccncc3)ccc21]

The product of Preparation 35 was prepared in a similar manner to that used for the preparation of the title compound of Preparation 8.

Preparation 36

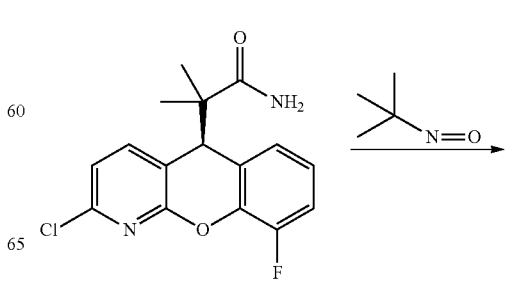

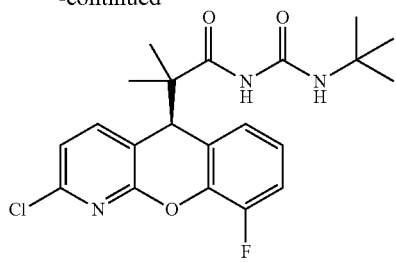

To a solution of the product of Preparation 2 (200 mg, 0.624 mmol) in toluene (2 mL) was added 2-isocyanato-2-methylpropane (93 mg, 0.935 mmol). The resulting mixture was heated to 90° C. for 12 h. The solvent was removed and the residue purified by flash column chromatography (24 g silica, 20% to 80% ethyl acetate in hexanes). MS (E+) m/z: 420 (M+H); LC retention time: 3.68 min.

Preparation 37

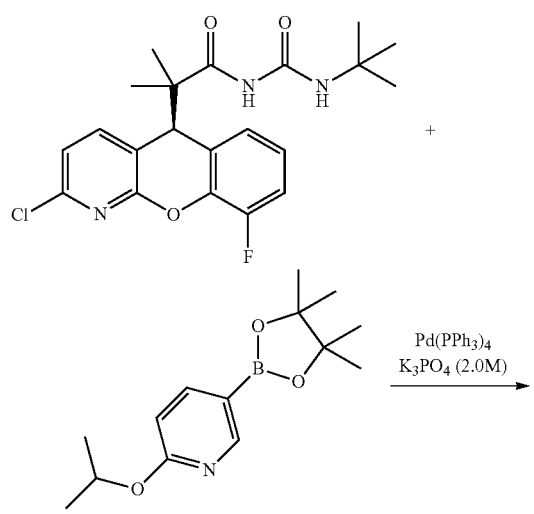

To a solution of the product of Preparation 36 (100 mg, 0.238 mmol) diazaxanthene chloride in DMF (1 mL) was added 2-isopropoxy-5-(4,4,5,5-tetramethyl-1,3,2-dioxaborolan-2-yl)pyridine (75 mg, 0.286 mmol) and potassium phosphate tribasic monohydrate (0.357 mL, 0.714 mmol). The mixture was purged with argon gas for 10 min. and then tetrakis triphenylphosphine palladium(0) (13.76 mg, 0.012 mmol) was added. Argon was bubbled through the mixture for another 5 min. The reaction vessel was sealed and heated at 90° C. for 4 h. The reaction mixture was filtered (0.45µ PTFE), then partitioned between ethyl acetate and water. The aqueous layer was washed with ethyl acetate, and the combined organic layers were washed sequentially with water and brine, then dried over sodium sulfate and concentrated. Purification of the residue by preparative HPLC provided the product (60 mg, 48% yield) as a white solid. MS (E+) m/z: 521 (M+H); LC retention time: 4.15 min.

Preparations 38 to 41

The following compounds were prepared in a similar manner to that used for the preparation of the title compound of Preparation 37.

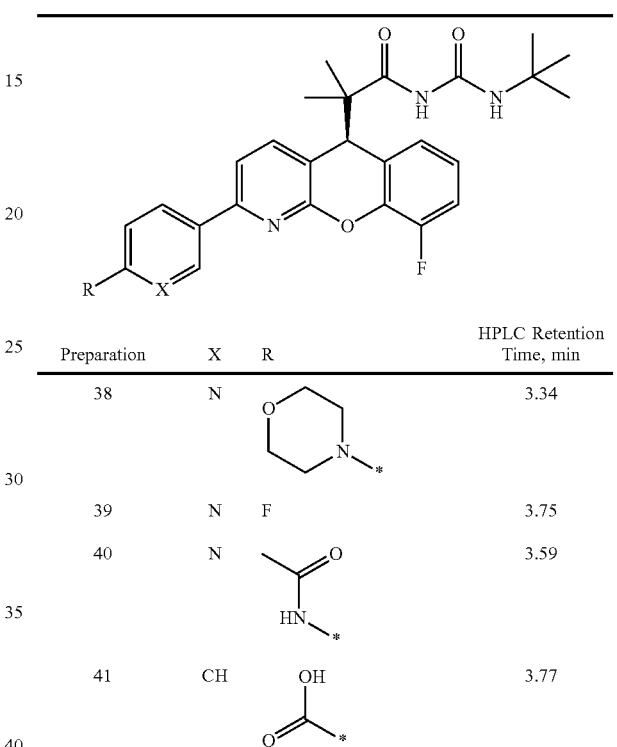

| Preparation | X | R | HPLC Retention Time, min |
|---|---|---|---|
| 38 | N | morpholine-N-* | 3.34 |
| 39 | N | F | 3.75 |
| 40 | N | HN(C(=O)CH_3)-* | 3.59 |
| 41 | CH | HOOC-* | 3.77 |

Preparation 42

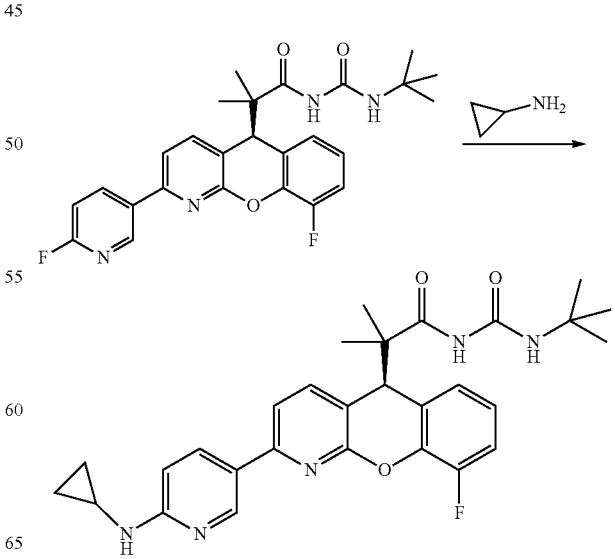

A solution of (S)—N-(tert-butylcarbamoyl)-2-(9-fluoro-2-(6-fluoropyridin-3-yl)-5H-chromeno[2,3-b]pyridin-5-yl)-2-methylpropanamide (3 mg, 6.24 μmol) in neat cyclopropanamine (0.5 mL, 6.24 μmol) was heated to 90° C. for 12 h. LC showed completion of the reaction. The reaction mixture was evaporated under vacuum to yield crude product (3.2 mg) as colorless oil, which was proceeded to next step without purification. LC retention time: 3.06 min.

Preparation 43

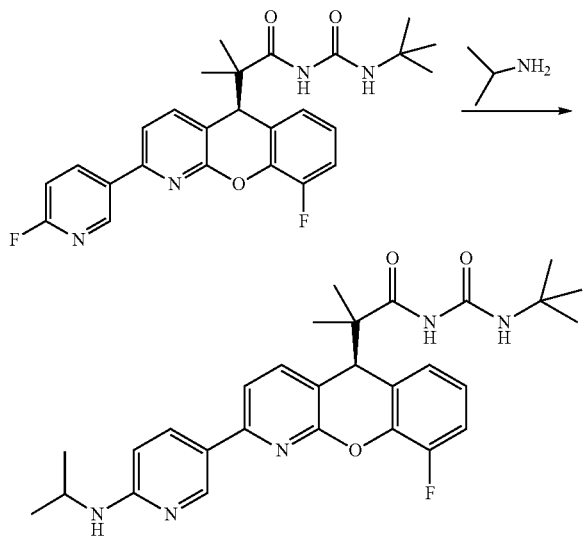

The product was prepared in a manner similar to the preparation of the product of Preparation 42. LC retention time: 3.11 min.

Preparation 44

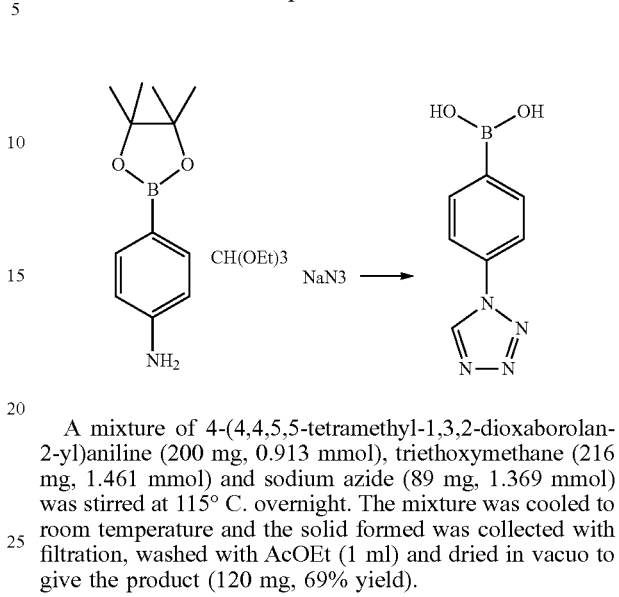

A mixture of 4-(4,4,5,5-tetramethyl-1,3,2-dioxaborolan-2-yl)aniline (200 mg, 0.913 mmol), triethoxymethane (216 mg, 1.461 mmol) and sodium azide (89 mg, 1.369 mmol) was stirred at 115° C. overnight. The mixture was cooled to room temperature and the solid formed was collected with filtration, washed with AcOEt (1 ml) and dried in vacuo to give the product (120 mg, 69% yield).

Preparation 45

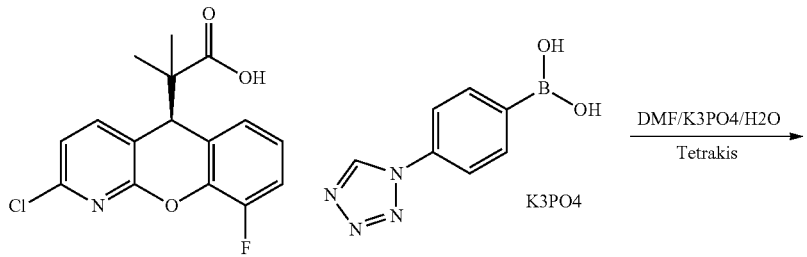

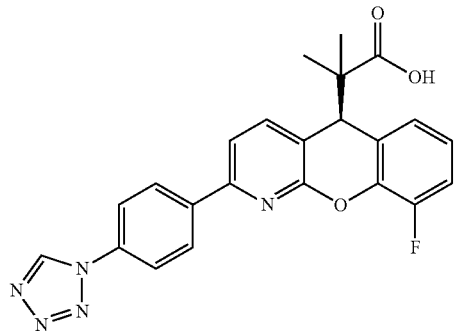

The product was prepared in a manner similar to the preparation of the product of Preparation 6.

Preparation 46

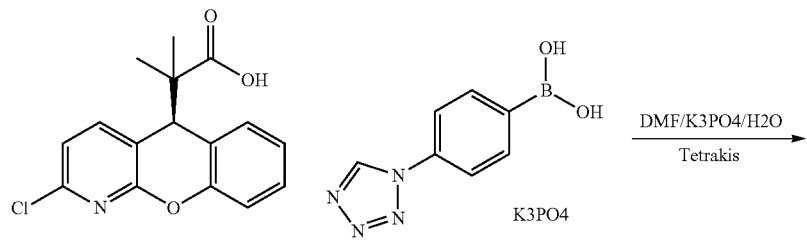

The product was prepared in a manner similar to the preparation of the product of Preparation 6.

Preparation 47

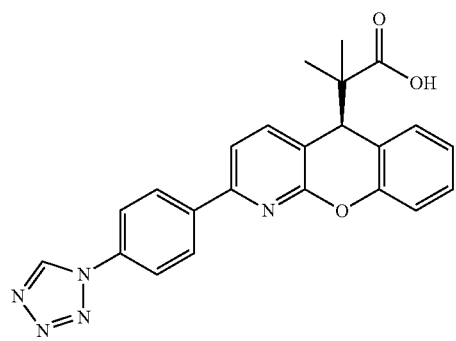

The product was prepared in a manner similar to the preparation of the product of Preparation 6.

Preparation 48

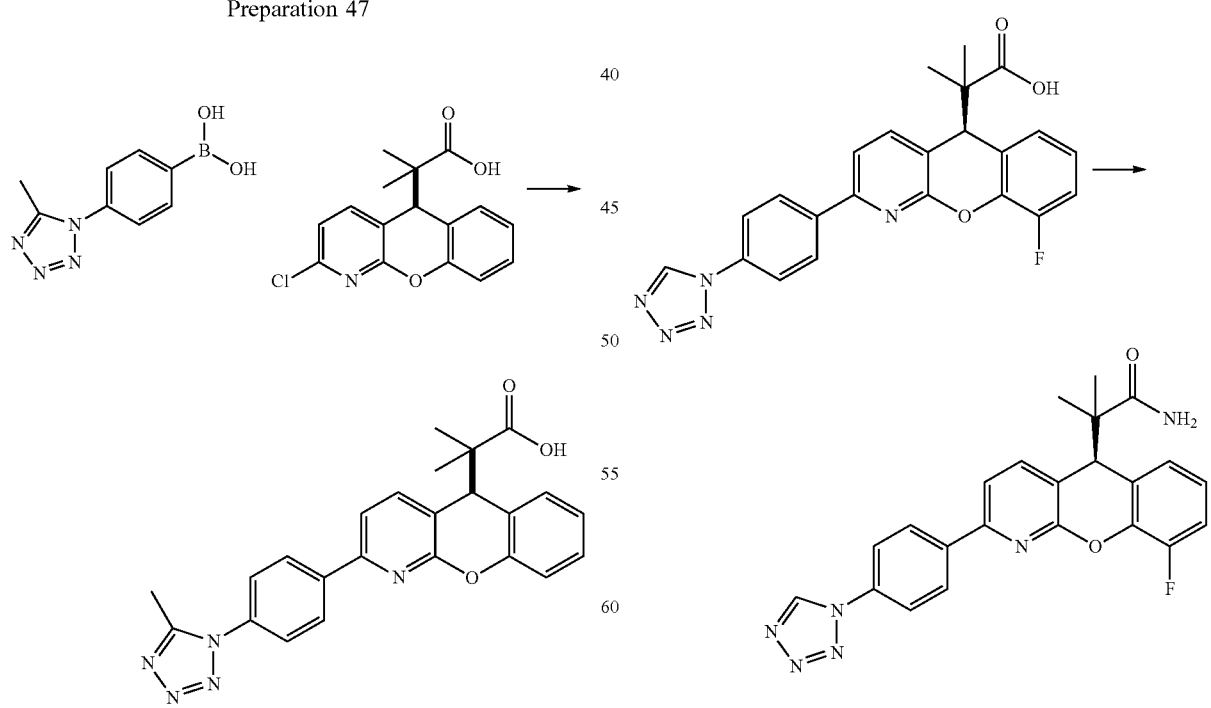

The product was prepared from the product of Preparation 45 in a manner similar to the preparation of the product of Preparation 7.

Preparation 49

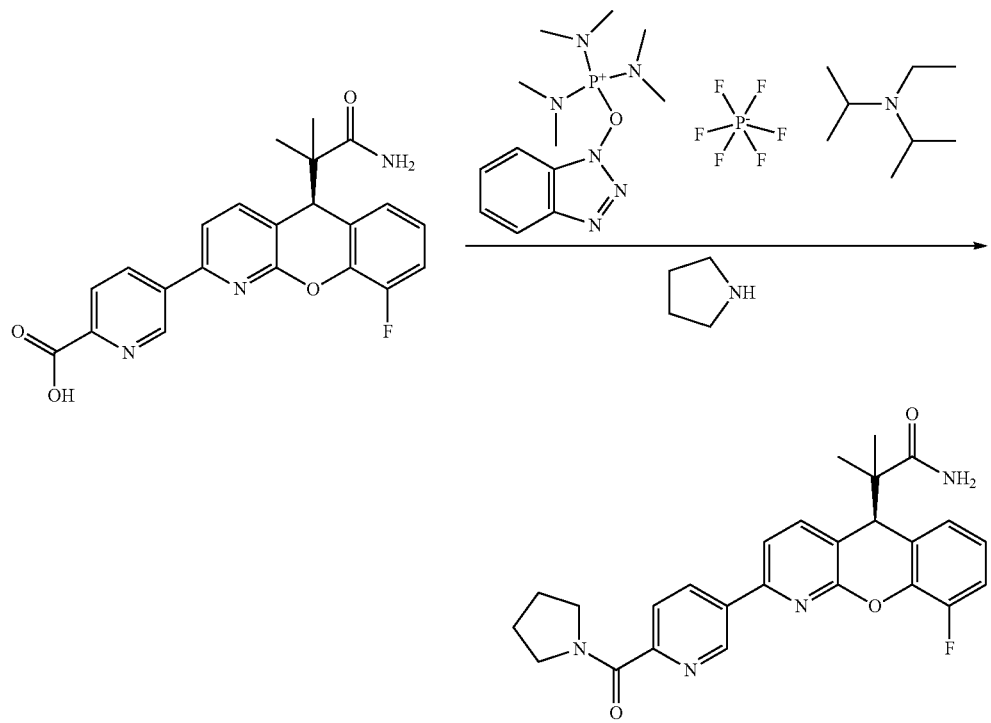

To a solution of the product of Preparation 18 (50 mg, 0.123 mmol) in DMF (1 mL) was added BOP (65.1 mg, 0.147 mmol), N,N-diisopropylethylamine (0.064 mL, 0.368 mmol) and pyrrolidine (17.46 mg, 0.245 mmol). The resulting mixture was stirred at room temperature for 5 h. Purification by preparative HPLC provided the product (30 mg, 53% yield) as a white solid. MS (E+) m/z: 461 (M+H); LC retention time: 3.04 min.

Preparation 50

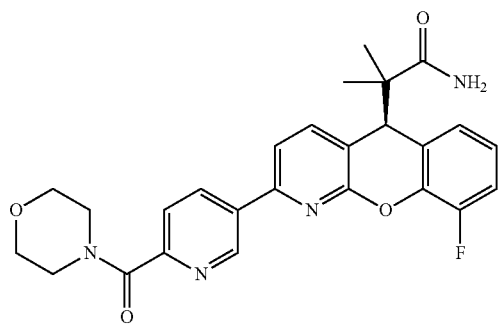 [SMILES: CC(C)(C(N)=O)[C@@H]1c2ccc(-c3ccc(C(=O)N4CCOCC4)nc3)nc2Oc2c(F)cccc21]

The title compound was prepared in a similar manner to that used for the preparation of the title compound of Preparation 49. LC retention time: 2.72 min.

Preparation 51

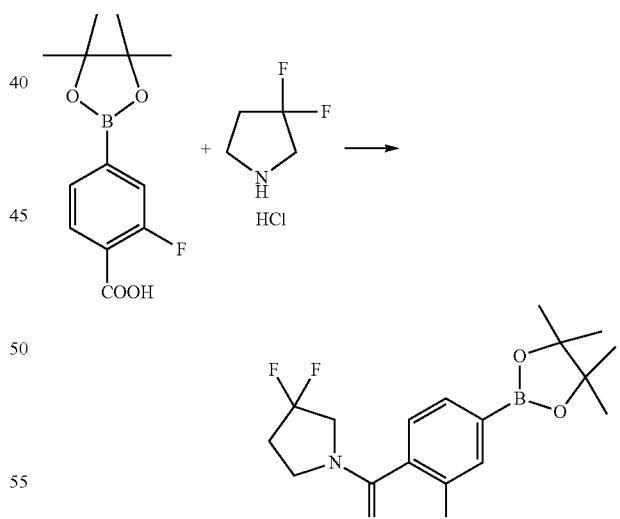

To a solution of 2-fluoro-(4,4,5,5-tetramethyl-1,3,2-dioxaborolan-2-yl)benzoic acid (230 mg, 0.86 mmol) in anhydrous dichloromethane (3 mL) was added 3,3-difluoropyrrolidine hydrochloride (138 mg, 1.29 mmol), EDCI hydrochloride (198 mg, 1.03 mmol), 1-hydroxy benzotriazole (140 mg, 1.03 mmol) and triethylamine (0.5 mL, 3.45 mmol). The reaction mixture was stirred at room temperature for overnight. Then the reaction mixture was diluted with dichloromethane washed with water, brine, dried over Preparation 52

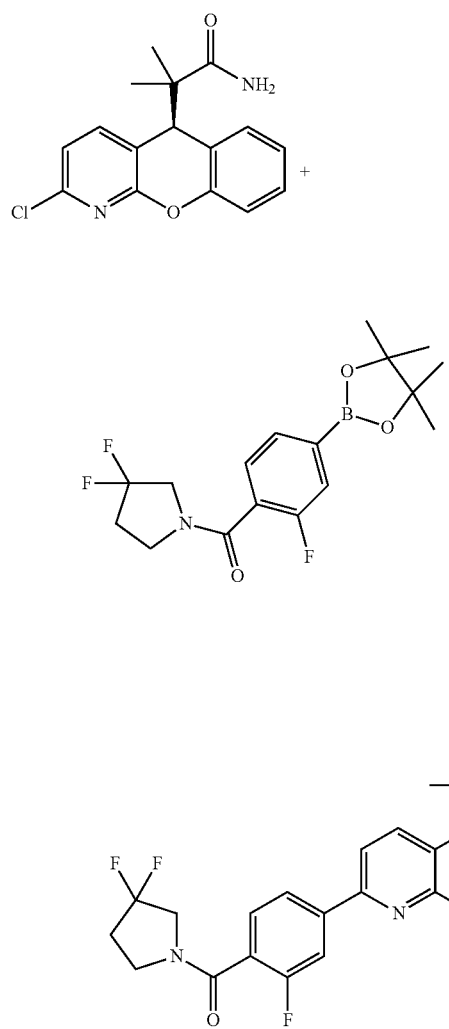

To a solution of the product of Preparation 1 (80 mg, 0.26 mmol) in anhydrous DMF (3 mL) was added the product of Preparation 51 (140 mg, 0.39 mmol) and potassium phosphate tribasic monohydrate (0.381 mL, 1.056 mmol) and tetrakis triphenylphosphine palladium (0) (21 mg, 0.018 mmol). Nitrogen was bubbled through the reaction mixture for 10 min, and then reaction vessel was sealed. The reaction mixture was stirred at 105° C. for overnight. The reaction mixture was concentrated and partitioned between water and EtOAc. The organic layer was then washed with brine, dried over sodium sulfate, concentrated and purified by column chromatography (60-120 silica gel, 3% methanol/chloroform) to obtain the product (100 mg, 77% yield) as a white solid. MS (E+) m/z: 496 (M+H); LCMS retention time: 1.98 min (Method 9).

Preparation 53

Step 1

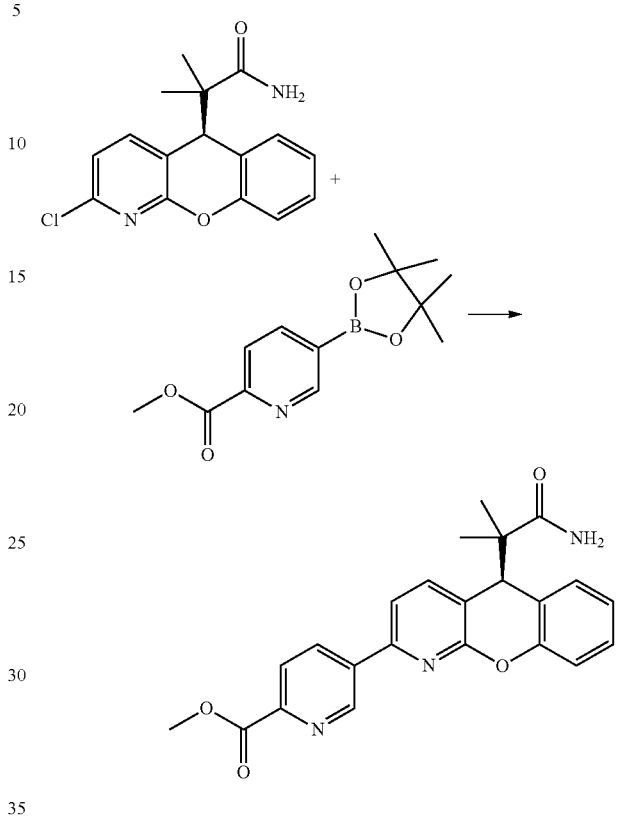

To a solution of the product of Preparation 1 (100 mg, 0.332 mmol) in anhydrous DMF (3 mL) was added 2-methoxycarbonyl-5-pyridineboronic acid, pinacolester (174 mg, 0.664 mmol), cesium carbonate (215 mg, 0.664 mmol), copper (I) iodide (12 mg, 0.063 mmol), palladium acetate (6 mg, 0.029 mmol) and 1,1-bis(diphenylphosphinoferrocene) (34 mg, 0.063 mmol). Nitrogen was bubbled through the reaction mixture for 10 min, and then reaction vessel was sealed. The reaction mixture was stirred at 100° C. for overnight. The reaction mixture was then filtered and extracted with EtOAc. The organic layer was washed with water, brine, dried over sodium sulfate, concentrated and purified by column chromatography (60-120 silica gel, 2% methanol/chloroform) to gave the product (80 mg, 70% yield) as off-white solid. MS (E+) m/z: 404 (M+H); LCMS retention time: 1.65 min (Method 9).

Step 2

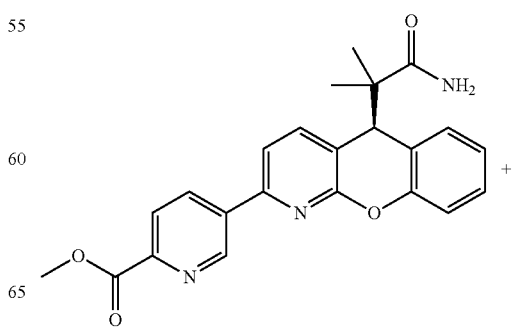

-continued

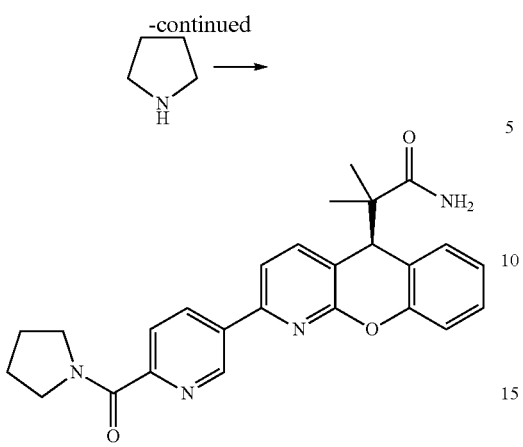

To the product of Step 1 (40 mg, 0.099 mmol) was added pyrrolidine (21 mg, 0.297 mmol) and the reaction vessel was sealed. The reaction mixture was stirred at 120° C. for overnight. The crude product was purified by preparative TLC using 5% methanol/chloroform as eluent and yielded the product (35 mg, 79% yield) as an off-white semi solid. MS (E+) m/z: 443 (M+H); LCMS retention time: 1.75 min (Method 9).

Preparation 54

The title compound was prepared in a manner similar to that of the preparation of the product of Preparation 53. MS (E+) m/z: 459 (M+H); LC retention time: 1.56 min.

Preparation 55

The title compound was prepared in a manner similar to that of the preparation of the product of Preparation 53. MS (E+) m/z: 494 (M+H); LCMS retention time: 1.56 min (Method 9).

Preparation 56

The title compound was prepared using the title compound of Preparation 1 and boronic acid the product of Step 4 in a manner similar to that of the preparation of the product of Preparation 53. MS (E+) m/z: 466 (M+H); LCMS retention time: 1.46 min (Method 9).
Step 1

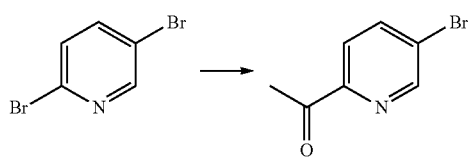

To a solution of 2,5-dibromopyridine (5 g, 22.026 mmol) in anhydrous toluene (200 mL) at −50° C. was added n-butyllithium (13.75 mL, 22.026 mmol) (1.6M in hexane) dropwise. The resulted mixture was stirred at −50° C. temperature for 45 min. N,N-dimethylacetamide (3.61 mL, 37.44 mmol) was added dropwise at the same temperature and then allowed to reach room temperature slowly. The reaction mixture was stirred at room temperature for 1 h and quenched with saturated ammonium chloride solution, then extracted with EtOAc. The organic layer was dried over sodium sulfate, concentrated and purified by column chromatography (60-120 silica gel, 1% EtOAc/hexane) to provide the product of Step 1 (2.9 g, 65% yield) as a white solid. LCMS retention time: 1.46 min (Method 7).
Step 2

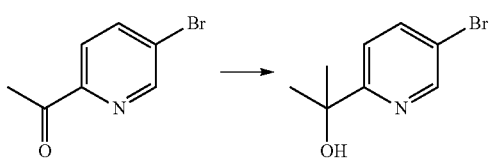

To a solution of 1-(5-bromopyridine-2-yl)ethanone (2.9 g, 14.5 mmol) in anhydrous THF (87 mL) at −78° C. was added methylmagnesium bromide (38.66 mL, 116.0 mmol) (3M in diethyl ether) dropwise. The resulted mixture was stirred at room temperature for overnight. Saturated ammonium chloride solution was added and the mixture stirred for 30 min, then extracted with ethyl acetate. The organic layer was dried over sodium sulfate, concentrated and purified by column chromatography (60-120 silica gel, 2-3% EtOAc/hexane) to gave the product of Step 2 (1.66 g, 53% yield) as a pale yellow liquid. LCMS retention time: 1.40 min (Method 8).
Step 3

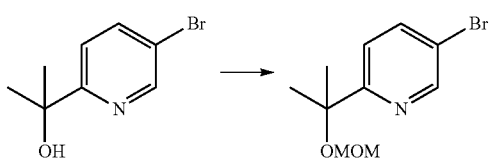

To a solution of 2-(5-bromopyridin-yl)propan-2-ol (1.66 g, 7.68 mmol) in N,N-diisopropylethylamine (16 mL) at 0° C. was added MOM chloride (1.42 mL, 23.05 mmol) dropwise. The resulted mixture was heated at 120° C. for overnight. Then, the reaction mixture was concentrated, partitioned between water and EtOAc. The organic layer was dried over sodium sulfate, concentrated and purified by column chromatography (60-120 silica gel, 1% EtOAc/hexane) to provide the product of Step 3 (1.5 g, 75% yield) as a yellow liquid. LCMS retention time: 1.84 min (Method 9).
Step 4

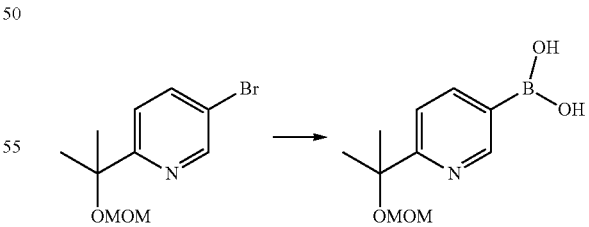

To a solution of 5-bromo-2-(-2-(methoxymethyl)propane-2-yl)pyridine (1.5 g, 6.94 mmol) in anhydrous toluene/THF (10/3 mL) at −50° C. was added n-butyllithium (5.2 mL, 8.33 mmol) (1.6M in hexane) dropwise. The resulted mixture was stirred at −50° C. for 10 min. Triisopropyl borate (1.95 mL, 8.33 mmol) was added dropwise at the same temperature and then allowed to reach room temperature slowly. The reaction mixture was stirred at room temperature for 1 h and cooled to −30° C., quenched with 2N HCl (15 mL). After decantation, the pH of the aqueous layer was adjusted to pH 7 with 1N NaOH (15 mL), and extracted with ethyl acetate The organic layer was dried over sodium sulfate and concentrated to provide the product of Step 4 (800 mg, 51% yield) as an off-white sticky foam. LCMS retention time: 1.42 min (Method 9).

Preparation 57

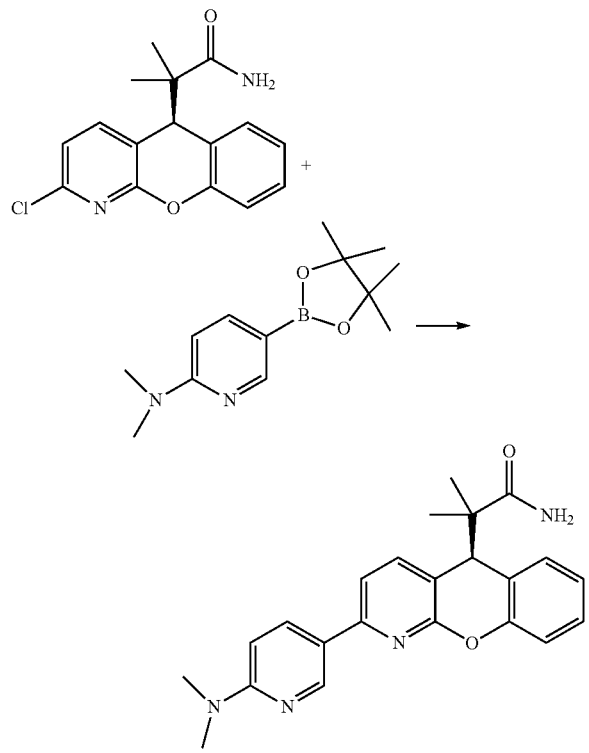

The compound was prepared from the title compound of Preparation 1 in a similar manner to that used for the preparation of the title compound of Preparation 52. MS (E+) m/z: 389 (M+H); LCMS retention time: 1.65 min (Method 9); $^1$H-NMR (400 MHz, DMSO-d$_6$): δ 0.82 (s, 3H), 0.90 (s, 3H), 3.11 (s, 6H), 4.48 (s, 1H), 6.75 (d, J=8.80 Hz, 1H), 7.04-7.15 (m, 4H), 7.33-7.34 (m, 2H), 7.70-7.73 (m, 2H), 8.19-8.20 (m, 1H), 8.85 (s, 1H).

Preparation 58

Step 1

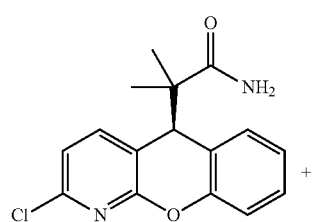

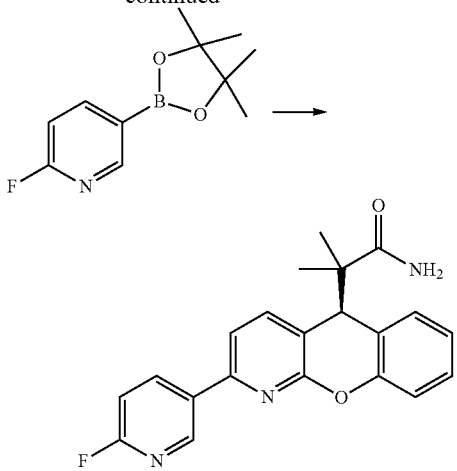

To a solution of the product of Preparation 1 (100 mg, 0.331 mmol) in anhydrous toluene (3 mL) was added 2-fluoro-5-pyridine boronic acid, pinacolatester (110 mg, 0.496 mmol) and sodium carbonate (105 mg in 2 mL H$_2$O, 0.993 mmol) and tetrakis triphenylphosphine palladium(0) (26 mg, 0.023 mmol). Nitrogen was bubbled through the reaction mixture for 10 min, and then reaction vessel was sealed. The reaction mixture was stirred at 100° C. for overnight. The reaction mixture was then filtered and extracted with EtOAc. The organic layer was washed with brine, dried over sodium sulfate and concentrated to provide the product (65 mg, 54% yield) as an off-white solid. MS (E+) m/z: 364 (M+H); LCMS retention time: 1.62 min (Method 9).

Step 2

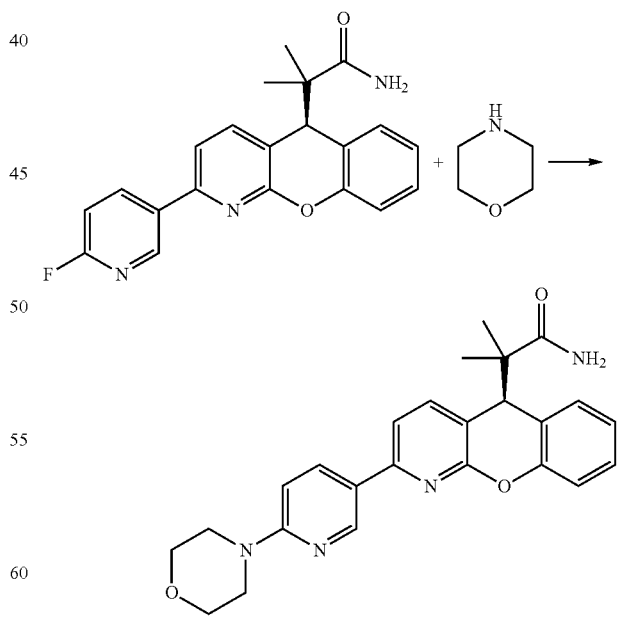

The title compound was prepared from the product of Step 1 in a manner similar to that of the preparation of the product of Preparation 42. MS (E+) m/z: 431 (M+H); LCMS retention time: 1.69 min (Method 9).

Preparation 59

Step 1

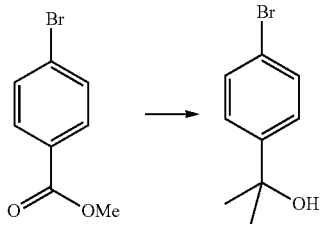

To a solution of methyl-4-bromobenzoate (5 g, 23.25 mmol) in THF (50 mL) at 0° C. was added methylmagnesium bromide (23.25 mL, 69.8 mmol) (3M in diethyl ether) dropwise. The resulted mixture was stirred at room temperature for 5 h. Then aqueous citric acid (1M) was added, the mixture stirred for 1 h, and extracted with ethyl acetate. The organic layer was dried over sodium sulfate, concentrated and purified by flash column chromatography (80 g silica gel, 20%-50% EtOAc/hexane) to provide the product of Step 1 (4.5 g, 90% yield) as a colorless oil. LCMS retention time: 2.63 min (Method 9).

Step 2

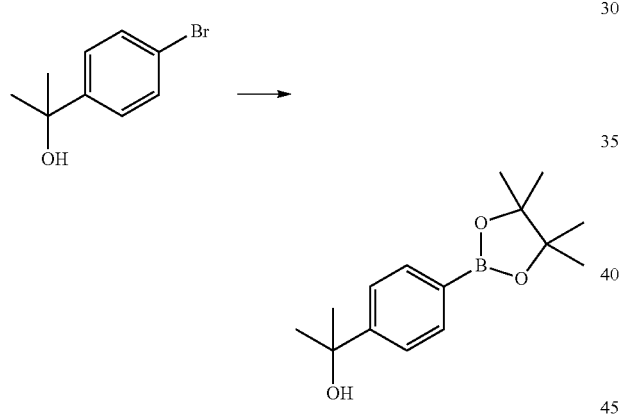

To a solution of 2-(4-bromophenyl)propan-2-ol (3 g, 13.95 mmol) in 1,4-dioxane (30 mL) was added potassium acetate (4.11 g, 41.8 mmol) and $PdCl_2$(dppf) (0.510 g, 0.697 mmol). The mixture was degassed with argon over 15 min, after which time bis(pinacolato)diborane (8.85 g, 34.9 mmol) was added under argon stream and the mixture was heated for 5 h at 80° C. The mixture was filtered over CELITE®, partitioned between ethyl acetate and water. The organic layer was dried over sodium sulfate, concentrated and purified by flash column chromatography (40 g silica gel, 50% dichloromethane/EtOAc) to afford the product of Step 2 (2.5 g, 68% yield) as a white solid. LCMS retention time: 3.02 min (Method 9).

Preparations 60 to 72

The following compounds were prepared from the title compounds of Preparation 1 and Preparation 2 in a manner similar to that used for the preparation of the title compound of Preparation 52.

| Preparation | X | Y | Z | R | LCMS Retention Time, min |
|---|---|---|---|---|---|
| 60 | C | CH | H | *-C(O)-pyrrolidine-3,3-F2 | 1.08 |
| 61 | C | CF | H | *-C(O)-pyrrolidine | 1.74 |
| 62d | C | CCl | H | *-C(O)-pyrrolidine | 1.86 |
| 63 | C | CCl | H | *-C(O)-pyrrolidine-3,3-F2 | 1.84 |
| 64 | C | N | H | *-C(O)-pyrrolidine | 1.75 |
| 65 | C | N | H | *-C(O)-morpholine | 1.56 |
| 66 | C | CF | F | *-C(O)-morpholine | 1.70 |
| 67 | C | N | H | *-C(CH3)2-OMOM | 1.81 |
| 68 | C | N | H | *-N(CH3)2 | 1.65 |
| 69 | C | N | H | *-morpholine (N-linked) | 1.75 |
| 70 | N | CH | H | — | 1.30 |

73
-continued

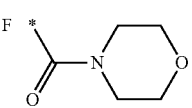

| Preparation | X | Y | Z | R | LCMS Retention Time, min |
|---|---|---|---|---|---|
| 71 | C | CH | F |  | 1.64 |
| 72 | C | CH | F | 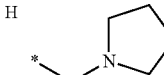 | 1.79 |

Preparation 73

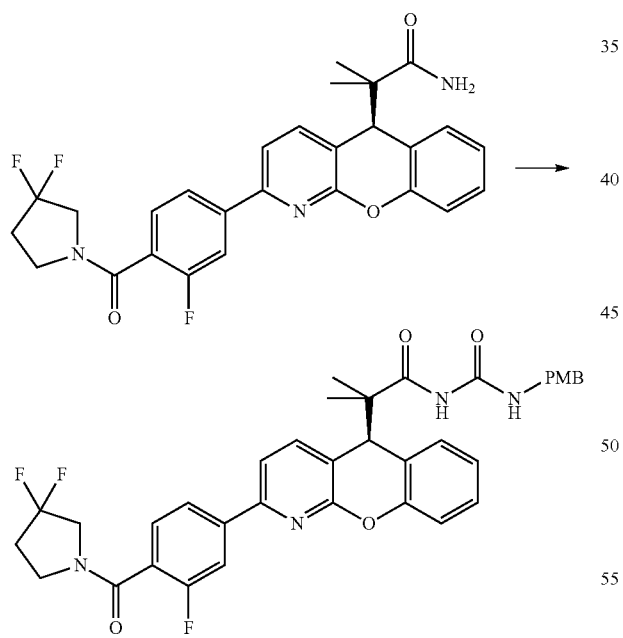

To a solution of the product of Preparation 52 (100 mg, 0.201 mmol) in anhydrous toluene (4 mL) was added p-methoxybenzylisocyanate (49 mg, 0.302 mmol). The reaction mixture was stirred at 90° C. for 40 h. Then the reaction mixture was concentrated and purified by preparative TLC using 5% methanol/chloroform as eluent to provide the product (60 mg, 45% yield) as a sticky liquid. MS (E+) m/z: 659 (M+H); LCMS retention time: 2.14 min (Method 7).

74
Preparations 74 to 83

The following compounds were prepared from the title compounds of Preparations 60 to 70 in a similar manner to that used for the preparation of the title compound of Preparation 73.

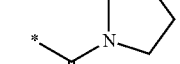

| Preparation | X | Y | Z | R | LCMS Retention Time, min |
|---|---|---|---|---|---|
| 74 | C | CH | H | 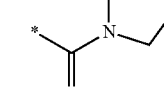 | 2.16 |
| 75 | C | CF | H | 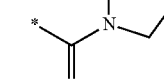 | 1.90 |
| 76 | C | CCl | H | 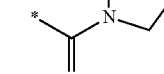 | 2.10 |
| 77 | C | CCl | H | 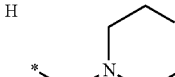 | 2.13 |
| 78 | C | N | H |  | 1.93 |
| 79 | C | N | H | | 1.91 |
| 80 | C | CF | F | | 2.10 |

75 -continued

Structure: Pyridine-chromene core with 2-methylpropanamide urea linked to PMB group, substituted with R-X=Y-pyridyl at 2-position, Z at 8-position.

| Preparation | X | Y | Z | R | LCMS Retention Time, min |
|---|---|---|---|---|---|
| 81 | C | N | H | *—C(CH₃)₂—OMOM | 2.11 |
| 82 | C | N | H | *—N(CH₃)₂ on C(CH₃)₂ | 2.10 |

76 -continued

| Preparation | X | Y | Z | R | LCMS Retention Time, min |
|---|---|---|---|---|---|
| 83 | C | N | H | *—N(morpholine) | 1.85 |

Preparations 84 to 87

The following compounds were prepared from the title compounds of Preparations 71 and 72 in a similar manner to that used for the preparation of the title compound of Preparation 73. The respective isocyanates i.e., [(2-isocyanatoethoxy)methyl]benzene and [(1-isocyanato-2-methylpropan-2-yloxymethyl]benzene were prepared using 2-aminoethanol and 1-amino-2-methylpropan-2-ol according to steps 1 to 4 (below).

Structure: Pyridine-chromene core with 2-methylpropanamide urea linked to X, R at 2-position, F at 8-position.

| Preparation | R | X | LCMS Retention Time, min |
|---|---|---|---|
| 84 | 4-(morpholine-4-carbonyl)phenyl* | *—C(=O)NH—CH₂CH₂—OBn | 2.01 |
| 85 | 4-(morpholine-4-carbonyl)phenyl* | *—C(=O)NH—CH₂C(CH₃)₂—OBn | 2.12 |
| 86 | 4-(2-hydroxypropan-2-yl)phenyl* | *—C(=O)NH—CH₂C(CH₃)₂—OBn | 2.22 |

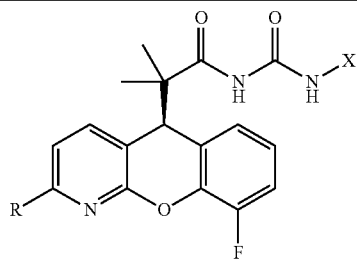

| Preparation | R | X | LCMS Retention Time, min |
|---|---|---|---|
| 87 | ![4-(2-hydroxypropan-2-yl)phenyl] | ![N-(2-(benzyloxy)ethyl)carbamoyl] | 2.09 |

Preparation of [(2-isocyanatoethoxy)methyl]benzene

Step 1

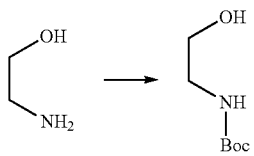

To a solution of 2-aminoethanol (2 g, 32.74 mmol) in THF (20 mL) at 0° C. was added 2M sodium hydroxide (16 mL). The resulted mixture was stirred for 30 min. Boc anhydride (7 g, 32.74 mmol) was added dropwise and stirred for overnight. The reaction mixture was extracted with diethyl ether. The organic layer was washed with brine, dried over anhydrous sodium sulfate and concentrated to provide the product (4 g, 75% yield) as a colorless liquid. $^1$H-NMR (400 MHz, DMSO-$d_6$): δ 1.37 (s, 9H), 2.98 (q, J=6.40 Hz, 2H), 3.35 (q, J=6.00 Hz, 2H), 4.57 (t, J=5.60 Hz, 1H), 6.67 (t, J=4.80 Hz, 1H).

Step 2

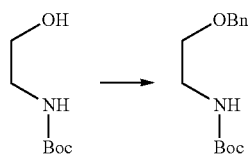 [SMILES: CC(C)(C)OC(=O)NCCO ; CC(C)(C)OC(=O)NCCOCc1ccccc1]

To a solution of the product of Step 1 (4 g, 24.81 mmol) in 50% sodium hydroxide (40 mL) was added benzyl bromide (3.26 mL, 24.81 mmol) and benzyltriethylammonium chloride (0.46 g). The reaction mixture was stirred at room temperature for overnight. The reaction mixture was extracted with diethyl ether. The organic layer was washed with brine, dried over anhydrous sodium sulfate and concentrated the crude was purified by column chromatography (60-120 silica gel 15% EtOAc/hexane) to gave the product (4 g, 64% yield) as a colorless liquid. $^1$H-NMR (400 MHz, DMSO-$d_6$): δ 1.38 (s, 9H), 3.12 (q, J=6.00 Hz, 2H), 3.42 (t, J=6.00 Hz, 2H), 4.46 (s, 2H), 6.84 (bs, 1H), 7.31-7.36 (m, 5H).

Step 3

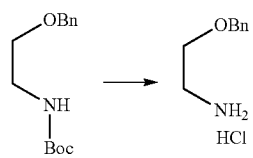

To a solution of the product of Step 2 (4 g, 15.93 mmol) in diethyl ether (10 mL) was added 4N HCl in ether (20 mL). The resulted mixture was stirred at room temperature for overnight. The reaction mixture was then filtered and washed with hexane, dried under vacuum to provide the product (2 g, 83% yield) as an off-white solid. $^1$H-NMR (400 MHz, DMSO-$d_6$): δ 3.01 (t, J=5.20 Hz, 2H), 3.63 (t, J=5.60 Hz, 2H), 4.54 (s, 2H), 7.35-7.36 (m, 5H), 8.01 (bs, 3H).

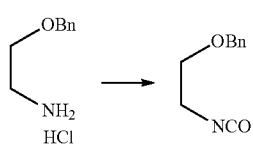

Step 4

To a solution of the product of Step 3 (200 mg, 1.322 mmol) in dichloromethane (3 mL) was added saturated sodium bicarbonate solution (25 mL). The resulted mixture was stirred for 10 min at room temperature. A solution of triphosgene (240 mg) in dichloromethane (2 mL) was added at 0° C. and the reaction mixture was stirred for 30 min at the same temperature. The organic layer was separated and washed with brine, dried over anhydrous sodium sulfate and concentrated to provide the product (100 mg, 42% yield) as a colorless liquid. $^1$H-NMR (400 MHz, DMSO-$d_6$): δ 3.45-3.47 (m, 4H), 4.53 (s, 2H), 7.18-7.32 (m, 5H).

Preparation of [(1-isocyanato-2-methylpropan-2-yloxymethyl]benzene

The title compound was prepared from the compound of 1-amino-2-methylpropan-2-ol in a similar manner to that used for the preparation of compound of [(2-isocyanatoethoxy)methyl]benzene (Steps 1 to 4 above).

Preparation 88

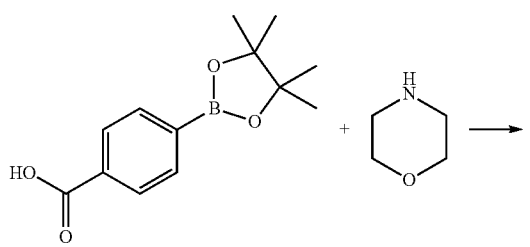

To a solution of 4-(4,4,5,5-tetramethyl-1,3,2-dioxaborolan-2-yl) benzoic acid (500 mg, 2.024 mmol) in anhydrous dichloromethane/DMF (9:1) (4.5 mL:0.5 mL) was added morpholine (264 mg, 3.036 mmol), EDCI.hydrochloride (582 mg, 3.036 mmol), 1-hydroxybenzotriazol (410 mg, 3.036 mmol) and triethylamine (0.54 mL, 4.048 mmol). The reaction mixture was stirred at room temperature for overnight. The reaction mixture was diluted with dichloromethane and then washed with water, brine solution, dried over anhydrous sodium sulfate and concentrated under vacuum to get the product (400 mg, 62% yield) as an off-white solid. MS (E+) m/z: 318 (M+H); LCMS retention time: 1.49 min (Method 7).

Preparation 89

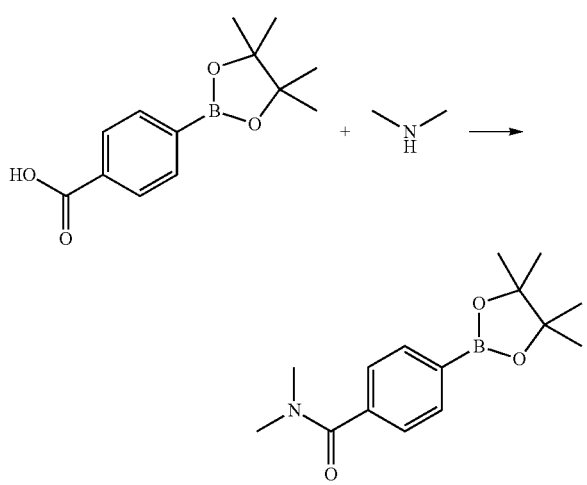

To a solution of 4-(4,4,5,5-tetramethyl-1,3,2-dioxaborolan-2-yl) benzoic acid (500 mg, 2.024 mmol) in anhydrous dichloromethane/DMF (9:1) (4.5 mL:0.5 mL) was added N,N-dimethylamine (264 mg, 3.036 mmol), EDCI.hydrochloride (582 mg, 3.036 mmol), 1-hydroxybenzotriazol (410 mg, 3.036 mmol) and triethylamine (0.54 mL, 4.048 mmol). The reaction mixture was stirred at room temperature for overnight. The reaction mixture was diluted with dichloromethane and then washed with water, brine solution, dried over anhydrous sodium sulfate and concentrated under vacuum to get the product (400 mg, 62% yield) as an off-white solid. MS (E+) m/z: 276 (M+H); LCMS retention time: 1.49 min (Method 7).

Preparation 90

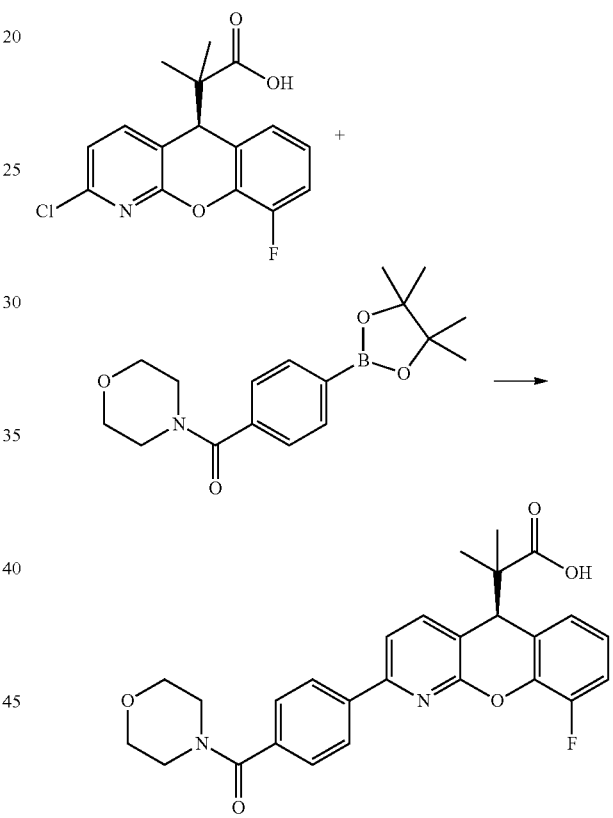

To a solution of (S)-2-(2-chloro-9-fluoro-5H-chromeno[2,3-b]pyridin-5-yl)-2-methylpropanoic acid (300 mg, 0.932 mmol) in anhydrous DMF (4 mL) was added the product of Preparation 88 (440 mg, 1.398 mmol), an aqueous solution of potassium phosphate tribasic (719 mg in 2 mL water, 3.73 mmol) and tetrakis triphenylphosphine palladium(0) (75 mg, 0.0652 mmol). Nitrogen was bubbled through the reaction mixture for 10 min and then reaction vessel was sealed. The reaction mixture was stirred at 100° C. for overnight. Then the reaction mixture was concentrated under vacuum and diluted with water. The aqueous solution was washed with EtOAc (2×10 mL) to remove the non-polar impurities and then acidified with 1.5N HCl (pH=2-3) and extracted with EtOAc (3×10 mL). The organic layer was washed with water, brine solution, dried over anhydrous sodium sulfate and concentrated under vacuum to get the product (300 mg, 67% yield) as an off-white solid. MS (E+) m/z: 477 (M+H); LCMS retention time: 1.33 min (Method 8).

Preparation 91

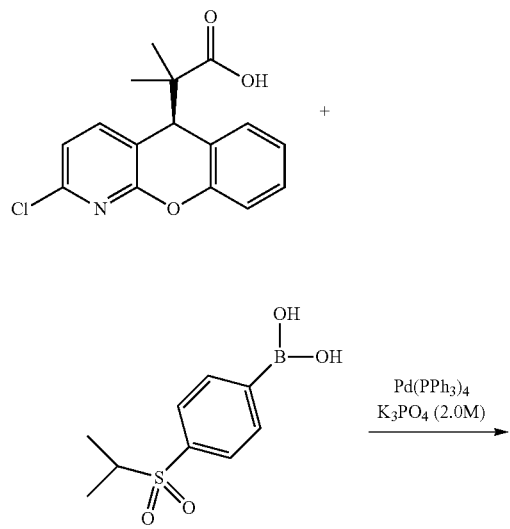

The title compound was prepared from the (S)-2-(2-chloro-9-fluoro-5H-chromeno [2,3-b]pyridin-5-yl)-2-methylpropanoic acid and (4-(isopropylsulfonyl)phenyl)boronic acid in a manner similar to that of Preparation 90. MS (E+) m/z: 452.2 (M+H); LCMS retention time: 3.36 min.

Preparation 92

The title compound was prepared from the (S)-2-(2-chloro-9-fluoro-5H-chromeno [2,3-b]pyridin-5-yl)-2-methylpropanoic acid and the title compound of Preparation 89 in a manner similar to that of Preparation 90. MS (E+) m/z: 435 (M+H); LCMS retention time: 1.71 min (Method 8).

Preparation 93

The title compound was prepared from the (S)-2-(2-chloro-5H-chromeno [2,3-b]pyridin-5-yl)-2-methylpropanoic acid and the title compound of Preparation 88 in a manner similar to that of Preparation 90. MS (E+) m/z: 459 (M+H); LCMS retention time: 1.65 min (Method 8).

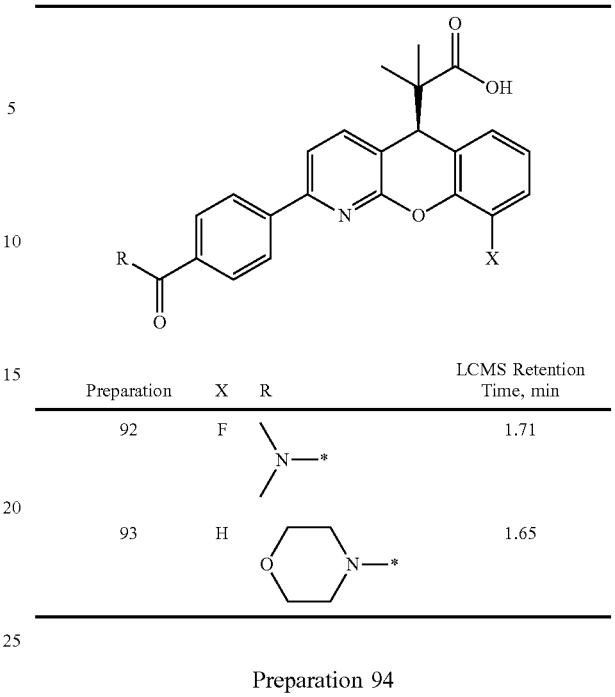

| Preparation | X | R | LCMS Retention Time, min |
|---|---|---|---|
| 92 | F | (dimethylamino)— * | 1.71 |
| 93 | H | (morpholino)— * | 1.65 |

Preparation 94

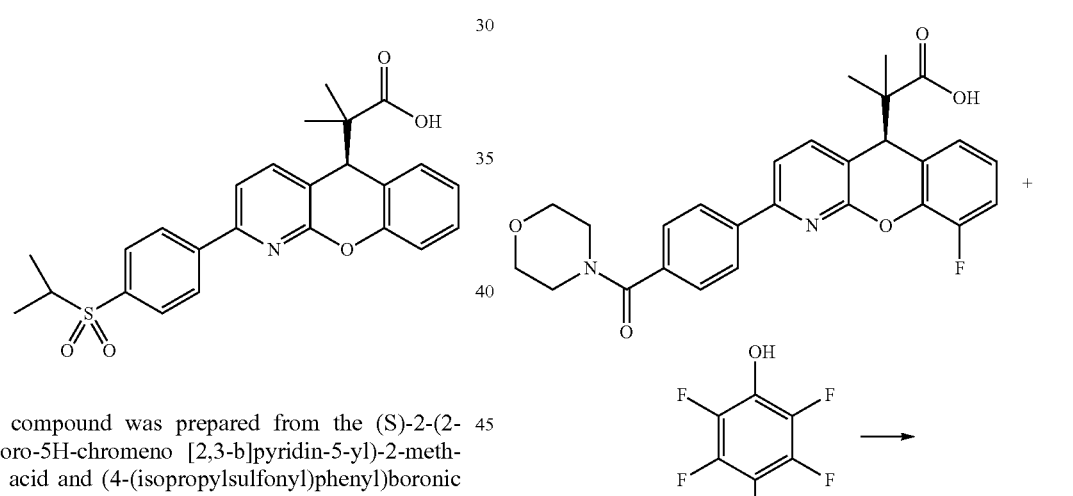

To a solution of the product of Preparation 90 (100 mg, 0.021 mmol) in anhydrous DMF (2 mL) at 0° C. was added pentafluorophenol (77 mg, 0.0419 mmol) and 1,3-dicyclohexylcarbodiimide (866 mg, 0.0419 mmol). The resulted mixture was stirred at room temperature for 2 h. The reaction mixture was concentrated and diluted with dichloromethane and filtered. The organic layer was washed with 10% sodium bicarbonate solution, water, brine solution, dried over anhydrous sodium sulfate, concentrated and purified by column chromatography (60-120 silica gel, 1-2% EtOAc/hexane) provided the product (100 mg, 74% yield) as a colorless oil. MS (E+) m/z: 643 (M+H); LCMS retention time: 3.36 min (Method 8).

Preparation 95

The title compound was prepared from the title compound of Preparation 92 in a manner similar to that of the preparation of the title compound of Preparation 94. MS (E+) m/z: 511 (M+H); LCMS retention time: 3.45 min (Method 8).

Preparation 96

The title compound was prepared from the title compound of Preparation 93 in a manner similar to that of the preparation of the title compound of Preparation 94. MS (E+) m/z: 625 (M+H); LCMS retention time: 3.50 min (Method 8).

| Preparation | X | R | LCMS Retention Time, min |
|---|---|---|---|
| 95 | F | N(CH3)2— | 3.45 |
| 96 | H | morpholine-N— | 3.50 |

Preparation 97

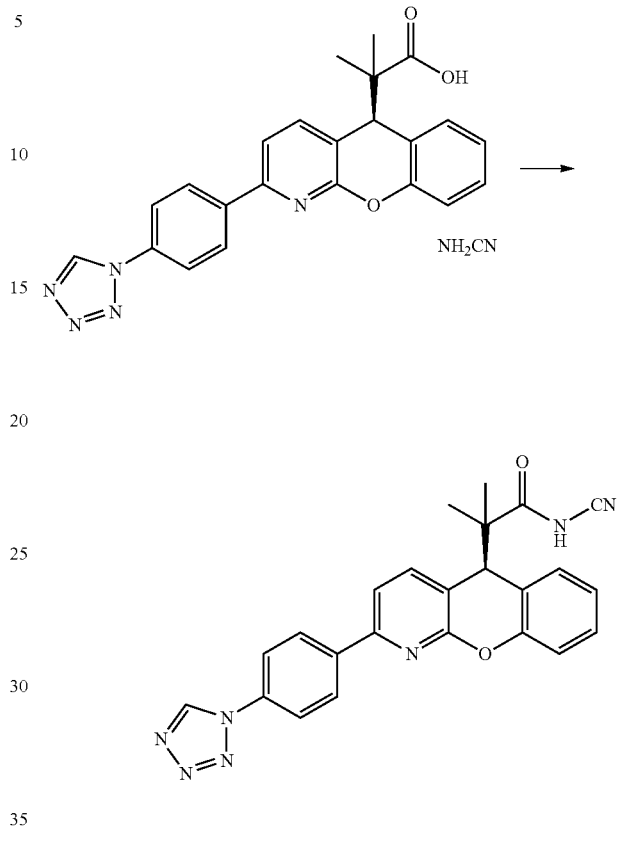

To the mixture of the product of Preparation 46 (40 mg, 0.097 mmol) in DMF, BOP (64.2 mg, 0.145 mmol) and DIEA (0.051 mL, 0.290 mmol) then cyanamide (8.13 mg, 0.194 mmol). The mixture was stirred at 75° C. for o/n. The mixture was added water (10 ml), extracted with AcOEt (40 ml), the mixture was washed with saturated $NH_4Cl$ (2×20 ml), dried and concentrated under vacuo to give the desired crude compound which was used as is.

Preparation 98

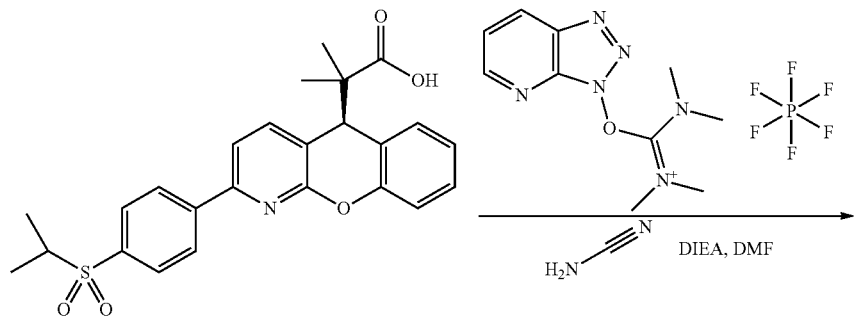

-continued

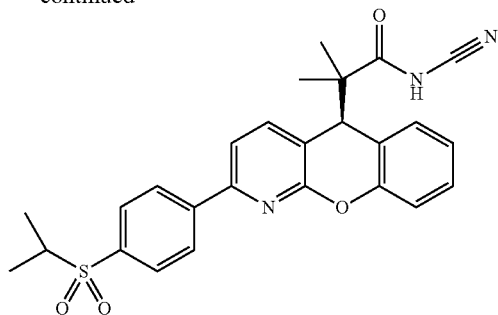

The title compound was prepared in a manner similar to that of the preparation of the title compound of Preparation 97. MS (E+) m/z: 511 (M+H); LCMS retention time: 3.45 min.

Preparation 99

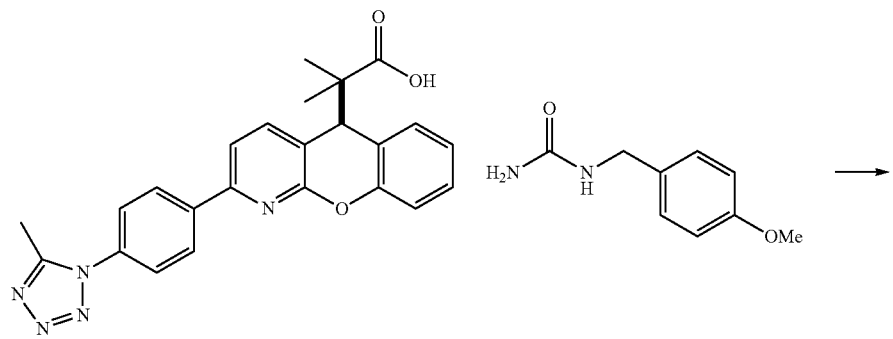

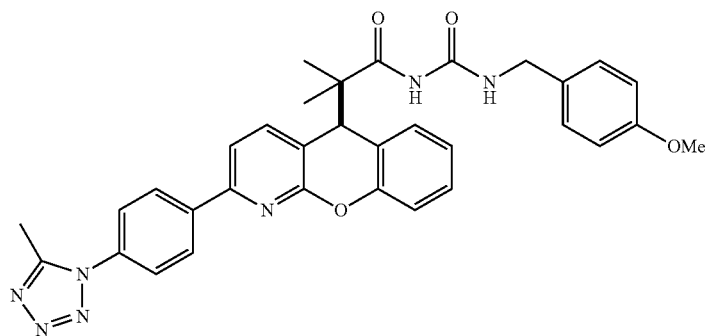

To a solution of the product from Preparation 47 (45 mg, 0.105 mmol) in THF (10 mL) was added methylsulfonyl chloride (12.31 µL, 0.158 mmol), DIEA (55.2 µL, 0.316 mmol), and stirred at room temperature for 1 h followed by 1-(4-methoxybenzyl)urea (37.9 mg, 0.211 mmol) and stirred at room temperature for 16 h. The reaction mixture was diluted with water and EtOAc. The aq layer was collected, acidified with 1N HCl, extracted with EtOAc. The organic layer was collected and tried on a ROTAVAPOR® to give the desired product. MS (E+) m/z: 590.2 (M+H); LC retention time: 3.49 min.

Preparations 100 to 114

The following compounds were prepared from the products of Preparations 23, 8, 9 to 17, 45, and 48 in a similar manner to that used for the preparation of the title compound of Preparation 23.

| Preparation | X | Y | Z | HPLC Retention Time, min |
|---|---|---|---|---|
| 100 | morpholine-C(=O)- | CH | H | 3.60 |
| 101 | morpholine-N- | CH | F | 3.67 |
| 102b | SO₂Et | CH | F | 3.63 |
| 103 | SO₂iPr | CH | F | 3.74 |
| 104 | SO₂Me | CH | F | 3.54 |
| 105 | OiPr | CH | F | 4.13 |
| 106 | OiPr | CF | F | 4.12 |
| 107 | C(CH₃)₂OH | CH | F | 3.80 |
| 108 | morpholine-N- | N | F | 2.47 |
| 109 | H | CH | F | |
| 110 | iBu | CH | F | |
| Preparation | X | Y | Z | HPLC Retention Time, min |
|---|---|---|---|---|
| 111 | tetrazole-N- | CH | F | 2.47 |
| 112 | pyrrolidine-C(=O)- | N | F | 3.72 |
| 113 | OiPr | CH | F | |
| 114 | morpholine-C(=O)- | N | F | 3.50 |
Preparation 115
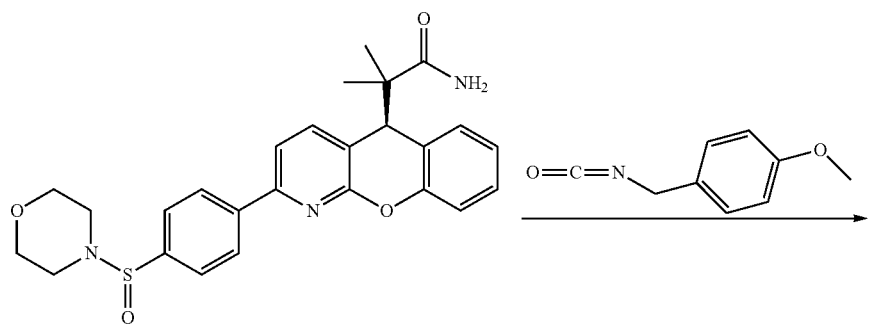
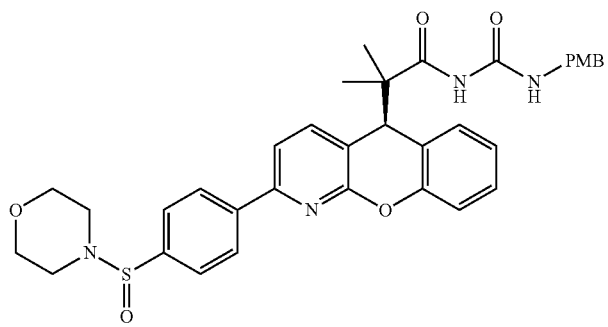

To a soln of the product of Preparation 7 (30 mg, 0.063 mmol) in toluene (1 mL) was added 1-(isocyanatomethyl)-4-methoxybenzene (21.4 mg, 0.131 mmol). The resulting mixture was heated at 90° C. for 12 h, then purified by preparative HPLC to provide the title compound (25 mg, 61% yield) as a white powder. MS (E+) m/z: 621.1 (M+H); LC retention time: 3.62 min.

All HPLC retention times were determined by Method 1, unless otherwise indicated.

Example 1

Step 1

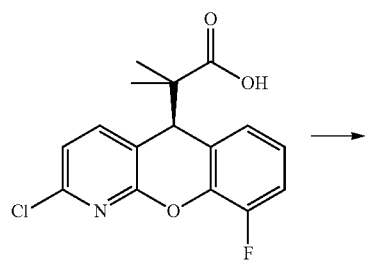

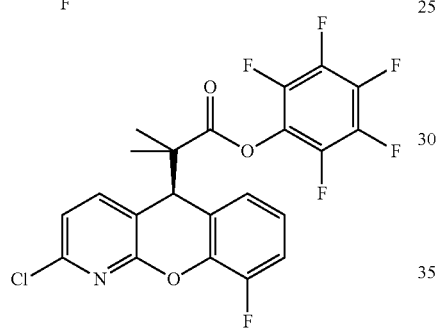

To a solution of (S)-2-(2-chloro-9-fluoro-5H-chromeno[2,3-b]pyridine-5-yl)-2-methylpropanoic acid (300 mg, 0.932 mmol) in DMF (2 mL) was added N,N'-dicyclohexylcarbodiimide (289 mg, 1.399 mmol) and pentafluorophenol (343 mg, 1.865 mmol). The resulted mixture was stirred at rt for 2 h. Water (2 mL) was added to the mixture, which was then extracted with dichloromethane, dried over sodium sulfate and concentrated. Flash column chromatography (40 g silica gel, 20%-50% EtOAc in hexanes) provided the product (350 mg, 77%) as a light yellow solid. MS (E+) m/z: 488 (M+H); LC retention time: 4.00 min.

Step 2

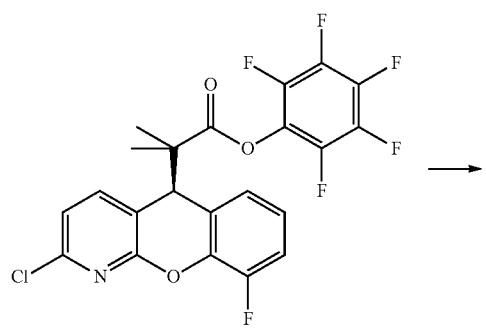

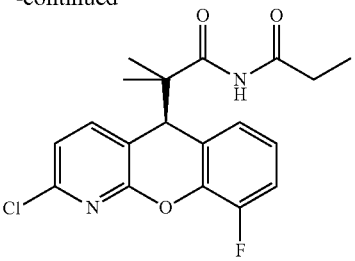

To a solution of propionamide (59.9 mg, 0.820 mmol) in THF (8 mL) at 0° C. was added sodium bis(trimethylsilyl)amide (1.025 mL, 1.025 mmol) dropwise. After stirring at 0° C. for 30 min, the product of Step 1 (200 mg, 0.410 mmol) was added portionwise. The resulted mixture was kept stirring at 0° C. for 30 min and then at ambient temperature for 1 h. The reaction was quenched with 1N HCl. Purification by preparative HPLC provided the product (95 mg, 47% yield) as a white powder. MS (E+) m/z: 377 (M+H); LC retention time: 2.91 min. Proton NMR (400 MHz, CDCl$_3$) δ ppm 1.07 (d, J=4.77 Hz, 6H) 1.17 (t, J=7.28 Hz, 3H) 2.87 (q, J=7.28 Hz, 2H) 4.54 (s, 1H) 6.97 (d, J=7.78 Hz, 1H) 7.03-7.16 (m, 3H) 7.18 (d, J=7.78 Hz, 1H) 7.58 (d, 1H).

Example 2

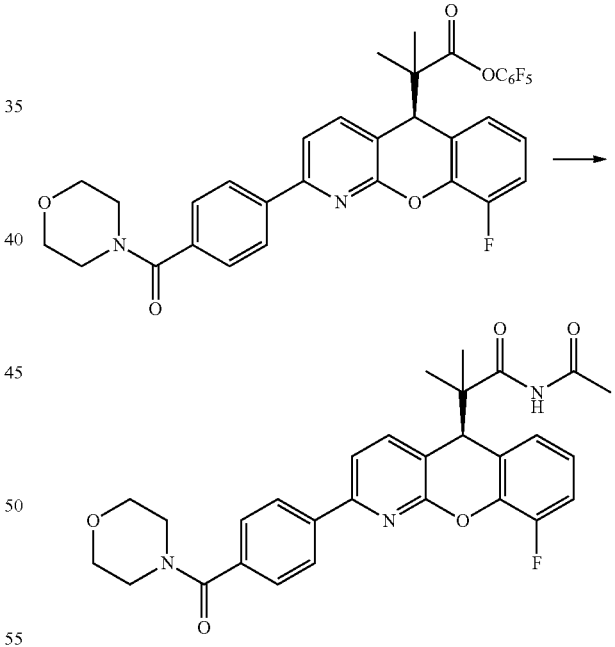

To a solution of trimethylsilylacetamide (30 mg, 0.233 mmol) in anhydrous THF (2 mL) at −78° C. was added sodium bis(trimethylsilylamide) (1M in THF) (0.23 mL, 0.233 mmol) and the reaction mixture was stirred for 30 min. Then a solution of the product of Preparation 94 (100 mg, 0.155 mmol) in anhydrous THF (1 mL) was added dropwise at −78° C. and the reaction mixture was allowed to room temperature slowly and stirred for overnight. The resulting reaction mixture was quenched with water (2 mL) and extracted with ethyl acetate. The organic layer was washed with water, brine, dried over anhydrous sodium sulfate, concentrated and purified by column chromatography (60-120 silica gel, 0.5%-1% methanol/chloroform) provided the title compound (20 mg, 25% yield) as a white solid. MS (E+) m/z: 518 (M+H); LC retention time: 9.54 min (Method 2 and 3); ¹H-NMR (400 MHz, CDCl₃): δ 0.97 (d, J=6.40 Hz, 6H), 2.52 (s, 3H), 3.48-3.66 (m, 8H), 4.57 (s, 1H), 7.01 (d, J=7.60 Hz, 1H), 7.06-7.08 (m, 1H), 7.14-7.14 (m, 1H), 7.52-7.54 (m, 5H), 7.70 (d, J=7.60 Hz, 2H).

Example 3

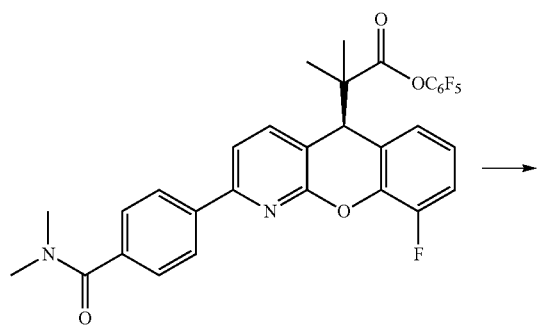

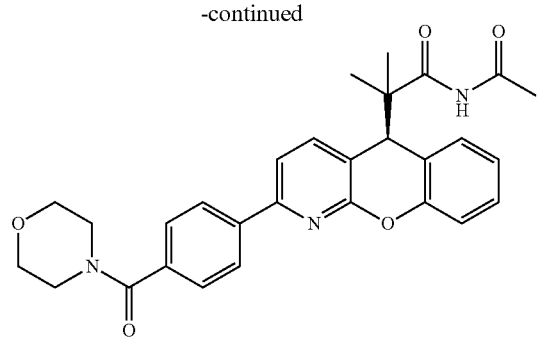

The title compound was prepared from the title compound of Preparation 89 in a manner similar to that of the preparation of the title compound of Example 2. MS (E+) m/z: 500 (M+H); LC retention time: 8.52 min (Method 2 and 3); ¹H-NMR (400 MHz, CDCl₃): δ 1.13 (s, 6H), 2.54 (s, 3H), 3.50-3.68 (m, 8H), 4.53 (s, 1H), 7.17-7.25 (m, 4H), 7.54-7.56 (m, 3H), 7.71 (d, J=7.60 Hz, 1H), 7.81 (s, 1H), 8.12 (d, J=7.60 Hz, 2H).

Example 5

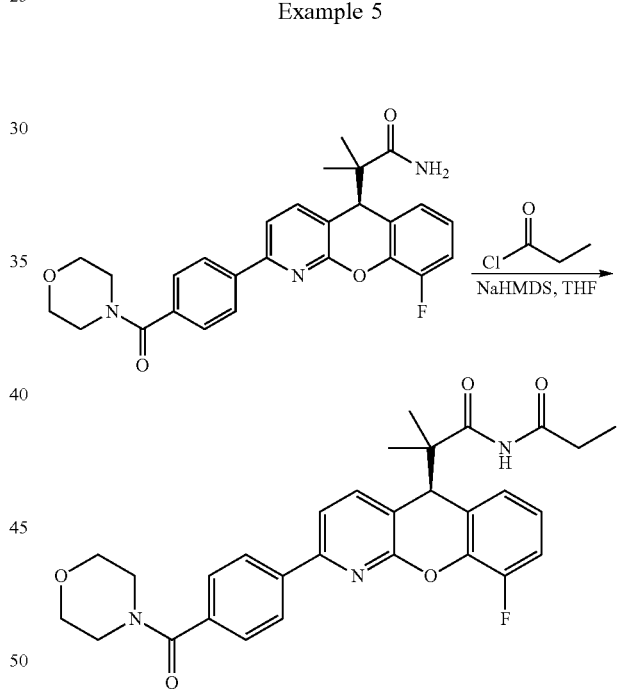

The title compound was prepared from the title compound of Preparation 95 in a manner similar to that of the preparation of the title compound of Example 2. MS (E+) m/z: 476 (M+H); LC retention time: 8.78 min (Method 2 and 3); ¹H-NMR (400 MHz, DMSO-d₆): δ 0.93 (d, J=3.96 Hz, 6H), 2.32 (s, 3H), 2.97 (d, J=25.28 Hz, 6H), 4.81 (s, 1H), 7.08 (d, J=6.32 Hz, 1H), 7.16-7.17 (m, 1H), 7.32-7.32 (m, 1H), 7.51-7.52 (m, 2H), 7.82 (d, J=7.88 Hz, 1H), 7.91-7.94 (m, 1H), 8.17 (d, J=8.36 Hz, 2H), 10.67 (s, 1H).

Example 4

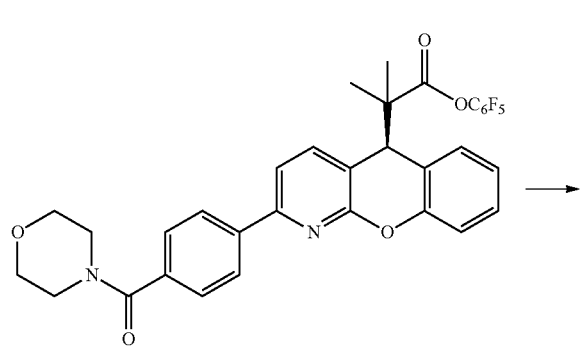

To a soln of the product of Preparation 7 (50 mg, 0.105 mmol) and propionyl chloride (0.018 mL, 0.210 mmol) in THF (2 mL) at 0° C. were added sodium bis(trimethylsilyl) amide (0.210 mL, 0.210 mmol) dropwise. The resulted mixture was kept stirring at 0° C. for 30 min and then at room temperature for 1 h. The reaction was quenched with the addition of 1N HCl. Purification by preparative HPLC provided the title compound (45 mg, 66% yield) as a white powder. MS (E+) m/z: 532.1 (M+H); LC retention time: 3.01 min. Proton NMR (400 MHz, CDCl₃) δ ppm 1.06-1.21 (m, 9H) 2.88 (q, J=7.19 Hz, 2H) 3.42-3.95 (m, 8H) 4.58 (s, 1H) 7.00 (d, J=7.53 Hz, 1H) 7.04-7.20 (m, 2H) 7.53 (d, J=7.78 Hz, 2H) 7.61 (d, J=7.78 Hz, 1H) 7.72 (d, J=7.78 Hz, 1H) 8.11 (d, 2H).

Examples 6 to 9

The title compounds of Examples 6 to 9 were prepared in a manner similar to the preparation of the title compound of Example 4, using the products of Preparations 7 and 8.

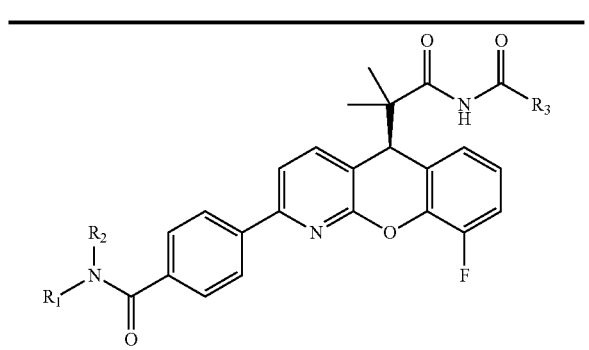

| Example | NR₁R₂ | R₃ | HPLC Retention Time, min | MS (E+) m/z |
|---|---|---|---|---|
| 6 | morpholine-N—* | CH(CH₃)₂ | 3.08 | 546.1 |
| 7 | morpholine-N—* | cyPr | 9.39 (Method 2) | 544.1 |
| 8 | pyrrolidine-N—* | Me | 3.08 | 502.1 |
| 9 | morpholine-N—* | cyBu | 3.22 | 558.1 |

| Example | Proton NMR* |
|---|---|
| 6 | 1.07-1.16 (m, 6 H) 1.18 (d, J = 7.03 Hz, 6 H) 3.32-3.41 (m, 1 H) 3.46-3.94 (m, 8 H) 4.58 (s, 1 H) 6.99-7.04 (m, 1 H) 7.04-7.19 (m, 3 H) 7.53 (d, J = 8.28 Hz, 2 H) 7.60 (d, J = 7.78 Hz, 1 H) 7.73 (d, J = 7.78 Hz, 1 H) 7.96-8.03 (m, 1 H) 8.11 (d, J = 8.28 Hz, 2 H) |
| 7 | 1.04-1.24 (m, 10 H) 2.74-2.85 (m, 1 H) 3.46-3.94 (m, 8 H) 4.59 (s, 1 H) 7.00-7.06 (m, 1 H) 7.06-7.21 (m, 2 H) 7.53 (d, J = 8.28 Hz, 2 H) 7.61 (d, J = 7.78 Hz, 1 H) 7.78 (d, J = 7.78 Hz, 1 H) 8.09 (d, J = 8.28 Hz, 2 H) |
| 8 | 1.12 (d, J = 3.26 Hz, 6 H) 1.89-2.07 (m, 4 H) 2.52 (s, 3 H) 3.50 (t, J = 6.15 Hz, 2 H) 3.72 (t, J = 6.90 Hz, 2 H) 4.57 (s, 1 H) 7.01 (s, 1 H) 7.05-7.20 (m, 2 H) 7.60-7.67 (m, 3 H) 7.71 (dd, J = 7.78, 3.51 Hz, 1 H) 7.87-7.95 (m, 1 H) 8.13 (t, J = 8.53 Hz, 2 H) |
| 9 | 1.10 (d, J = 1.51 Hz, 6 H) 1.91 (d, J = 6.78 Hz, 1 H) 1.96-1.97 (m, 2 H) 1.98-2.13 (m, 1 H) 2.25-2.36 (m, 4 H) 3.43-3.94 (m, 8 H) 4.56 (s, 1 H) 6.98 (d, J = 7.53 Hz, 1 H) 7.04-7.19 (m, 3 H) 7.53 (d, J = 8.28 Hz, 2 H) 7.57-7.62 (m, 1 H) 7.71 (d, J = 7.78 Hz, 1 H) 7.95 (s, 1 H) 8.04-8.04 (m, 1 H) 8.10 (d, J = 8.28 Hz, 2 H) |

*(400 MHz, CDCl₃) δ ppm

Example 10

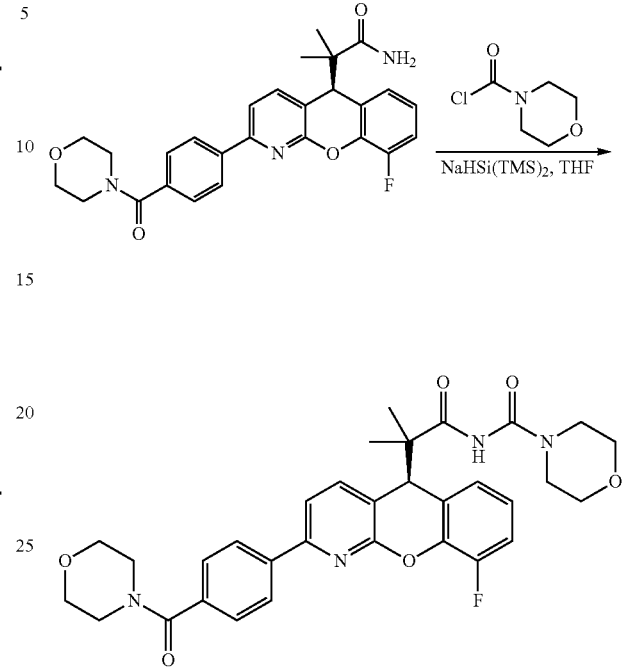

The title compound was prepared from the product of Preparation 7 in the same manner as the title compound of Example 4. MS (E+) m/z: 589.2 (M+H); LC retention time: 2.78 min. Proton NMR (400 MHz, CDCl₃) δ ppm 1.11 (s, 6H) 3.35-3.95 (m, 16H) 4.59 (s, 1H) 6.97-7.04 (m, 1H) 7.04-7.19 (m, 2H) 7.52 (d, J=8.28 Hz, 2H) 7.60 (d, J=7.78 Hz, 1H) 7.73 (d, J=8.03 Hz, 1H) 8.11 (d, J=8.53 Hz, 2H).

Examples 11 to 13

The title compounds of Examples 11 to 13 were prepared in a manner similar to the preparation of the title compound of Example 10, using the products of Preparations 7, 2, 8 to 9, and 11.

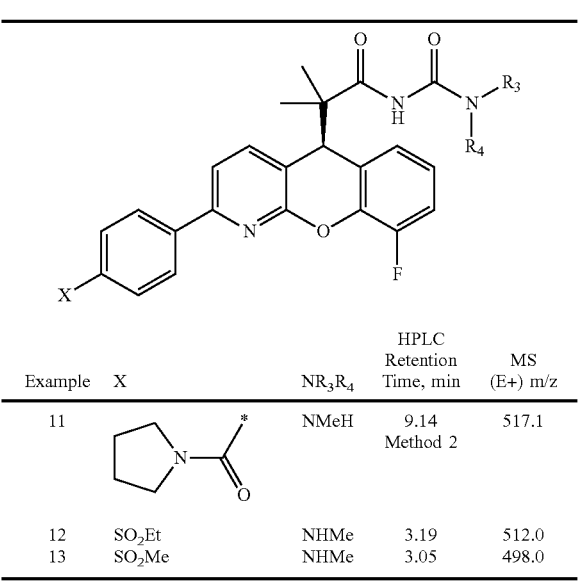

| Example | X | NR₃R₄ | HPLC Retention Time, min | MS (E+) m/z |
|---------|---|-------|--------------------------|-------------|
| 11 | 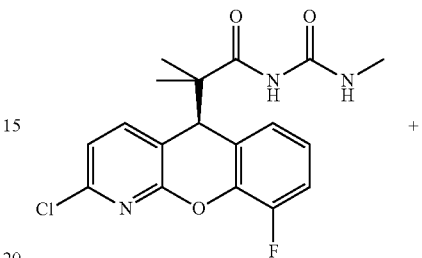 | NMeH | 9.14 Method 2 | 517.1 |
| 12 | SO₂Et | NHMe | 3.19 | 512.0 |
| 13 | SO₂Me | NHMe | 3.05 | 498.0 |

| Example | Proton NMR* |
|---------|-------------|
| 11 | 1.11 (d, J = 3.51 Hz, 6 H) 1.88-2.08 (m, 4 H) 2.95 (d, J = 4.77 Hz, 3 H) 3.49 (t, J = 6.53 Hz, 2 H) 3.71 (t, J = 6.90 Hz, 2 H) 4.54 (s, 1 H) 6.98 (d, J = 7.78 Hz, 1 H) 7.04-7.19 (m, 2 H) 7.58-7.66 (m, 3 H) 7.68-7.74 (m, 1 H) 8.12 (d, J = 8.28 Hz, 2 H) 8.62 (br. s., 1 H) 8.65-8.67 (m, 1 H) 8.68 (d, J = 4.77 Hz, 1 H) |
| 12 | 1.12 (s, 6 H) 1.31 (t, J = 7.48 Hz, 3 H) 2.97 (d, J = 4.84 Hz, 3 H) 3.17 (q, J = 7.48 Hz, 2 H) 4.54 (s, 1 H) 6.99 (d, J = 7.70 Hz, 1 H) 7.06-7.21 (m, 2 H) 7.66-7.69 (m, 1 H) 7.73-7.77 (m, 1 H) 8.02 (d, J = 8.58 Hz, 2 H) 8.27 (d, J = 8.58 Hz, 2 H) |
| 13 | 1.10-1.16 (m, 6 H) 2.98 (d, J = 4.62 Hz, 3 H) 3.13 (s, 3 H) 4.54 (s, 1 H) 6.99 (d, J = 7.70 Hz, 1 H) 7.08-7.22 (m, 3 H) 7.67-7.71 (m, 1 H) 7.73-7.77 (m, 1 H) 8.07 (d, J = 8.58 Hz, 2 H) 8.29 (d, J = 8.58 Hz, 2 H) |

*(400 MHz, CDCl₃) δ ppm

LC retention time: 2.85 min. Proton NMR (400 MHz, CDCl₃) δ ppm 1.07 (d, J=8.05 Hz, 6H) 2.94 (d, J=4.99 Hz, 3H) 4.55 (s, 1H) 6.98 (d, J=7.77 Hz, 1H) 7.04-7.20 (m, 3H) 7.58 (d, J=8.05 Hz, 1H) 8.55 (d, J=4.72 Hz, 1H) 8.66 (s, 1H).

Example 15

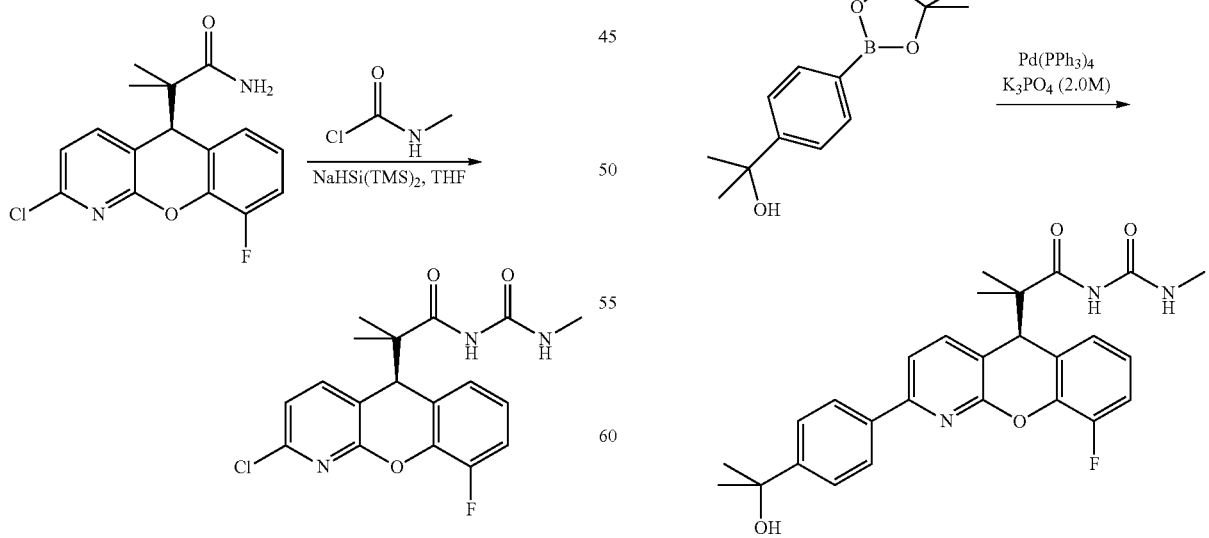

Example 14

The title compound was prepared from the product of Preparation 2 in the same manner as the preparation of the title compound of Example 10. MS (E+) m/z: 378.0 (M+H);

To a solution of the title compound of Example 14 (25 mg, 0.066 mmol) in DMF (1 ml) was added the product of Preparation 21 (26.0 mg, 0.099 mmol) and potassium phosphate tribasic monohydrate (0.099 ml, 0.199 mmol). Bubbled argon through for 10 min. and then palladium tetrakis (7.65 mg, 6.62 μmol) was added. After bubbling argon for another 5 min., the reaction vessel was sealed and heated to 90° C. for 4 h. The reaction mixture was filtered (syringe tip PTFE filter) and purified by preparative HPLC to provide the title compound (10 mg, 26% yield) as a white powder. MS (E+) m/z: 478.0 (M+H); LC retention time: 3.21 min. Proton NMR (400 MHz, CDCl$_3$) δ ppm 1.09 (d, J=4.52 Hz, 6H) 1.63 (s, 6H) 2.96 (d, J=4.52 Hz, 3H) 4.48 (s, 1H) 6.95 (d, J=7.53 Hz, 1H) 7.03-7.19 (m, 2H) 7.59 (d, J=8.03 Hz, 3H) 7.64-7.69 (m, 1H) 8.02 (d, J=8.28 Hz, 2H).

Examples 16 to 18

The title compounds of Examples 16 to 18 were prepared in a manner similar to the preparation of the title compound of Example 15.

| Example | Ar | HPLC Retention Time, min | MS (E+) m/z |
|---|---|---|---|
| 16 | (4-isopropoxyphenyl) | 12.31 Method 2 | 478.1 |
| 17 | (6-isopropoxypyridin-3-yl) | 3.75 | 479.2 |
| 18 | (2-(4-methylpiperazin-1-yl)pyrimidin-5-yl) | 2.46 | 520.2 |

Example 19

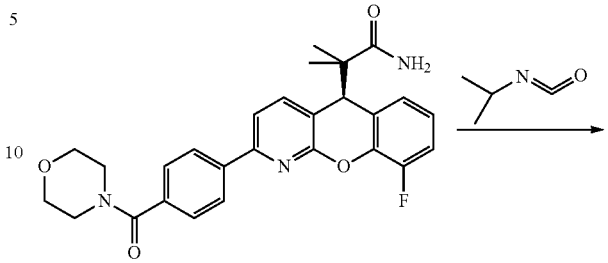

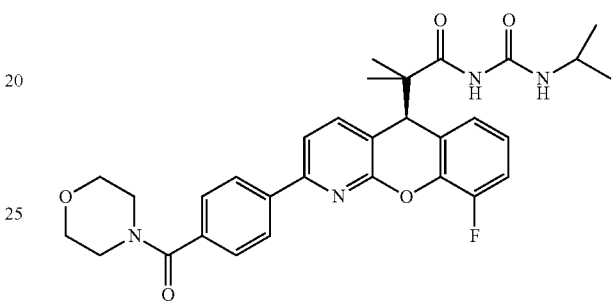

To a soln of the product of Preparation 7 (30 mg, 0.063 mmol) in toluene (1 mL) was added 2-isocyanatopropane (6.44 mg, 0.076 mmol). The resulting mixture was heated at 80° C. for 12 h, then purified by preparative HPLC to provide the title compound (13 mg, 31% yield) as a white powder. MS (E+) m/z: 561.1 (M+H); LC retention time: 3.29 min. Proton NMR (400 MHz, CDCl$_3$) δ ppm 1.11 (d, J=8.28 Hz, 6H) 1.28 (d, J=6.53 Hz, 6H) 3.42-3.94 (m, 8H) 4.00-4.13 (m, 1H) 4.50 (s, 1H) 6.97 (d, J=7.78 Hz, 1H) 7.08 (td, J=7.97, 4.89 Hz, 1H) 7.12-7.19 (m, 1H) 7.53 (d, J=8.53 Hz, 2H) 7.61 (d, J=7.78 Hz, 1H) 7.70 (d, J=7.78 Hz, 1H) 8.12 (d, J=8.53 Hz, 2H) 8.72 (d, J=7.53 Hz, 1H) 8.85 (s, 1H).

Examples 20 to 25

The title compounds of Examples 20 to 25 were prepared in a manner similar to the preparation of the title compound of Example 19), using the products of Preparations 7 and 10, and commercially available isocyanates.

| Example | Proton NMR* |
|---|---|
| 16 | 1.10 (d, J = 9.24 Hz, 6 H) 1.38 (d, J = 6.16 Hz, 6 H) 2.96 (d, J = 4.62 Hz, 3 H) 4.49 (s, 1 H) 4.60-4.71 (m, 1 H) 6.93-7.01 (m, 3 H) 7.03-7.18 (m, 2 H) 7.53 (d, J = 7.92 Hz, 1 H) 7.63 (d, J = 7.70 Hz, 1 H) 7.99 (d, J = 9.02 Hz, 2 H) 8.68-8.76 (m, 2 H) |
| 17 | 1.09 (d, J = 5.94 Hz, 6 H) 1.43 (d, J = 6.16 Hz, 6 H) 2.96 (d, J = 4.84 Hz, 3 H) 4.53 (s, 1 H) 5.21-5.33 (m, 1 H) 6.92 (d, J = 8.80 Hz, 1 H) 6.98 (d, J = 7.70 Hz, 1 H) 7.05-7.19 (m, 2 H) 7.58 (d, J = 7.92 Hz, 1 H) 7.64-7.69 (m, 1 H) 8.56 (dd, J = 8.80, 2.42 Hz, 1 H) 8.60-8.69 (m, 2 H) 8.91 (d, 1 H) |
| 18 | 1.05-1.13 (m, 6 H) 2.92 (s, 3 H) 2.96 (d, J = 4.99 Hz, 3 H) 3.49-3.61 (m, 2 H) 3.74 (d, J = 11.37 Hz, 2 H) 4.47 (s, 1 H) 5.04 (d, J = 14.43 Hz, 2 H) 6.96 (d, J = 7.77 Hz, 1 H) 7.06-7.19 (m, 3 H) 7.47 (d, J = 7.77 Hz, 1 H) 7.64 (d, J = 7.77 Hz, 1 H) 8.62-8.70 (m, 1 H) |

*(400 MHz, CDCl$_3$) δ ppm

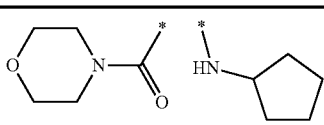

| Example | X | NR₃R₄ | HPLC Retention Time, min | MS (E+) m/z |
|---|---|---|---|---|
| 20 | 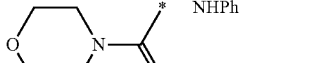 | 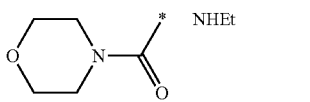 | 3.49 | 587.1 |
| 21 | 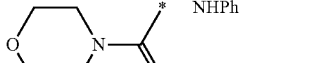 | NHPh | 3.72 | 595.2 |
| 22 | 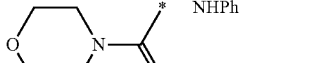 | NHEt | 3.34 | 547.1 |
| 23 | 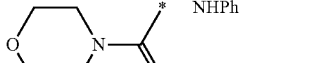 | NHBu | 3.68 | 545.2 |
| 24 | 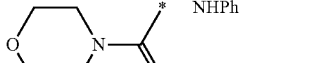 | NHCH₂(4-OMe)Ph | 3.60 | 639.1 |
| 25 | $SO_2iPr$ | NHMe | 3.33 | 526.0 |

| Example | Proton NMR* |
|---|---|
| 20 | 1.11 (d, J = 9.79 Hz, 6 H) 1.50-1.83 (m, 6 H) 1.98-2.10 (m, 2H) 3.43-3.94 (m, 8 H) 4.14-4.26 (m, 1 H) 4.49 (s, 1 H) 6.96 (d, J = 7.78 Hz, 1 H) 7.04-7.20 (m, 2 H) 7.53 (d, J = 8.53 Hz, 2 H) 7.61 (d, J = 7.78 Hz, 1 H) 7.72 (d, J = 8.03 Hz, 1 H) 8.10 (d, J = 8.53 Hz, 2 H) 8.90 (d, J = 7.28 Hz, 1 H) 9.12 (s, 1 H) |
| 21 | 1.17 (d, J = 3.33 Hz, 6 H) 3.45-3.93 (m, 6 H) 4.59 (s, 1 H) 7.01 (d, J = 7.77 Hz, 1 H) 7.06-7.24 (m, 3 H) 7.39 (t, J = 7.91 Hz, 3 H) 7.53 (dd, J = 7.91, 4.58 Hz, 4 H) 7.61 (d, J = 7.77 Hz, 1 H) 7.74 (d, J = 7.77 Hz, 1 H) 8.10 (d, J = 8.32 Hz, 2 H) 8.83 (s, 1 H) 10.86 (s, 1 H) |
| 22 | 1.12 (d, J = 5.52 Hz, 6 H) 1.26 (t, J = 7.15 Hz, 3 H) 3.41 (dd, J = 7.28, 5.77 Hz, 2 H) 3.45-3.95 (m, 8 H) 4.53 (s, 1 H) 6.98 (d, J = 7.78 Hz, 1 H) 7.04-7.20 (m, 2 H) 7.53 (d, J = 8.53 Hz, 2 H) 7.61 (d, J = 7.78 Hz, 1 H) 7.72 (d, J = 8.03 Hz, 1 H) 8.12 (d, J = 8.28 Hz, 2 H) 8.82 (t, 1 H) 9.02 (s, 1 H) |
| 23 | 0.88-1.03 (m, 3 H) 1.11 (d, J = 3.96 Hz, 6 H) 1.30-1.68 (m, 4 H) 3.32-3.42 (m, 2 H) 3.42-3.94 (m, 8 H) 4.55 (s, 1 H) 6.94-7.01 (m, 1 H) 7.02-7.22 (m, 2 H) 7.53 (d, J = 8.36 Hz, 2 H) 7.60 (d, J = 7.70 Hz, 1 H) 7.71 (d, J = 7.92 Hz, 1 H) 8.12 (d, J = 8.36 Hz, 2 H) 8.79 (t, J = 5.61 Hz, 1 H) 8.91 (s, 1 H) |
| 24 | 1.12 (d, J = 7.92 Hz, 6 H) 3.43-3.95 (m, 13 H) 4.54 (s, 1 H) 6.91-6.96 (m, 1 H) 7.06 (d, J = 4.62 Hz, 1 H) 7.17 (s, 1 H) 7.55 (dd, J = 8.03, 2.75 Hz, 3 H) 7.64-7.71 (m, 2 H) 8.13 (d, J = 8.36 Hz, 2 H) |
| 25 | 1.12 (s, 6 H) 1.33 (d, J = 7.04 Hz, 6 H) 2.96 (d, J = 4.84 Hz, 3 H) 3.20-3.29 (m, 1 H) 4.55 (s, 1 H) 6.99 (d, J = 7.70 Hz, 1 H) 7.06-7.21 (m, 2 H) 7.65-7.70 (m, 1 H) 7.72-7.76 (m, 1 H) 7.99 (d, J = 8.58 Hz, 2 H) 8.27 (d, 2 H) |

*(400 MHz, CDCl₃) δ ppm

Example 26

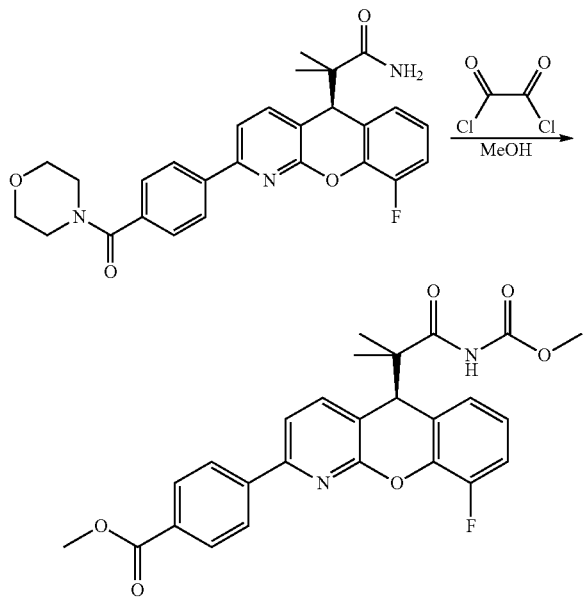

Example 27

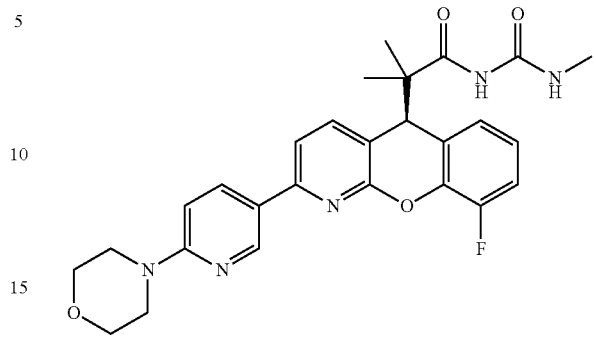

The title compound was prepared from the title product of Preparation 58 in a manner similar to that of the preparation of the title compound of Example 12. MS (E+) m/z: 506.1 (M+H); LC retention time: 2.60 min. Proton NMR (400 MHz, CDCl₃) δ ppm 1.10 (d, J=12.10 Hz, 6H) 2.96 (d, J=4.62 Hz, 3H) 3.77-3.86 (m, 4H) 3.89-4.01 (m, 4H) 4.55 (s, 1H) 7.01 (d, J=7.70 Hz, 1H) 7.08-7.22 (m, 3H) 7.63-7.76 (m, 2H) 8.70 (d, 1H) 8.76-8.91 (m, 2H).

Example 28

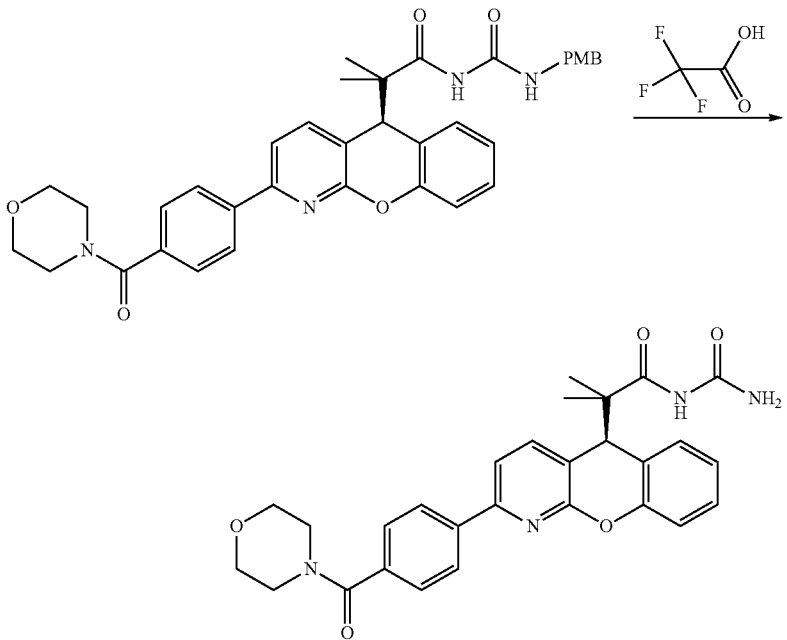

To a solution of the product of Preparation 7 (30 mg, 0.063 mmol) in 1,2-dichloroethane (2 mL) was added oxalyl chloride (0.055 mL, 0.631 mmol) dropwise. The mixture was heated at reflux (90° C.) for 16 h. Purification by preparative HPLC provides the title compound (15 mg, 40% yield) as a white powder. MS (E+) m/z: 479.1 (M+H); LC retention time: 3.46 min. Proton NMR (400 MHz, CDCl₃) δ ppm 1.12 (d, J=14.81 Hz, 6H) 3.77 (s, 3H) 3.96 (s, 3H) 4.66 (s, 1H) 7.03-7.20 (m, 3H) 7.56 (br. s., 1H) 7.65 (d, J=7.78 Hz, 1H) 7.80 (d, J=7.78 Hz, 1H) 8.07-8.18 (m, 4H).

The solution of the title compound of Preparation 115 (20 mg, 0.032 mmol) in trifluoroacetic acid (1 mL, 12.98 mmol) was heated at 50° C. for 12 h. The reaction mixture was concentrated and the residue was dissolved in THF and purified by preparative HPLC to provide the title compound (15 mg, 76% yield) as a white powder. MS (E+) m/z: 501.2 (M+H); LC retention time: 2.94 min. Proton NMR (400 MHz, CDCl₃) δ 8.56 (d, J=3.1 Hz, 1H), 8.32 (s, 1H), 8.05-7.98 (m, 2H), 7.63 (d, J=7.9 Hz, 1H), 7.54-7.43 (m, 3H), 7.33-7.22 (m, 2H), 7.16-7.05 (m, 2H), 5.98 (br. s., 1H), 4.41 (s, 1H), 3.86-3.39 (m, 8H), 1.05 (s, 6H).

Example 29

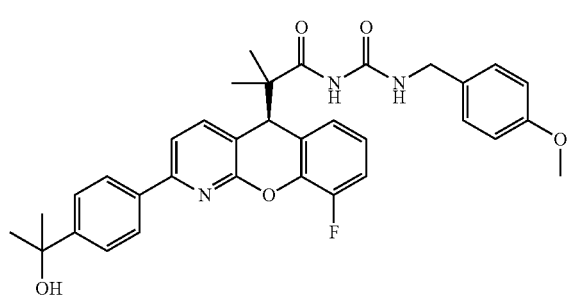 [SMILES: COc1ccc(CNC(=O)NC(=O)C(C)(C)[C@@H]2c3ccc(-c4ccc(C(C)(C)O)cc4)nc3Oc3c(F)cccc32)cc1]

The title compound was prepared from the products of Preparation 22 and Preparation 23 in the same manner as the title compound of Example 15. MS (E+) m/z: 584.2 (M+H); LC retention time: 3.80 min. Proton NMR (400 MHz, CDCl$_3$) δ ppm 1.03 (d, J=5.72 Hz, 6H) 1.56 (s, 6H) 3.76 (s, 3H) 4.37-4.44 (m, 3H) 6.81-6.90 (m, 3H) 6.95 (d, J=4.84 Hz, 1H) 7.03-7.11 (m, 1H) 7.16-7.24 (m, 2H) 7.42-7.59 (m, 4H) 7.95 (d, 2H).

Examples 30 to 67

The title compounds of Examples 30 to 67 were prepared from the products of Preparations 37 to 43, 73 to 83, and 99 to 114 in a manner similar to the preparation of the title compound of Example 28.

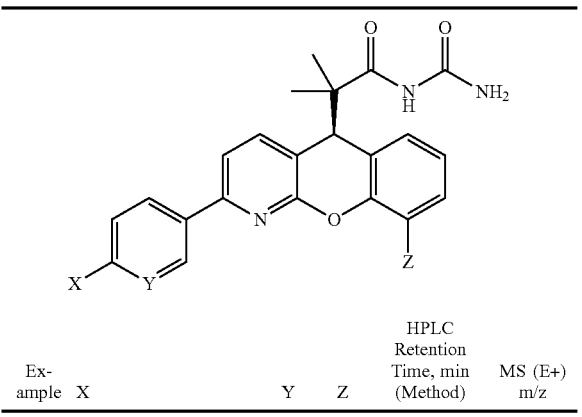

| Example | X | Y | Z | HPLC Retention Time, min (Method) | MS (E+) m/z |
|---|---|---|---|---|---|
| 30 | pyrrolidine-carbonyl | CH | F | 3.19 | 503.2 |
| 31 | SO$_2$Et | CH | F | 3.02 | 498.0 |
| 32 | SO$_2$iPr | CH | F | 3.19 | 512.1 |
| 33 | SO$_2$Me | CH | F | 2.90 | 484.0 |
| 34 | OiPr | CH | F | 3.68 | 464.1 |
| 35 | OiPr | CF | F | 3.71 | 482.1 |
| 36 | OiPr | CH | H | 17.49 (4) | 446.0 |
| 37 | Ph | CH | H | 9.99 (3) | 388.0 |
| 38 | iBu | CH | H | 19.61 (4) | 442.2 |
| 39 | SO$_2$Et | CH | H | 9.30 (3) | 480.2 |

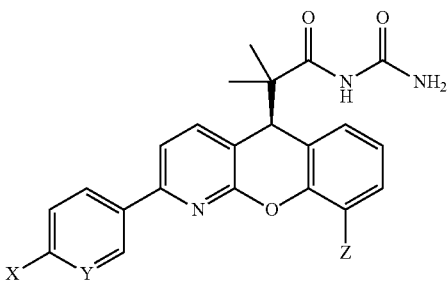

| Example | X | Y | Z | HPLC Retention Time, min (Method) | MS (E+) m/z |
|---|---|---|---|---|---|
| 40 | pyrrolidine-carbonyl | CH | H | 9.12 (3) | 485.2 |
| 41 | morpholine | N | F | 2.47 | 492.3 |
| 42 | Ph | CH | F | 16.49 (4) | 406.2 |
| 43 | iBu | CH | F | 20.20 (4) | 462.2 |
| 44 | morpholine-carbonyl | CF | H | 8.61 (3) | 519.2 |
| 45 | tetrazolyl | CH | F | 8.06 (5) | 474.4 |
| 46 | pyrrolidine-carbonyl | N | F | 3.13 (5) | 504.3 |
| 47 | OiPr | CF | H | 17.27 (4) | 464.3 |
| 48 | morpholine-carbonyl | N | F | 2.82 | 520.3 |
| 49 | 3,3-difluoropyrrolidine-carbonyl | CF | H | 9.53 (2 and 3) | 539 |
| 50 | 3,3-difluoropyrrolidine-carbonyl | CH | H | 9.22 (2 and 3) | 521 |
| 51 | pyrrolidine-carbonyl | CF | H | 9.34 (2 and 3) | 501 |

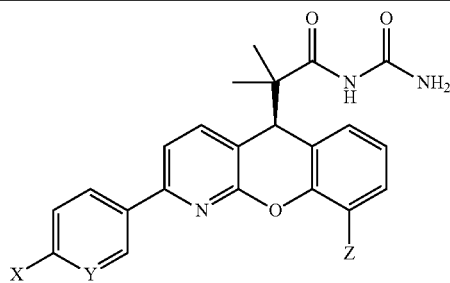

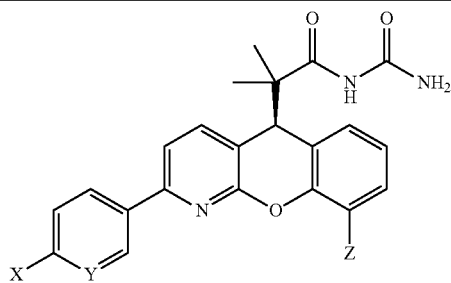

| Example | X | Y | Z | HPLC Retention Time, min (Method) | MS (E+) m/z |
|---|---|---|---|---|---|
| 52 | pyrrolidine-carbonyl | CCl | H | 10.23 (2 and 3) | 519 |
| 53 | 3,3-difluoropyrrolidine-carbonyl | CCl | H | 9.90 (2 and 3) | 555 |
| 54 | pyrrolidine-carbonyl | N | H | 8.44 (2 and 3) | 486 |
| 55 | morpholine-carbonyl | N | H | 7.47 (2 and 3) | 502 |
| 56 | morpholine-carbonyl | CF | F | 14.27 (2 and 3) | 537 |
| 57 | C(CH$_3$)$_2$OH | N | H | 6.10 (2 and 3) | 447 |
| 58 | N(CH$_3$)$_2$ | N | H | 6.68 (3) | 432 |
| 59 | morpholine-N | N | H | 6.40 (2 and 3) | 474 |
| 60 | isopropyl-NH | N | F | 2.46 | 464.3 |
| 61 | acetamido (CH$_3$C(O)NH) | N | F | 2.79 | 464.2 |
| 62 | cyclopropyl-NH | N | F | 2.38 | 462.3 |
| 63 | HOC(O) | N | F | 3.15 | 450.1 |
| 64 | piperidin-1-yl | N | F | 2.58 | 490.2 |
| 65 | OiPr | N | H | 3.59 | 447.3 |
| 66 | acetamido (CH$_3$C(O)NH) | N | H | 7.37 (2 and 3) | 445.0 |
| 67 | 5-methyl-2H-tetrazol-2-yl | CH | H | 8.13 (2 and 3) | 470.1 |

| Example | Proton NMR* |
|---|---|
| 30 | 1.13 (d, J = 3.96 Hz, 6 H) 1.88-2.09 (m, 4 H) 3.45-3.56 (m, 2 H) 3.71 (t, J = 6.82 Hz, 2 H) 4.55 (s, 1 H) 5.80 (br. S., 1 H) 6.99 (d, J = 7.70 Hz, 1 H) 7.05-7.21 (m, 2 H) 7.64 (dd, J = 8.14, 2.20 Hz, 3 H) 7.68-7.74 (m, 1 H) 8.12 (d, J = 8.58 Hz, 2 H) 8.21 (s, 1 H) 8.54 (d, 1 H) |
| 31 | 1.15 (s, 6 H) 1.31 (t, J = 7.48 Hz, 3 H) 3.18 (q, J = 7.41 Hz, 2 H) 4.56 (s, 1 H) 6.99 (d, J = 7.70 Hz, 1 H) 7.07-7.23 (m, 2 H) 7.65-7.71 (m, 1 H) 7.72-7.78 (m, 1 H) 7.98-8.07 (m, 2 H) 8.23-8.31 (m, 2 H) 8.48 (s, 1 H) 8.65 (d, 1 H) |
| 32 | 1.15 (s, 6 H) 1.33 (d, J = 6.82 Hz, 6 H) 3.19-3.33 (m, 1 H) 4.55 (s, 1 H) 6.99 (d, J = 7.70 Hz, 1 H) 7.08-7.23 (m, 2 H) 7.64-7.72 (m, 1 H) 7.73-7.79 (m, 1 H) 7.95-8.04 (m, 2 H) 8.25 (d, J = 8.58 Hz, 2 H) 8.58 (s, 1 H) 8.67 (d, 1 H) |
| 33 | 1.15 (s, 6 H) 3.12 (s, 3 H) 4.56 (s, 1 H) 7.00 (d, J = 7.70 Hz, 1 H) 7.08-7.23 (m, 2 H) 7.65-7.71 (m, 1 H) 7.72-7.78 (m, 1 H) 8.03-8.10 (m, 2 H) 8.25-8.31 (m, 2 H) 8.34 (s, 1 H) 8.60 (br. S., 1 H) |
| 34 | 1.10-1.18 (m, 6 H) 1.38 (d, J = 6.16 Hz, 6 H) 4.51 (s, 1 H) 4.61-4.70 (m, 1 H) 6.94-7.02 (m, 3 H) 7.06-7.20 (m, 2 H) 7.54 (d, J = 7.92 Hz, 1 H) 7.67 (d, J = 7.92 Hz, 1 H) 7.93-7.97 (m, 2 H) 8.48 (s, 1 H) 8.67 (d, 1 H) |

-continued

| Example | Proton NMR* |
|---|---|
| 35 | 1.13 (d, J = 7.70 Hz, 6 H) 1.41 (d, J = 6.16 Hz, 6 H) 4.51 (s, 1 H) 4.60-4.71 (m, 1 H) 6.97 (d, J = 7.48 Hz, 1 H) 7.02-7.21 (m, 3 H) 7.52 (d, J = 7.92 Hz, 1 H) 7.68 (d, J = 7.92 Hz, 1 H) 7.72-7.81 (m, 2 H) 8.59 (s, 1 H) 8.70 (d, 1 H) |
| 41 | 1.13 (d, J = 4.72 Hz, 6 H) 3.77-3.84 (m, 4 H) 3.91-3.98 (m, 4 H) 4.54 (s, 1 H) 7.01 (d, J = 7.77 Hz, 1 H) 7.09-7.22 (m, 3 H) 7.65-7.70 (m, 1 H) 7.71-7.76 (m, 1 H) 8.82 (d, J = 1.66 Hz, 1 H) 8.88 (dd, 1 H) |
| 45 | 9.74 (1 H, s), 8.18-8.32 (2 H, m), 7.86-8.00 (2 H, m), 7.70-7.84 (2 H, m), 6.92-7.23 (3 H, m), 4.55 (1 H, s), 0.98 (6 H, d, J = 7.0 Hz) |
| 46 | 9.32 (1 H, d), 8.51-8.65 (2 H, m), 7.95 (1 H, d, J = 8.1 Hz), 7.73-7.79 (1 H, m), 7.66-7.73 (1 H, m), 7.08-7.23 (2 H, m), 7.00 (1 H, d, J = 7.7 Hz), 4.57 (1 H, s), 3.74 (4 H, q, J = 6.2 Hz), 1.91-2.07 (4 H, m), 1.14 (6 H, s) |
| 48 | 9.33 (1 H, d), 8.71 (1 H, dd, J = 8.1, 2.2 Hz), 7.68-7.88 (3 H, m), 7.09-7.25 (2 H, m), 7.02 (1 H, d, J = 7.7 Hz), 4.58 (1 H, s), 3.56-3.96 (8 H, m), 1.16 (6 H, d, J = 2.9 Hz), 1.08-1.24 (5 H, m) |
| 49 | **0.93 (s, 6H), 2.46-2.48 (m, 2H), 3.53-3.55 (m, 1H), 3.73-3.95 (m, 3H), 4.81 (s, 1H), 7.21-7.41 (m, 5H), 7.60-7.62 (m, 1H), 7.78 (d, J = 8.00 Hz, 1H), 7.83 (s, 1H), 7.98-8.09 (m, 3H), 10.24 (s, 1H) |
| 50 | **0.95 (s, 6H), 3.68-3.76 (m, 4H), 3.92-3.95 (m, 2H), 4.81 (s, 1H), 7.20-7.40 (m, 5H), 7.70-7.97 (m, 5H), 8.22 (d, J = 8.00 Hz, 2H), 10.26 (s, 1H). |
| 51 | **0.93 (s, 6H), 1.83-1.85 (m, 4H), 3.26 (t, J = 6.00 Hz, 2H), 3.50 (t, J = 6.80 Hz, 2H), 4.80 (s, 1H), 7.19-7.40 (m, 5H), 7.54-7.56 (m, 1H), 7.77 (d, J = 8.00 Hz, 1H), 7.84 (s, 1H), 7.96-7.98 (m, 3H), 10.23 (s, 1H). |
| 52 | **0.93 (s, 6H), 1.84-1.86 (m, 4H), 3.17 (t, J = 6.40 Hz, 2H), 3.53 (t, J = 6.80 Hz, 2H), 4.80 (s, 1H), 7.21-7.42 (m, 5H), 7.67 (d, J = 8.80 Hz, 1H), 7.76 (d, J = 8.00 Hz, 1H), 7.85 (s, 1H), 7.96-7.98 (m, 1H), 8.14 (s, 1H), 8.18-8.20 (m, 1H), 10.25 (s, 1H). |
| 53 | **0.93 (s, 6H), 2.46-2.47 (m, 2H), 3.43-3.78 (m, 3H), 3.96 (t, J = 13.20 Hz, 1H), 4.79 (s, 1H), 7.18-7.41 (m, 5H), 7.67-7.76 (m, 2H), 7.83 (s, 1H), 7.95-7.97 (m, 1H), 8.17-8.23 (m, 2H), 10.23 (s, 1H). |
| 54 | **0.94 (s, 6H), 1.87-1.88 (m, 4H), 3.55 (t, J = 6.80 Hz, 2H), 3.67 (t, J = 6.40 Hz, 2H), 4.82 (s, 1H), 7.20-7.42 (m, 5H), 7.80-7.87 (m, 3H), 8.04 (d, J = 7.60 Hz, 1H), 8.58-8.61 (m, 1H), 9.30 (s, 1H), 10.23 (s, 1H). |
| 55 | **0.94 (s, 6H), 3.32-3.70 (m, 8H), 4.82 (s, 1H), 7.20-7.42 (m, 5H), 7.74-7.84 (m, 3H), 8.03 (d, J = 7.60 Hz, 1H), 8.59-8.62 (m, 1H), 9.30 (d, J = 1.20 Hz, 1H), 10.22 (s, 1H). |
| 56 | **0.94 (s, 6H), 3.33-3.67 (m, 8H), 4.86 (s, 1H), 7.06-7.20 (m, 1H), 7.21-7.24 (m, 1H), 7.33-7.38 (m, 2H), 7.54-7.58 (m, 1H), 7.80-7.82 (m, 2H), 8.01-8.08 (m, 3H), 10.23 (s, 1H). |
| 57 | **0.93 (s, 6H), 4.80 (s, 1H), 5.32 (s, 1H), 7.18-7.38 (m, 5H), 7.75-7.94 (m, 4H), 8.43-8.45 (m, 1H), 9.17 (d, J = 2.40 Hz, 1H), 10.25 (s, 1H). |
| 58 | **0.92 (s, 6H), 3.12 (s, 6H), 4.74 (s, 1H), 6.75 (d, J = 8.80 Hz, 1H), 7.16-7.29 (m, 3H), 7.35-7.39 (m, 2H), 7.64 (d, J = 7.60 Hz, 1H), 7.74 (d, J = 8.00 Hz, 1H), 7.85 (s, 1H), 8.20-8.22 (m, 1H), 8.84 (d, J = 2.40 Hz, 1H), 10.21 (s, 1H). |
| 59 | **0.92 (s, 6H), 3.56-3.58 (m, 4H), 3.72-3.74 (m, 4H), 4.75 (s, 1H), 6.95 (d, J = 9.20 Hz, 1H), 7.17-7.39 (m, 5H), 7.67 (d, J = 4.00 Hz, 1H), 7.78 (d, J = 8.00 Hz, 1H), 7.84 (s, 1H), 8.25-8.27 (m, 1H), 8.88 (d, J = 2.40 Hz, 1H), 10.21 (s, 1H). |
| 60 | *8.75 (1 H, dd), 8.60-8.67 (2 H, m), 7.52 (1 H, d, J = 7.9 Hz), 7.08-7.22 (2 H, m), 7.00 (1 H, d, J = 7.7 Hz), 6.92 (1 H, d, J = 9.5 Hz), 4.52 (1 H, s), 1.40 (6 H, dd, J = 6.5, 2.1 Hz), 1.14 (6 H, d, J = 2.0 Hz) |
| 61 | *8.92 (1 H, s), 8.75 (2 H, br. S.), 7.75 (1 H, d, J = 7.5 Hz), 7.49-7.61 (2 H, m), 7.09-7.23 (2 H, m), 7.02 (1 H, d, J = 7.5 Hz), 4.59 (1 H, s), 2.37 (3 H, s), 1.13 (6 H, d, J = 17.6 Hz) |
| 62 | *8.74 (1 H, dd), 8.50-8.61 (2 H, m), 7.71 (1 H, d, J = 7.9 Hz), 7.49 (1 H, d, J = 7.7 Hz), 7.29 (1 H, d, J = 9.5 Hz), 7.08-7.22 (2 H, m), 7.00 (1 H, d, J = 7.7 Hz), 4.53 (1 H, s), 2.64-2.73 (1 H, m), 1.13 (6 H, d, J = 6.6 Hz), 0.96-1.05 (2 H, m), 0.77-0.85 (2 H, m) |
| 63 | *9.12 (1 H, s), 8.77 (1 H, d, J = 3.3 Hz), 8.00-8.12 (4 H, m), 7.65 (2 H, q, J = 7.8 Hz), 7.08-7.24 (2 H, m), 7.00-7.07 (1 H, m), 4.52 (1 H, s), 1.20 (6 H, d, J = 2.2 Hz) |
| 64 | ***8.67 (1 H, dd), 8.62 (1 H, d, J = 2.0 Hz), 7.89 (1 H, d, J = 8.1 Hz), 7.79 (1 H, d, J = 7.9 Hz), 7.52 (1 H, d, J = 9.5 Hz), 7.11-7.30 (3 H, m), 4.66 (1 H, s), 3.75-3.86 (4 H, m), 1.84 (6 H, br. S.), 1.11 (3 H, s), 1.06 (3 H, s) |
| 65 | *8.97 (1 H, d), 8.69 (1 H, dd, J = 8.9, 2.3 Hz), 7.70 (1 H, d, J = 7.9 Hz), 7.59 (1 H, d, J = 7.7 Hz), 7.29-7.40 (2 H, m), 7.20-7.25 (1 H, m), 7.12-7.20 (1 H, m), 7.04 (1 H, d, J = 8.8 Hz), 5.14-5.25 (1 H, m), 4.50 (1 H, s), 1.47 (6 H, d, J = 6.2 Hz), 1.11 (6 H, d, J = 2.4 Hz) |
| 66 | ***7.99-7.85 (m, 2H), 7.68 (d, J = 8.1 Hz, 1H), 7.64-7.51 (m, 3H), 7.36-7.13 (m, 3H), 7.08 (dd, J = 7.4, 1.2 Hz, 1H), 2.06 (s, 3H), 0.95 (d, J = 9.5 Hz, 6H) |
| 67 | ****¹H NMR (400 MHz, methanol-d₄) δ 8.27-8.21 (m, 2H), 7.79-7.70 (m, 2H), 7.67-7.63 (m, 2H), 7.33-7.22 (m, 2H), 7.18 (dd, J = 8.1, 1.1 Hz, 1H), 7.13-7.07 (m, 1H), 2.57 (s, 3H), 0.97 (d, J = 14.1 Hz, 6H) |

*(400 MHz, CDCl₃) δ ppm
**(400 MHz, DMSO-d₆) δ ppm
***(400 MHz, MeOD) δ ppm

Example 68

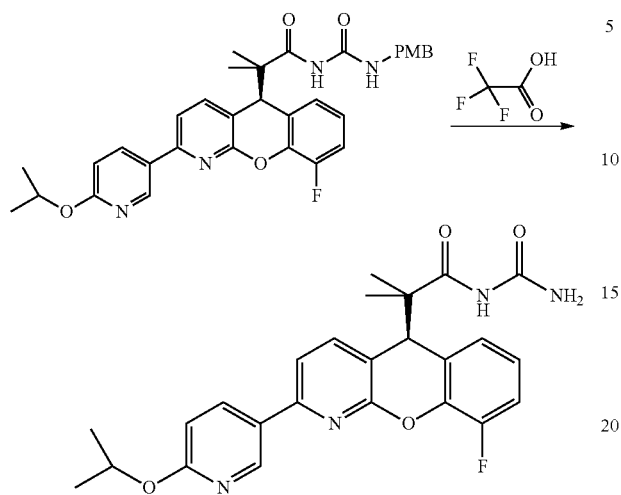

A solution of the product of Preparation 37 (60 mg, 0.115 mmol) in TFA (1 mL, 12.98 mmol) was stirred at 45° C. for 55 h. The solvent was removed in vacuo and the residue purified by preparative HPLC to provide the title compound (25 mg, 47% yield) as a white powder. MS (E+) m/z: 465.3 (M+H); LC retention time: 3.63 min. Proton NMR (400 MHz, CDCl$_3$) δ ppm 8.81 (1H, d, J=2.2 Hz), 8.39 (1H, d), 7.66 (1H, d, J=7.9 Hz), 7.54 (1H, d, J=7.9 Hz), 7.04-7.20 (2H, m), 6.99 (1H, d, J=7.7 Hz), 6.81 (1H, d, J=8.8 Hz), 5.30-5.39 (1H, m), 4.55 (1H, s), 1.40 (6H, d, J=6.2 Hz), 1.12 (6H, d, J=2.9 Hz).

Example 69

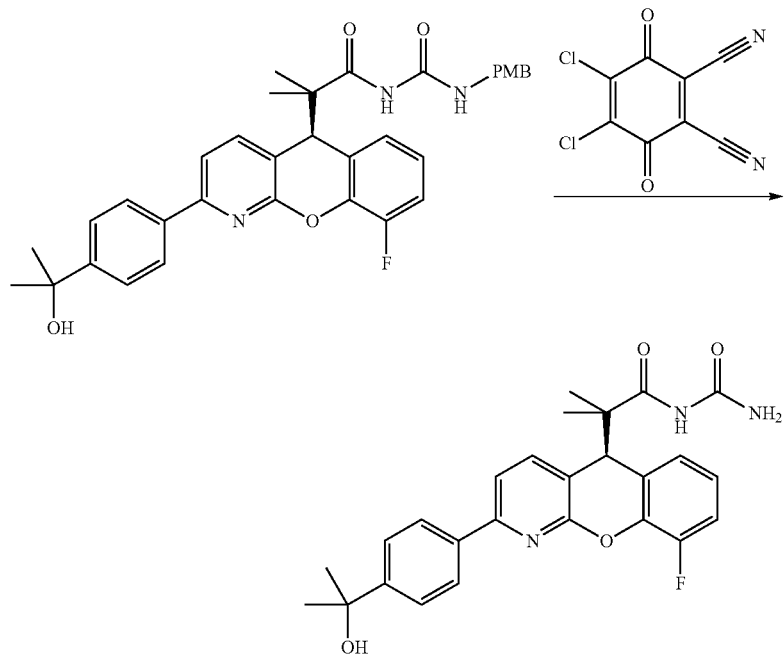

The solution of the product of Preparation 107 (10 mg, 0.017 mmol) in dichloromethane (1 mL) and water (0.050 mL) was added DDQ (5.83 mg, 0.026 mmol). The resulted mixture was stirred at 25° C. for 12 h. The solvent was removed in vacuo, and the residue purified by preparative HPLC to give the title compound (3 mg, 30% yield) as a white powder. MS (E+) m/z: 464.2 (M+H); LC retention time: 3.27 min. Proton NMR (400 MHz, CDCl$_3$) δ ppm 1.06 (d, J=7.70 Hz, 6H) 1.57 (s, 6H) 4.44 (s, 1H) 6.86-6.93 (m, 1H) 6.97-7.13 (m, 1H) 7.42 (d, J=8.36 Hz, 1H) 7.50-7.57 (m, 2H) 7.59-7.64 (m, 1H) 7.91-7.99 (m, 2H).

Example 70

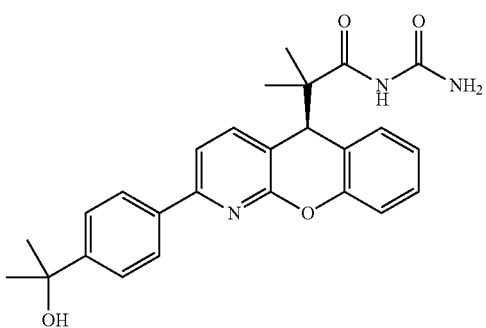 [SMILES: CC(C)(O)c1ccc(-c2ccc3c(n2)Oc2ccccc2[C@@H]3C(C)(C)C(=O)NC(N)=O)cc1]

The title compound was prepared from the product of Preparation 33 in a manner similar to the preparation of the title compound of Example 69. MS (E+) m/z: 446.0 (M+H); LC retention time: 9.29 min (Method 3).

Example 71

Step 1

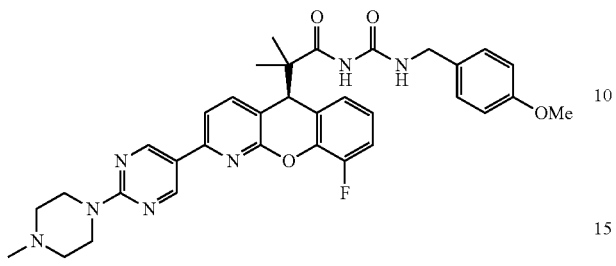

The product of Step 1 was prepared from the product of Preparation 19 in a similar manner as the title compound of Example 24). MS (E+) m/z: 626 (M+H); LC retention time: 3.05 min.

Step 2

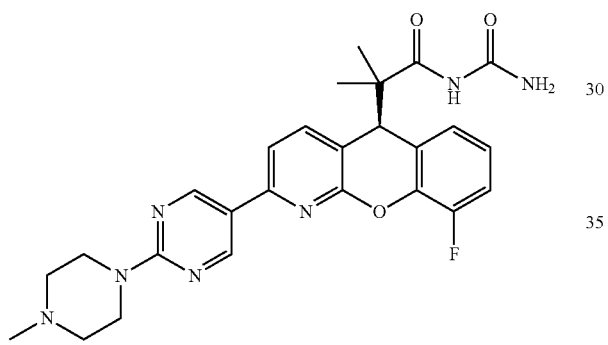

The title compound was prepared from the product of Step 1 in a manner similar to the preparation of the title compound of Example 28). MS (E+) m/z: 506.3 (M+H); LC retention time: 2.33 min. Proton NMR (400 MHz, CDCl$_3$) δ ppm 1.13 (d, J=5.94 Hz, 6H) 2.92 (s, 3H) 3.42-3.80 (m, 8H) 4.52 (s, 1H) 5.02 (d, 2H) 5.70 (br. s., 1H) 6.99 (d, J=7.70 Hz).

Example 72

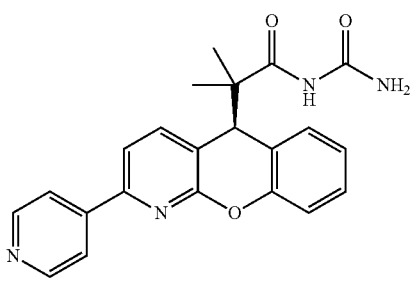 [SMILES: CC(C)(C(=O)NC(N)=O)[C@H]1c2ccccc2Oc2nc(-c3ccncc3)ccc21]

The title compound was prepared in a manner similar to the preparation of the title compound of Example 35. MS (E+) m/z: 389.2 (M+H); LC retention time: 6.31 min (Method 3).

Example 73

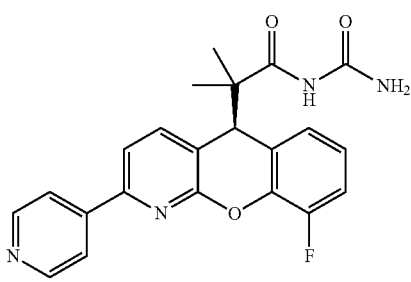 [SMILES: CC(C)(C(=O)NC(N)=O)[C@@H]1c2ccc(-c3ccncc3)nc2Oc2c(F)cccc21]

The title compound was prepared in a manner similar to the preparation of the title compound of Example 28. MS (E−) m/z: 405.0 (M−H); LC retention time: 5.69 min (Method 2).

Example 74

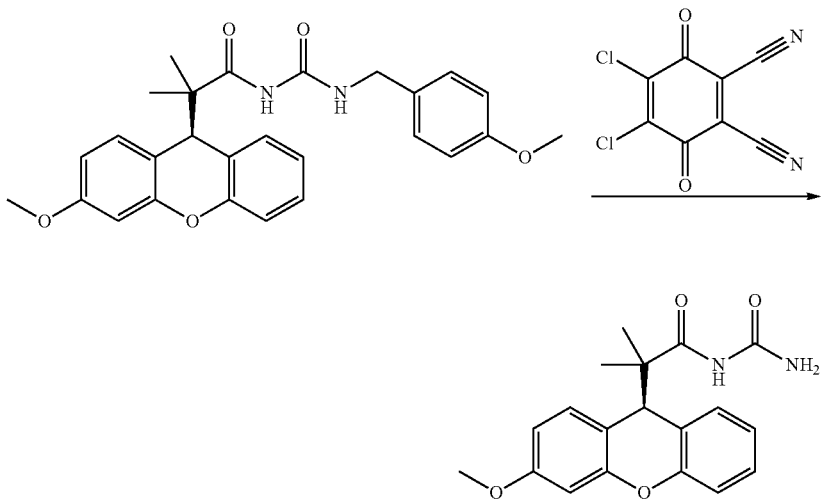

To a solution of the product of Preparation 24 (10 mg, 0.022 mmol) in dichloromethane (1 mL) and water (0.050 mL) was added DDQ (7.39 mg, 0.033 mmol). The resulting mixture was stirred at room temperature for 12 h. The solvent was removed and the residue purified by preparative HPLC to give the title compound (4 mg, 54% yield) as a white powder. MS (E+) m/z: 341.2 (M+H); LC retention time: 3.34 min. Proton NMR (400 MHz, CDCl$_3$) δ ppm 7.17-7.24 (1H, m), 6.96-7.13 (4H, m), 6.56-6.64 (2H, m), 4.22 (1H, s), 3.74 (3H, s), 0.99 (6H, d, J=4.4 Hz).

Example 75

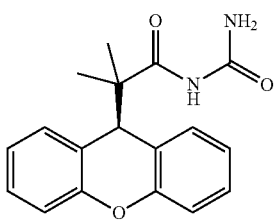

The title compound was prepared from the product of Preparation 25 in a manner similar to the preparation of the title compound of Example 74. MS (E+) m/z: 311.2 (M+H); LC retention time: 3.30 min. Proton NMR (400 MHz, CDCl$_3$) δ ppm 7.18-7.25 (2H, m), 7.10 (4H, ddd, J=14.7, 7.9, 1.3 Hz), 6.98-7.04 (2H, m), 4.29 (1H, s), 0.99 (6H, s).

Example 76

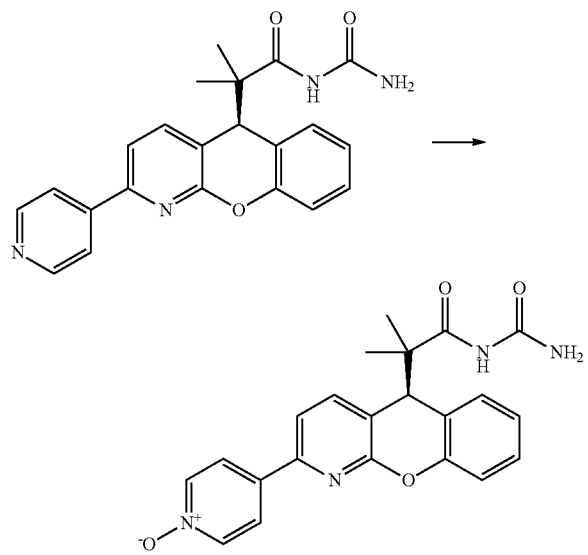

To the title compound of Example 72 (65 mg, 0.167 mmol) in chloroform (2 mL) at 0° C. was added m-chloroperbenzoic acid (52 mg, 0.334 mmol). The resulted mixture was stirred at room temperature for 2 h. The reaction mixture was diluted with chloroform and washed with 10% sodium bicarbonate solution, brine solution, dried over anhydrous sodium sulfate, concentrated and purified by preparative TLC using 5% methanol/chloroform as eluent to provide the title compound (15 mg, 22% yield) as a white solid. MS (E+) m/z: 405 (M+H); LC retention time: 6.38 min (Method 2 and 3); $^1$H-NMR (400 MHz, DMSO-d$_6$): δ 0.92 (s, 6H), 4.79 (s, 1H), 7.19-7.30 (m, 3H), 7.36-7.41 (m, 2H), 7.77 (d, J=8.00 Hz, 1H), 7.83 (s, 1H), 7.97 (d, J=8.00 Hz, 1H), 8.12 (d, J=7.20 Hz, 2H), 8.31 (d, J=7.20 Hz, 2H), 10.21 (s, 1H).

Example 77

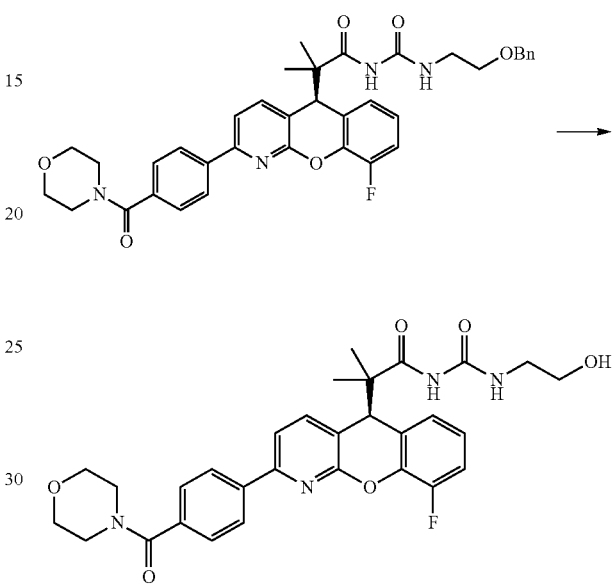

To a solution of title compound of Preparation 84 (40 mg, 0.0613 mmol) in anhydrous methanol (2 mL) was added 10% Pd/C (56 mg) and ammonium formate (6 mg, 0.092 mmol) in a miniclave hydrogenation at 100 psi pressure. The resulted mixture was stirred at 65° C. for 9 h. The reaction mixture was filtered through CELITE® bed, concentrated under vacuum and purification by preparative TLC (5% methanol/chloroform) to provided the title compound (10 mg, 29% yield) as a white solid. MS (E+) m/z: 563 (M+H); LC retention time: 12.15 min (Method 6); $^1$H-NMR (400 MHz, DMSO-d$_6$): δ 0.96 (s, 6H), 3.32-3.37 (m, 2H), 3.51 (q, J=5.20 Hz, 2H), 3.52-3.64 (m, 8H), 4.82 (t, J=5.20 Hz, 1H), 4.86 (s, 1H), 7.06-7.39 (m, 3H), 7.55-7.58 (m, 2H), 7.80 (d, J=8.00 Hz, 1H), 7.97 (d, J=8.00 Hz, 1H), 8.19-8.24 (m, 2H), 8.53-8.56 (m, 1H), 10.39 (s, 1H).

Example 78

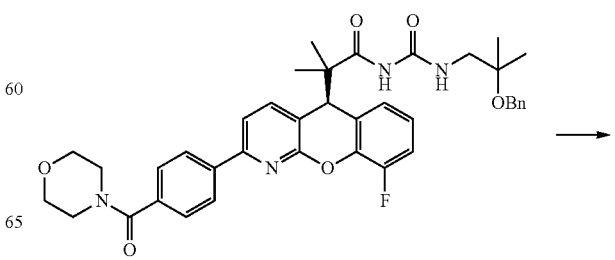

115

-continued

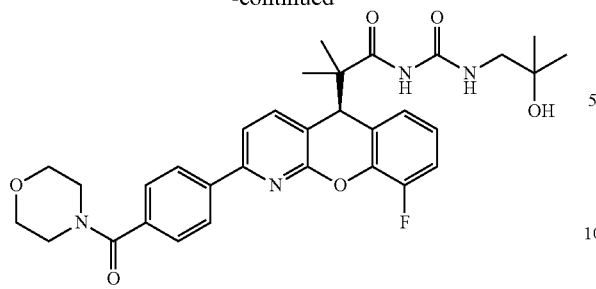

The title compound was prepared from the title compound of Preparation 85 in a manner similar to that of the preparation of the title compound of Example 77. MS (E+) m/z: 591 (M+H); LC retention time: 8.43 min (Method 3); $^1$H-NMR (400 MHz, DMSO-d$_6$): δ 0.95 (d, J=13.60 Hz, 6H), 1.30 (s, 6H), 3.19 (d, J=5.20 Hz, 2H), 3.50-3.72 (m, 8H), 4.60 (s, 1H), 4.86 (s, 1H), 7.05 (d, J=7.60 Hz, 1H), 7.15-7.20 (m, 1H), 7.32-7.39 (m, 2H), 7.56 (d, J=8.00 Hz, 1H), 7.79 (d, J=8.00 Hz, 1H), 7.94 (d, J=8.00 Hz, 1H), 8.19 (d, J=8.00 Hz, 2H), 8.60 (t, J=5.60 Hz, 1H), 10.38 (s, 1H).

Example 79

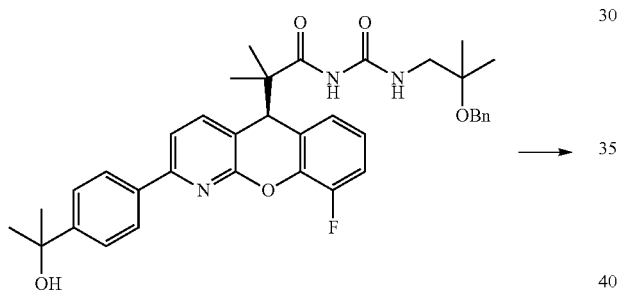

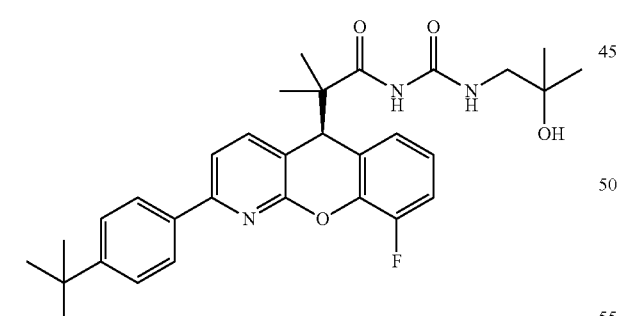

The title compound was prepared from the title compound of Preparation 86 in manner similar to that of the preparation of the title compound of Example 82. MS (E+) m/z: 536 (M+H); LC retention time: 9.04 min (Method 2 and 3); $^1$H-NMR (400 MHz, DMSO-d$_6$): δ 0.95 (d, J=11.60 Hz, 6H), 1.13 (s, 6H), 1.47 (s, 6H), 3.19 (d, J=5.60 Hz, 2H), 4.61 (s, 1H), 4.84 (s, 1H), 5.12 (s, 1H), 7.04 (d, J=7.60 Hz, 1H), 7.14-7.19 (m, 1H), 7.33-7.38 (m, 1H), 7.60 (d, J=8.40 Hz, 2H), 7.75 (d, J=8.00 Hz, 1H), 7.85 (d, J=8.00 Hz, 1H), 8.04 (d, J=8.40 Hz, 2H), 8.60 (t, J=5.60 Hz, 1H), 10.39 (s, 1H).

116

Example 80

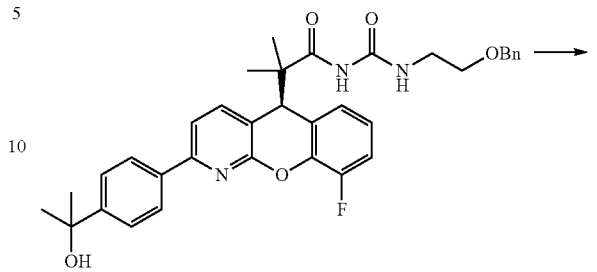

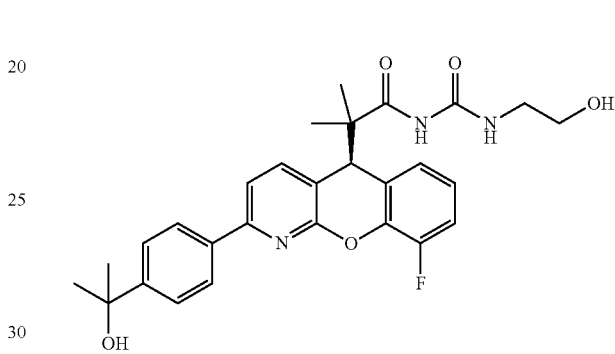

The title compound was prepared from the title compound of Preparation 87 in a manner similar to that of the preparation of the title compound of Example 77. MS (E+) m/z: 508 (M+H); LC retention time: 9.07 min (Method 2 and 3); $^1$H-NMR (400 MHz, DMSO-d$_6$): δ 0.94 (d, J=4.00 Hz, 6H), 1.47 (s, 6H), 3.28-3.31 (m, 2H), 3.51 (q, J=5.60 Hz, 2H), 4.81-4.84 (m, 2H), 5.11 (s, 1H), 7.04-7.06 (m, 1H), 7.17-7.22 (m, 1H), 7.33-7.37 (m, 1H), 7.59-7.61 (m, 2H), 7.74 (d, J=7.60 Hz, 1H), 7.88 (d, J=7.60 Hz, 1H), 8.05 (d, J=8.80 Hz, 2H), 8.53 (t, J=5.60 Hz, 1H), 10.39 (s, 1H).

Example 81

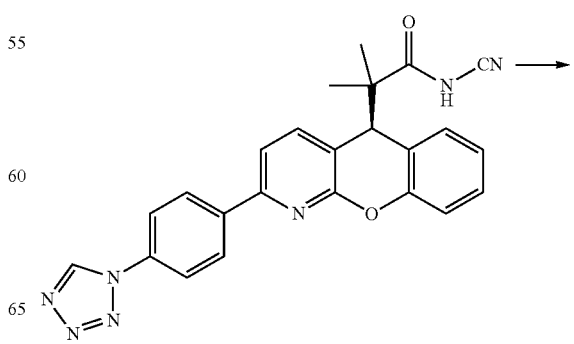

-continued

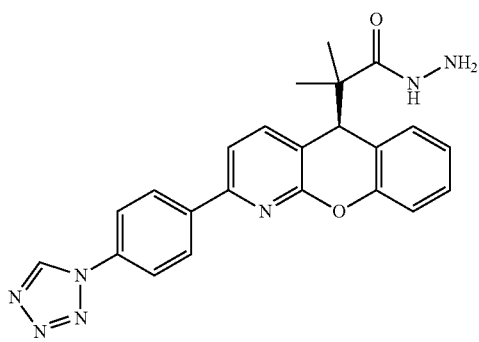

To the mixture of the product of Preparation 97 (30 mg, 0.069 mmol) in 2 mL 4N HCl/1,4-dioxane, water (0.5 ml) was added and the mixture was stirred at 50° C. for 2 h. The mixture was added water (10 mL), basified with $Na_2CO_3$ and extracted with AcOEt (40 mL), the mixture was washed with saturated $NaHCO_3$ (2×20 ml), dried and concentrated under vacuo and purified by prep-HPLC to give the desired compound (10 mg, 23% yield) as an off-white solid. MS (E+) m/z: 456.2 (M+H); LC retention time: 8.08 min (Method 2 and 3); $^1$H NMR (400 MHz, DMSO-$d_6$) δ 8.37-8.30 (m, 2H), 8.04-7.98 (m, 2H), 7.93 (d, J=7.7 Hz, 1H), 7.72 (d, J=7.9 Hz, 1H), 7.31 (dd, J=7.0, 1.5 Hz, 2H), 7.26-7.18 (m, 2H), 7.17-7.10 (m, 1H), 0.87 (s, 6H).

Example 82

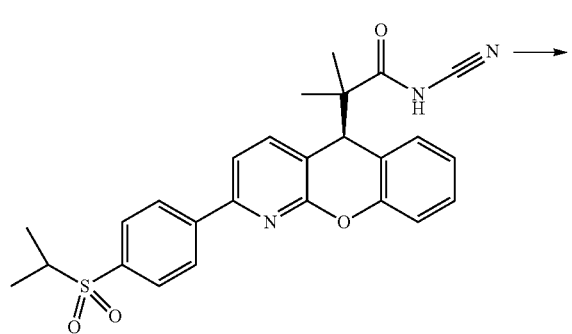

The title compound was prepared from the title compound of Preparation 98 in manner similar to that of the preparation of the title compound of Example 81. MS (E+) m/z: 494.2 (M+H); LC retention time: 9.77 min (Method 2 and 3); $^1$H-NMR (400 MHz, CDCl$_3$) δ ppm 8.21-8.29 (2H, m), 7.95-8.02 (2H, m), 7.70-7.76 (1H, m), 7.64 (1H, d, J=7.7 Hz), 7.32-7.41 (2H, m), 7.22-7.26 (1H, m), 7.14-7.21 (1H, m), 4.53 (1H, s), 3.19-3.30 (1H, m), 1.33 (6H, d, J=6.8 Hz), 1.12 (6H, d, J=12.8 Hz).

Example 83

Step 1

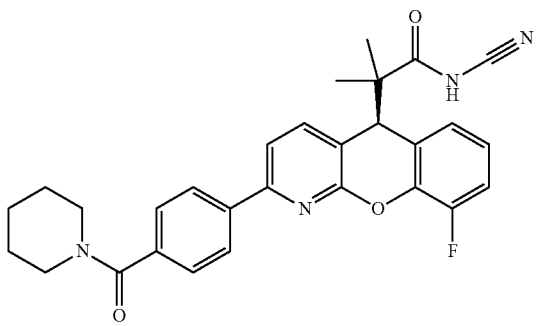 [SMILES: CC(C)(C(=O)NC#N)[C@@H]1c2ccc(-c3ccc(C(=O)N4CCCCC4)cc3)nc2Oc2c(F)cccc21]

The product of Step 1 was prepared from the product of Preparation 21 in a similar manner as the title compound of Preparation 49. MS (E+) m/z: 499.2 (M+H); LC retention time: 3.40 min.

Step 2

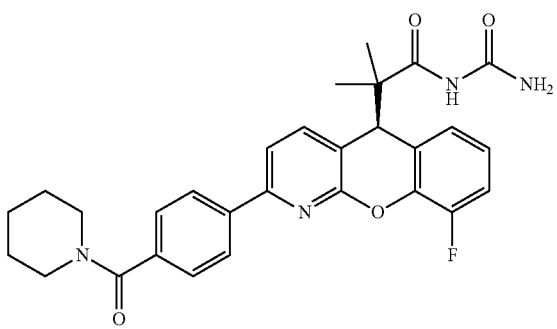 [SMILES: CC(C)(C(=O)NC(N)=O)[C@@H]1c2ccc(-c3ccc(C(=O)N4CCCCC4)cc3)nc2Oc2c(F)cccc21]

The title compound was prepared from product of step 1 in manner similar to that of the preparation of the title compound of Example 81. MS (E+) m/z: 517.2 (M+H); LC retention time: 3.38 min; $^1$H NMR (400 MHz, CDCl$_3$) δ ppm 8.13 (2H, d), 7.68-7.74 (1H, m), 7.61-7.66 (1H, m), 7.53 (2H, d, J=8.4 Hz), 7.07-7.22 (2H, m), 7.00 (1H, d, J=7.7 Hz), 4.56 (1H, s), 3.79 (2H, br. s.), 3.43 (2H, br. s.), 1.50-1.83 (6H, m), 1.14 (6H, d, J=2.9 Hz).

Example 84

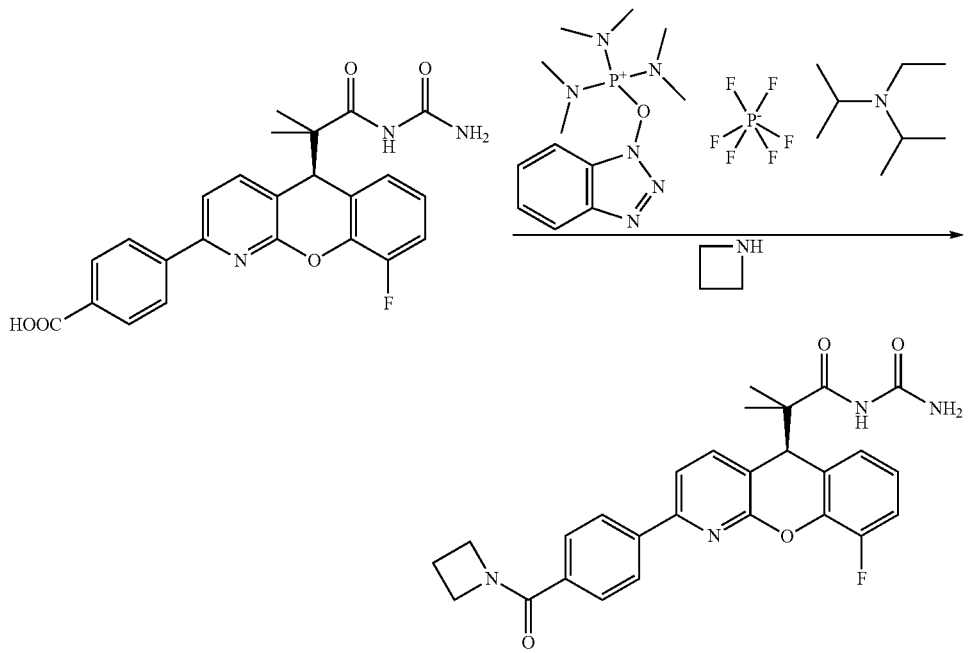

The title compound was prepared from Example 63 in a similar manner as the title compound of Preparation 49. MS (E+) m/z: 489.2 (M+H); LC retention time: 8.32 min (Method 2). $^1$H NMR (400 MHz, CDCl$_3$) δ ppm 8.10-8.16 (2H, m), 7.68-7.77 (3H, m), 7.62-7.67 (1H, m), 7.06-7.20 (2H, m), 6.99 (1H, d, J=7.7 Hz), 4.55 (1H, s), 4.36 (4H, br. s.), 2.41 (2H, quin, J=7.8 Hz), 1.13 (6H, d, J=1.3 Hz).

Example 85

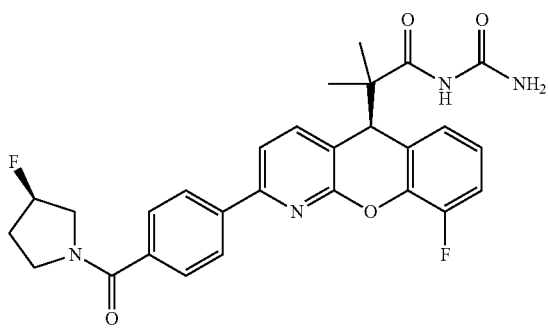 [SMILES: CC(C)(C(=O)NC(N)=O)[C@@H]1c2ccc(-c3ccc(C(=O)N4CC[C@@H](F)C4)cc3)nc2Oc2c(F)cccc21]

The title compound was prepared from Example 63 in a similar manner as the title compound of Preparation 49. MS (E+) m/z: 521.2 (M+H); LC retention time: 3.06 min. $^1$H NMR (400 MHz, CDCl$_3$) δ ppm 8.10-8.17 (2H, m), 7.58-7.76 (4H, m), 7.06-7.22 (2H, m), 6.99 (1H, d, J=7.7 Hz), 5.95 (1H, d, J=0.9 Hz), 4.55 (1H, s), 3.58-4.12 (4H, m), 1.93-2.49 (2H, m), 1.14 (6H, d, J=3.3 Hz).

BIOLOGICAL ACTIVITY DATA

The glucocorticoid receptor (GR) binding affinity (Ki) of Examples ("Ex.") 1 to 31, the accompanying AP-1 activity, and AP-1 maximum inhibition values are given in the table below. The data presented below were obtained using the assays referred to in the table and described herein in the ASSAY section supra.

| Ex. No. | GR ($K_i$, nM) (measured in GR binding Assay II) | AP-1 ($EC_{50}$, nM) (measured in cellular transrepression assay) | AP-1 Max % inhibition (measured in cellular transrepression assay) |
|---|---|---|---|
| 1 | 42.71 | 5000.00 | 17.32 |
| 2 | 5.93 | 4.97 | 67.48 |
| 3 | 93.52 | 266.80 | 79.66 |
| 4 | 7.01 | 6.65 | 67.93 |
| 5 | 66.53 | 180.30 | 32.83 |
| 6 | 12.94 | 23.71 | 42.52 |
| 7 | 8.53 | 18.40 | 53.92 |
| 8 | 3.59 | 5.97 | 64.35 |
| 9 | 8.81 | 18.30 | 46.14 |
| 10 | 170.60 | 623.20 | 66.12 |
| 11 | 4.44 | 29.60 | 46.34 |
| 12 | 5.04 | 85.71 | 36.42 |
| 13 | 13.61 | 483.30 | 31.60 |
| 14 | 37.45 | 336.80 | 54.92 |
| 15 | 1.42 | 47.07 | 61.15 |
| 16 | 1.60 | 35.14 | 49.58 |
| 17 | 9.68 | 2500.00 | 37.10 |
| 18 | 238.80 | 5000.00 | 21.96 |
| 19 | 32.41 | 199.00 | 25.94 |
| 20 | 12.17 | 135.30 | 29.26 |
| 21 | 1.42 | 21.73 | 39.92 |
| 22 | 5.69 | 8.21 | 44.77 |
| 23 | 3.64 | 224.70 | 44.63 |
| 24 | 7.45 | 243.60 | 33.10 |
| 25 | 5.26 | 346.70 | 25.41 |
| 26 | 5.28 | 5000.00 | 6.98 |
| 27 | 10.89 | 5000.00 | 16.38 |
| 28 | 1.81 | 7.63 | 68.66 |
| 29 | 3.33 | 645.90 | 51.82 |
| 30 | 0.72 | 1.59 | 63.94 |
| 31 | 0.43 | 5.55 | 56.84 |
| 32 | 3.55 | 4.89 | 59.56 |

-continued

| Ex. No. | GR ($K_i$, nM) (measured in GR binding Assay II) | AP-1 ($EC_{50}$, nM) (measured in cellular transrepression assay) | AP-1 Max % inhibition (measured in cellular transrepression assay) |
|---|---|---|---|
| 33 | 0.59 | 5.82 | 64.54 |
| 34 | 0.25 | 1.24 | 68.62 |
| 35 | 0.40 | 7.50 | 54.04 |
| 36 | 0.80 | 16.25 | 59.83 |
| 37 | 1.74 | 129.30 | 29.97 |
| 38 | 1.74 | 14.09 | 56.33 |
| 39 | 0.93 | 13.01 | 58.23 |
| 40 | 1.93 | 8.69 | 68.22 |
| 41 | 1.11 | 18.94 | 54.62 |
| 42 | 0.92 | 19.24 | 48.53 |
| 43 | 0.91 | 5.39 | 67.14 |
| 44 | 2.37 | 13.91 | 69.43 |
| 45 | 0.82 | 7.77 | 55.41 |
| 46 | 1.97 | 16.49 | 65.90 |
| 47 | 0.84 | 29.12 | 59.56 |
| 48 | 7.35 | 20.34 | 69.50 |
| 49 | 1.09 | 13.26 | 67.00 |
| 50 | 1.76 | 15.31 | 69.26 |
| 51 | 1.34 | 13.17 | 65.20 |
| 52 | 123.30 | 814.90 | 57.02 |
| 53 | 369.10 | 2500.00 | 28.67 |
| 54 | 7.65 | 67.22 | 55.36 |
| 55 | 11.92 | 116.50 | 60.59 |
| 56 | 2.95 | 6.39 | 72.50 |
| 57 | 4.23 | 128.10 | 73.98 |
| 58 | 24.86 | 72.62 | 45.16 |
| 59 | 1.66 | 19.90 | 43.00 |
| 60 | 1.13 | 2.90 | 66.44 |
| 61 | 4.26 | 31.09 | 39.15 |
| 62 | 1.15 | 8.24 | 64.75 |
| 63 | 10.81 | 141.90 | 39.61 |
| 64 | 1.70 | 72.45 | 44.43 |
| 65 | 0.50 | 4.89 | 54.73 |
| 66 | 2.66 | 39.67 | 36.83 |
| 67 | 1.51 | 4.98 | 53.28 |
| 68 | 0.63 | 8.57 | 61.39 |
| 69 | 0.32 | 2.03 | 67.09 |
| 70 | 1.19 | 8.94 | 79.50 |
| 71 | 25.86 | 93.58 | 39.16 |
| 72 | 4.71 | 35.99 | 37.36 |
| 73 | 1.72 | 20.07 | 55.78 |
| 74 | 8.57 | 5000.00 | 7.70 |
| 75 | 31.97 | 5000.00 | 10.32 |
| 76 | 119.10 | 326.90 | 23.09 |
| 77 | 61.73 | 785.70 | 55.34 |
| 78 | 87.12 | 339.80 | 46.32 |
| 79 | 20.75 | 788.90 | 36.12 |
| 80 | 25.07 | 84.61 | 44.42 |
| 81 | 1.71 | 12.76 | 42.41 |
| 82 | 0.58 | 6.69 | 60.06 |
| 83 | 1.11 | 5.89 | 86.42 |
| 84 | 0.93 | 4.22 | 67.75 |
| 85 | 1.20 | 0.80 | 76.00 |

What is claimed is:

1. A compound according to formula I,

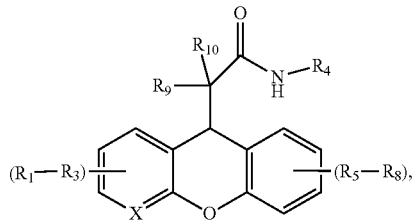

or an enantiomer, diastereomer, tautomer, or a pharmaceutically-acceptable salt thereof, wherein:

X is selected from N and $CR_1$;

$R_1$, $R_2$, $R_3$, $R_5$, $R_6$, $R_7$, and $R_8$ are the same or different and at each occurrence are independently selected from hydrogen, halogen, $C_{1-8}$alkyl, substituted $C_{1-8}$alkyl, $C_{2-8}$alkenyl, substituted $C_{2-8}$alkenyl, $C_{2-8}$alkynyl, $C_{2-8}$substituted alkynyl, nitro, cyano, dialkylaminoalkoxy, alkoxyalkyloxyalkyloxy, $C_{3-7}$cycloalkyl, $C_{3-7}$cycloalkenyl, $C_{3-7}$cycloalkynyl, heterocyclo, aryl, and heteroaryl, wherein said cycloalkyl, cycloalkenyl, heterocyclo, aryl, and heteroaryl are each substituted with zero to three halogen, $C_{1-6}$alkyl, $C_{1-6}$hydroxyalkyl, $C_{1-6}$haloalkyl, $C_{1-6}$alkoxy, $C_{1-6}$haloalkoxy, $-OR_{12}$, $=O$, $-NR_{12}R_{13}$, $-C(=O)R_{12}$, $-C(=O)OR_{12}$, $-C(=O)NR_{12}R_{13}$, $-OC(=O)NR_{12}R_{13}$, $-NR_{12}C(O)NR_{12}R_{13}$, $-OC(=O)R_{12}$, $-NR_{12}C(=O)R_{13}$, $-NR_{12}C(O)OR_{13}$, $-NR_{12}C(S)OR_{13}$, $-S(O)_pR_{14}$, $-NR_{12}SO_2R_{14}$, $SO_2NR_{12}R_{13}$, $C_{3-7}$cycloalkyl, 3- to 6-membered heterocyclo, phenyl, and 5- to 6-membered heteroaryl optionally substituted with $C_{1-3}$alkyl, $C_{1-3}$hydroxyalkyl, $C_{1-3}$haloalkyl, $C_{1-3}$alkoxy, or $C_{1-3}$haloalkoxy;

$R_4$ is $C(O)R_{11}$;

$R_9$ and $R_{10}$ are the same or different and at each occurrence are independently $C_{1-6}$alkyl; or $R_9$ and $R_{10}$ are taken together with the atom to which they are attached to form a $C_{3-7}$cycloalkyl, $C_{3-7}$cycloalkenyl, or heterocyclo group;

$R_{11}$ at each occurrence is independently selected from $C_{1-6}$alkyl, $-OR_{15}$, $-NR_{15}R_{16}$, $C_{3-7}$cycloalkyl, 3- to 6-membered heterocyclo, phenyl, and 5- to 6-membered heteroaryl optionally substituted with $C_{1-3}$alkyl, $C_{1-3}$hydroxyalkyl, $C_{1-3}$haloalkyl, $C_{1-3}$alkoxy, or $C_{1-3}$haloalkoxy;

$R_{12}$ and $R_{13}$ are the same or different and at each occurrence are independently selected from (i) hydrogen, $C_{1-8}$alkyl, substituted $C_{1-8}$alkyl, $C_{2-8}$alkenyl, substituted $C_{2-8}$alkenyl, $C_{2-8}$alkynyl, substituted $C_{2-8}$alkynyl, $C_{3-7}$cycloalkyl, $C_{3-7}$cycloalkenyl, aryl, heteroaryl, and heterocyclo; or (ii) where possible, $R_{12}$ is taken together with $R_{13}$ to form a heteroaryl or heterocyclo ring each optionally substituted with OH, oxo, $C_{1-4}$alkoxy, $C_{1-4}$alkyl, halogen, and $C_{1-4}$haloalkyl;

$R_{14}$ at each occurrence is independently selected from $C_{1-8}$alkyl, substituted $C_{1-8}$alkyl, $C_{2-8}$alkenyl, substituted $C_{2-8}$alkenyl, $C_{2-8}$alkynyl, substituted $C_{2-8}$alkynyl, $C_{3-7}$cycloalkyl, $C_{3-7}$cycloalkenyl, aryl, heteroaryl, and heterocyclo;

$R_{15}$ and $R_{16}$ are the same or different and at each occurrence are independently selected from (i) hydrogen, $C_{1-8}$alkyl, substituted $C_{1-8}$alkyl, $C_{2-8}$alkenyl, substituted $C_{2-8}$alkenyl, $C_{2-8}$alkynyl, substituted $C_{2-8}$alkynyl, $C_{3-7}$cycloalkyl, $C_{3-7}$cycloalkenyl, aryl, heteroaryl, and heterocyclo; or (ii) where possible, $R_{15}$ is taken together with $R_{16}$ to form a heteroaryl or heterocyclo ring; p is 0, 1 and 2; and provided the following compounds are excluded:

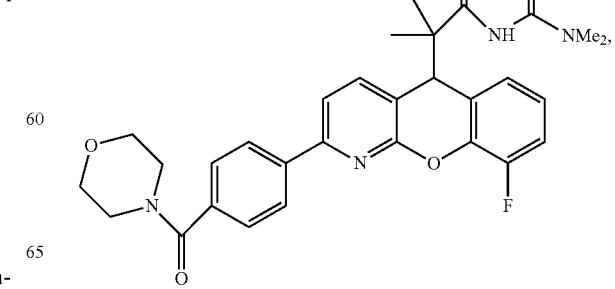

-continued

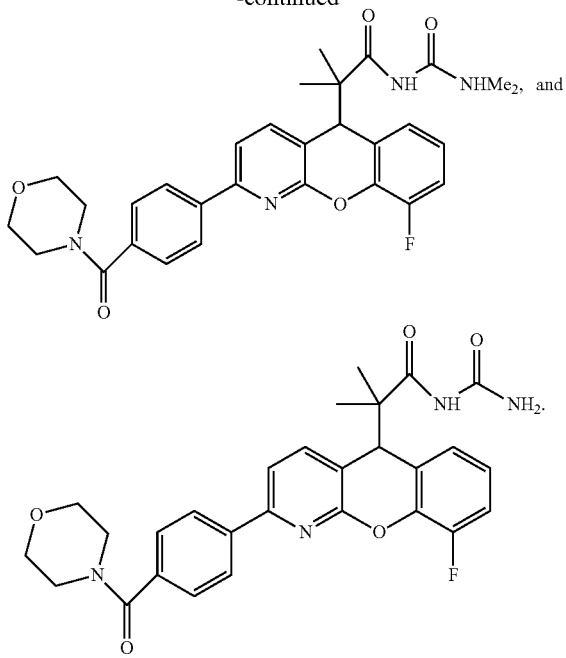

2. The compound as defined in claim 1, having formula II,

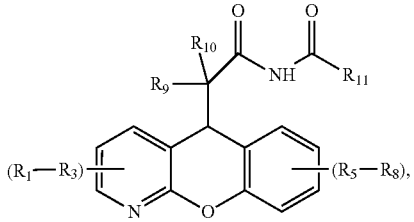

or an enantiomer, diastereomer, tautomer, or a pharmaceutically-acceptable salt thereof, wherein:

$R_1$, $R_2$, and $R_3$ are the same or different and at each occurrence are independently selected from halogen, $C_{1-8}$alkyl, cyano, $C_{3-7}$cycloalkyl, 3- to 10-membered heterocyclo, 5- to 10-membered aryl, and 5- to 10-membered heteroaryl, wherein said alkyl, alkoxy, cycloalkyl, heterocyclo, aryl, and heteroaryl are each substituted with zero to three substituents independently selected from halogen, $C_{1-6}$alkyl, $C_{1-6}$hydroxyalkyl, $C_{1-6}$haloalkyl, $C_{1-6}$alkoxy, $C_{1-6}$haloalkoxy, —$OR_{12}$, —$NR_{12}R_{13}$, —$C(=O)R_{12}$, —$C(=O)OR_{12}$, —$C(=O)NR_{12}R_{13}$, —$OC(=O)NR_{12}R_{13}$, —$NR_{12}C(O)NR_{12}R_{13}$, —$OC(=O)R_{12}$, —$NR_{12}C(=O)R_{13}$, —$NR_{12}C(O)OR_{13}$, —$NR_{12}C(S)OR_{13}$, —$S(O)_pR_{14}$, —$NR_{12}SO_2R_{14}$, $SO_2NR_{12}R_{13}$, $C_{3-7}$cycloalkyl, 3- to 6-membered heterocyclo, phenyl, and 5- to 6-membered heteroaryl optionally substituted with $C_{1-3}$alkyl, $C_{1-3}$hydroxyalkyl, $C_{1-3}$haloalkyl, $C_{1-3}$alkoxy, or $C_{1-3}$haloalkoxy;

$R_5$, $R_6$, $R_7$, and $R_8$ are the same or different and at each occurrence are independently selected from hydrogen, halogen, and $C_{1-6}$alkyl;

$R_{11}$ at each occurrence is independently selected from $C_{1-6}$alkyl, —$NR_{15}R_{16}$, $C_{3-7}$cycloalkyl, and 3- to 6-membered heterocycle;

$R_{12}$ and $R_{13}$ are the same or different and at each occurrence are independently selected from (i) hydrogen, $C_{1-6}$alkyl, $C_{1-6}$hydroxyalkyl, $C_{1-6}$haloalkyl, $C_{1-6}$alkoxy, $C_{1-6}$haloalkoxy, $C_{3-7}$cycloalkyl, phenyl, 5- to 6-membered heteroaryl, and 5- to 6-membered heterocyclo; or (ii) where possible, $R_{12}$ is taken together with $R_{13}$ to form a 5- to 6-membered heteroaryl or 4- to 6-membered heterocyclo ring optionally substituted with OH, oxo, $C_{1-4}$alkoxy, $C_{1-4}$alkyl, halogen, and $C_{1-4}$haloalkyl;

$R_{14}$ at each occurrence is independently selected from $C_{1-6}$alkyl, $C_{1-6}$hydroxyalkyl, $C_{1-6}$haloalkyl, $C_{1-6}$alkoxy, $C_{1-6}$haloalkoxy, $C_{3-7}$cycloalkyl, phenyl, 5- to 6-membered heteroaryl, and 5- to 6-membered heterocycle; and $R_{15}$, and $R_{16}$ are the same or different and at each occurrence are independently selected from (i) hydrogen, $C_{1-8}$alkyl, substituted $C_{1-8}$alkyl, $C_{2-8}$alkenyl, substituted $C_{2-8}$alkenyl, $C_{2-8}$alkynyl, substituted $C_{2-8}$alkynyl, $C_{3-7}$cycloalkyl, $C_{3-7}$cycloalkenyl, aryl, heteroaryl, and heterocyclo; or (ii) where possible, $R_{15}$ is taken together with $R_{16}$ to form a heteroaryl or heterocyclo ring.

3. The compound as defined in claim 2 having the following formula III,

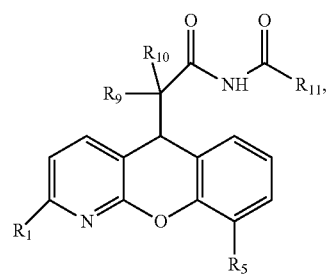

or an enantiomer, diastereomer, tautomer, or a pharmaceutically-acceptable salt thereof, wherein:

$R_1$ is independently selected from 5- to 10-membered aryl and 5- to 10-membered heteroaryl, wherein said aryl and heteroaryl group are each substituted with zero to three substituents independently selected from halogen, $C_{1-6}$hydroxyalkyl, —$OR_{12}$, —$NR_{12}R_{13}$, —$C(=O)R_{12}$, —$C(=O)OR_{12}$, —$C(=O)NR_{12}R_{13}$, —$NR_{12}C(=O)R_{13}$, —$S(O)_2R_{14}$, —$NR_{12}SO_2R_{14}$, phenyl, and 5- to 6-membered heteroaryl optionally substituted with $C_{1-3}$alkyl;

$R_5$ is independently selected from is hydrogen and halogen;

$R_9$ and $R_{10}$ are $C_{1-3}$alkyl;

$R_{12}$ and $R_{13}$ are the same or different and at each occurrence are independently selected from (i) hydrogen, $C_{1-6}$alkyl, $C_{1-6}$haloalkyl, and 5- to 6-membered heterocyclo; or (ii) where possible, $R_{12}$ is taken together with $R_{13}$ to form a 4- to 6-membered heterocyclo ring optionally substituted with $C_{1-3}$alkyl and oxo; and $R_{14}$ at each occurrence is independently $C_{1-6}$alkyl.

4. The compound as defined in claim 3, or an enantiomer, diastereomer, tautomer, or a pharmaceutically-acceptable salt thereof, wherein:

$R_{11}$ at each occurrence is independently selected from $C_{1-6}$alkyl, $C_{3-7}$cycloalkyl, and —$NR_{15}R_{16}$; and $R_{15}$, and $R_{16}$ are the same or different and at each occurrence are independently selected from (i) hydrogen, $C_{1-8}$alkyl, substituted $C_{1-8}$alkyl wherein the substituent is selected from OH and aryl optionally substitute with $C_{1-4}$alkoxy, $C_{3-7}$cycloalkyl, $C_{3-7}$cycloalkenyl, aryl, heteroaryl, and heterocyclo; or (ii) where possible, $R_{15}$ is taken together with $R_{16}$ to form a heteroaryl or heterocyclo ring.

5. A compound as defined in claim 4, or an enantiomer, diastereomer, tautomer, or a pharmaceutically-acceptable salt thereof, wherein:

$R_1$ is phenyl, pyridyl or pyrimidinyl, each of which is substituted with zero to three substituents independently selected from halogen, $C_{1-6}$hydroxyalkyl, —$OR_{12}$, —$NR_{12}R_{13}$, —C(=O)$R_{12}$, —C(=O)$OR_{12}$, —C(=O)$NR_{12}R_{13}$, —$NR_{12}$C(=O)$R_{13}$, —S(O)$_2R_{14}$, —$NR_{12}SO_2R_{14}$, and 5- to 6-membered heteroaryl substituted with $C_{1-3}$alkyl group.

6. The compound as defined in claim 5, or an enantiomer, diastereomer, tautomer, or a pharmaceutically-acceptable salt thereof, wherein:

$R_1$ is phenyl, pyridyl or pyrimidinyl, each of which is substituted with zero to three substituents independently selected from F, Cl, —$OCF_3$, —$NH_2$,

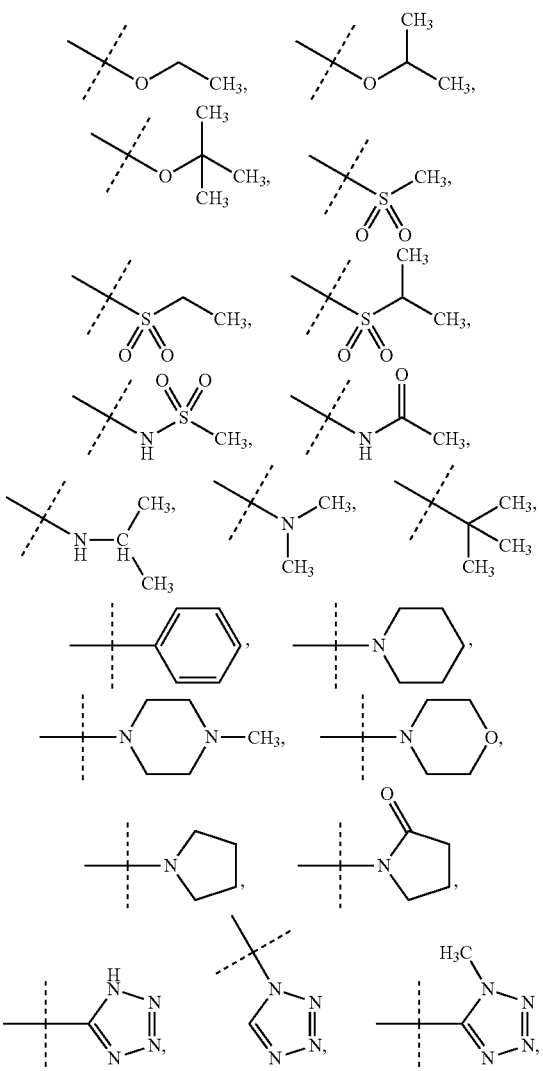

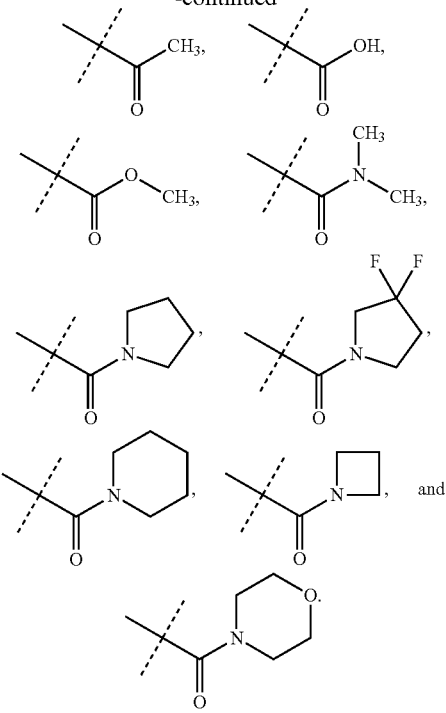

7. The compound as defined in claim 3 or an enantiomer, diastereomer, tautomer, or a pharmaceutically-acceptable salt thereof, wherein:

$R_1$ is phenyl, pyridyl or pyrimidinyl, each of which is substituted with zero to three substituents independently selected from halogen, $C_{1-6}$hydroxyalkyl, —$OR_{12}$, —$NR_{12}R_{13}$, —C(=O)$R_{12}$, —C(=O)$OR_{12}$, —C(=O)$NR_{12}R_{13}$, —$NR_{12}$C(=O)$R_{13}$, —S(O)$_2R_{14}$, —$NR_{12}SO_2R_{14}$, and 5- to 6-membered heteroaryl substituted with $C_{1-3}$alkyl; and $R_{11}$ at each occurrence is independently selected from $C_{1-6}$alkyl, and $C_{3-7}$cycloalkyl.

8. The compound as defined in claim 3, or an enantiomer, diastereomer, tautomer, or a pharmaceutically-acceptable salt thereof, wherein:

$R_1$ is phenyl, pyridyl or pyrimidinyl, each of which is substituted with zero to three substituents independently selected from halogen, $C_{1-6}$hydroxyalkyl, —$OR_{12}$, —$NR_{12}R_{13}$, —C(=O)$R_{12}$, —C(=O)$OR_{12}$, —C(=O)$NR_{12}R_{13}$, —$NR_{12}$C(=O)$R_{13}$, —S(O)$_2R_{14}$, —$NR_{12}SO_2R_{14}$, and 5- to 6-membered heteroaryl substituted with $C_{1-3}$alkyl;

$R_{11}$ at each occurrence is independently selected from —$NR_{15}R_{16}$ and 3- to 6-membered heterocycle; and $R_{15}$, and $R_{16}$ are the same or different and at each occurrence are independently selected from (i) hydrogen, $C_{1-8}$alkyl, substituted $C_{1-8}$alkyl wherein the substituent is selected from OH and aryl optionally substitute with $C_{1-4}$alkoxy, $C_{3-7}$cycloalkyl, $C_{3-7}$cycloalkenyl, aryl, heteroaryl, and heterocyclo; or (ii) where possible, $R_{15}$ is taken together with $R_{16}$ to form a heteroaryl or heterocyclo ring.

9. The compound as defined in claim 8, having formula IV,

IV

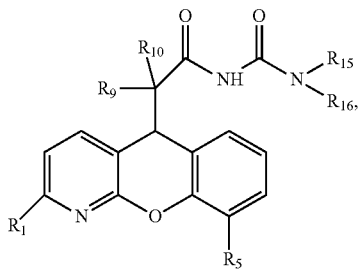

or an enantiomer, diastereomer, tautomer, or a pharmaceutically-acceptable salt thereof, wherein:

$R_1$ is phenyl, pyridyl or pyrimidinyl, each of which is substituted with zero to three substituents independently selected from F, Cl, —OCF$_3$, —NH$_2$,

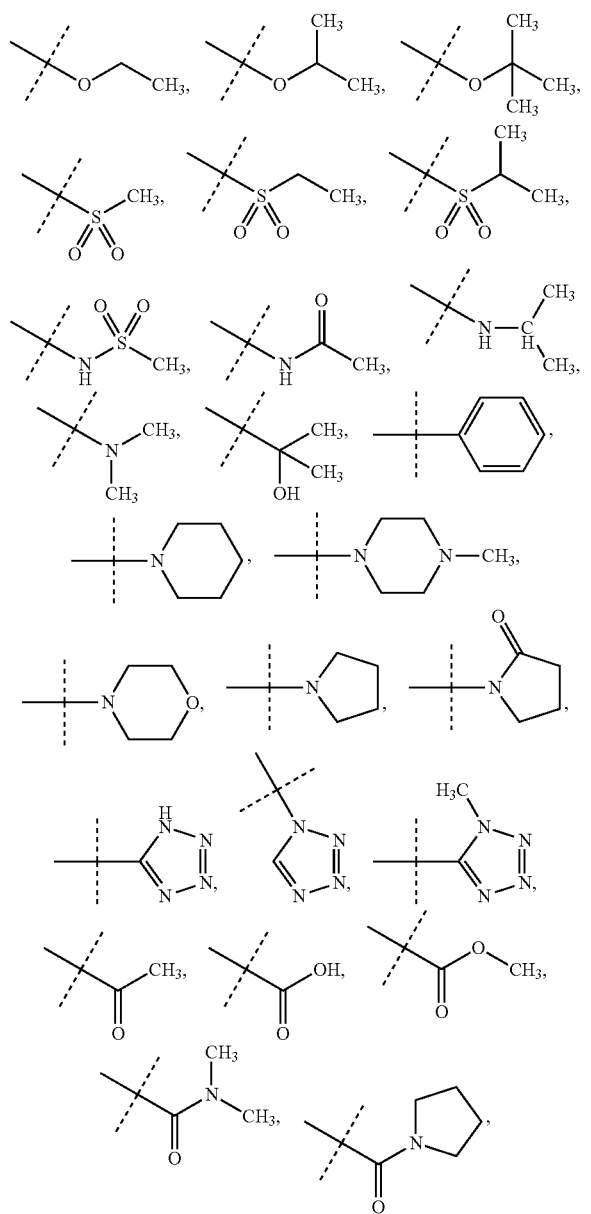

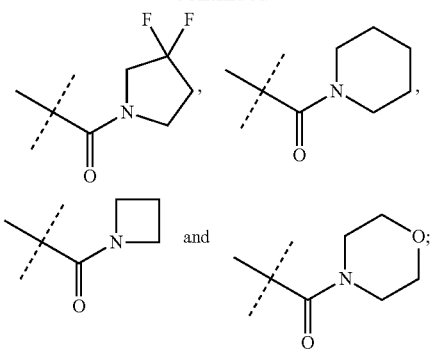

$R_5$ is independently selected from hydrogen and halogen;

$R_9$ and $R_{10}$ are $C_{1-3}$alkyl; and $R_{15}$ and $R_{16}$ are the same or different and at each occurrence are independently selected from (i) hydrogen, methyl, ethyl, propyl, butyl, $C_{1-3}$alkyl substituted with OH or phenyl optionally substitute with methoxy, cyclopropyl, cyclobutyl, cyclopentyl, cyclohexyl, phenyl, and heteroaryl; or (ii) where possible, $R_{15}$ is taken together with $R_{16}$ to form

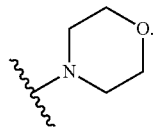 [SMILES: *N1CCOCC1]

10. The compound as defined in claim 9, wherein:

$R_1$ is

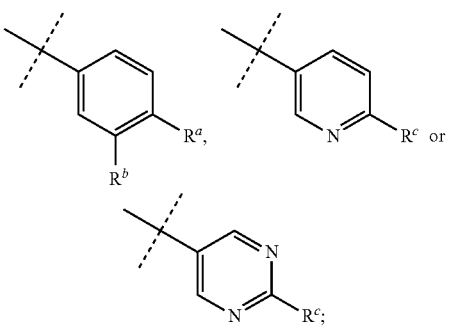

$R^a$ is H, —OCF$_3$, —NH$_2$,

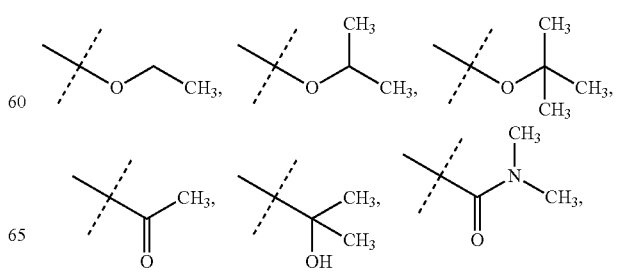

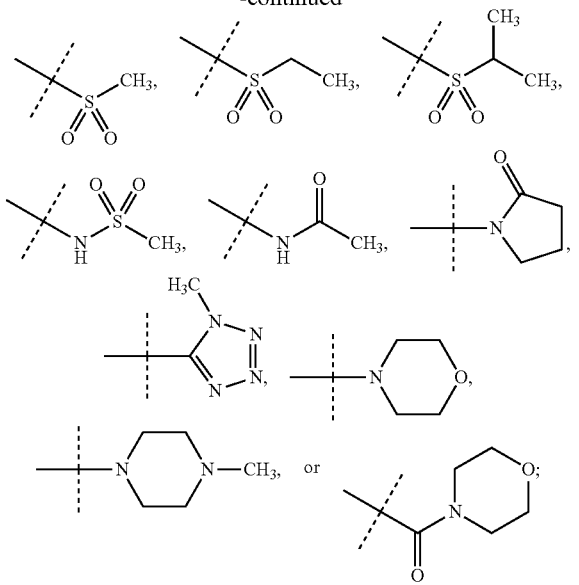

$R^b$ is H, F, or Cl; and
$R^c$ is H, F,

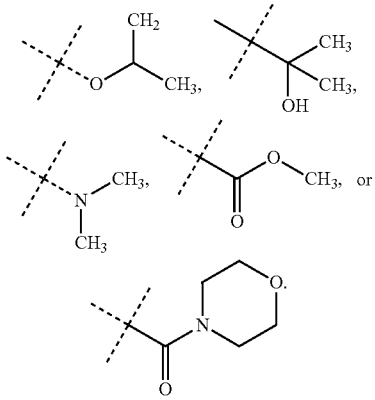

11. The compound as defined in claim 1, having formula V,

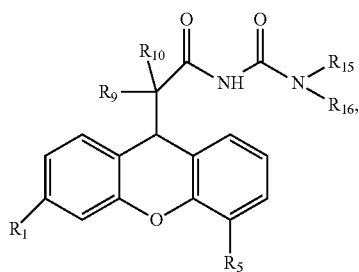

or an enantiomer, diastereomer, tautomer, or a pharmaceutically-acceptable salt thereof, wherein:
$R_1$ at each occurrence are independently selected from hydrogen, halogen, $C_{1-8}$alkyl, substituted $C_{1-8}$alkyl, $C_{2-8}$alkenyl, substituted $C_{2-8}$alkenyl, $C_{2-8}$alkynyl, $C_{2-8}$substituted alkynyl, nitro, cyano, dialkylamino-alkoxy, alkoxyalkyloxyalkyloxy, $C_{3-7}$cycloalkyl, $C_{3-7}$cycloalkenyl, $C_{3-7}$cycloalkynyl, heterocyclo, aryl, and heteroaryl, wherein said cycloalkyl, cycloalkenyl, heterocyclo, aryl, and heteroaryl are each substituted with zero to three halogen, $C_{1-6}$alkyl, $C_{1-6}$hydroxyalkyl, $C_{1-6}$haloalkyl, $C_{1-6}$alkoxy, $C_{1-6}$haloalkoxy, —$OR_{12}$, =O, —$NR_{12}R_{13}$, —C(=O)$R_{12}$, —C(=O)$OR_{12}$, —C(=O)$NR_{12}R_{13}$, —OC(=O)$NR_{12}R_{13}$, —$NR_{12}$C(O)$NR_{12}R_{13}$, —OC(=O)$R_{12}$, —$NR_{12}$C(=O)$R_{13}$, —$NR_{12}$C(O)$OR_{13}$, —$NR_{12}$C(S)$OR_{13}$, —S(O)$_p R_{14}$, —$NR_{12}SO_2 R_{14}$, $SO_2 NR_{12} R_{13}$, $C_{3-7}$cycloalkyl, 3- to 6-membered heterocyclo, phenyl, and 5- to 6-membered heteroaryl optionally substituted with $C_{1-3}$alkyl, $C_{1-3}$hydroxyalkyl, $C_{1-3}$haloalkyl, $C_{1-3}$alkoxy, or $C_{1-3}$haloalkoxy;
$R_9$ and $R_{10}$ are the same or different and at each occurrence are independently $C_{1-6}$alkyl; or
$R_9$ and $R_{10}$ are taken together with the atom to which they are attached to form a $C_{3-7}$cycloalkyl, $C_{3-7}$cycloalkenyl, or heterocyclo group;
$R_{12}$ and $R_{13}$ are the same or different and at each occurrence are independently selected from (i) hydrogen, $C_{1-8}$alkyl, substituted $C_{1-8}$alkyl, $C_{2-8}$alkenyl, substituted $C_{2-8}$alkenyl, $C_{2-8}$alkynyl, substituted $C_{2-8}$alkynyl, $C_{3-7}$cycloalkyl, $C_{3-7}$cycloalkenyl, aryl, heteroaryl, and heterocyclo; or (ii) where possible, $R_{12}$ is taken together with $R_{13}$ to form a heteroaryl or heterocyclo ring each optionally substituted with OH, oxo, $C_{1-4}$alkoxy, $C_{1-4}$alkyl, halogen, and $C_{1-4}$haloalkyl;
$R_{14}$ at each occurrence is independently selected from $C_{1-8}$alkyl, substituted $C_{1-8}$alkyl, $C_{2-8}$alkenyl, substituted $C_{2-8}$alkenyl, $C_{2-8}$alkynyl, substituted $C_{2-8}$alkynyl, $C_{3-7}$cycloalkyl, $C_{3-7}$cycloalkenyl, aryl, heteroaryl, and heterocyclo;
$R_{15}$ and $R_{16}$ are the same or different and at each occurrence are independently selected from (i) hydrogen, $C_{1-8}$alkyl, substituted $C_{1-8}$alkyl, $C_{2-8}$alkenyl, substituted $C_{2-8}$alkenyl, $C_{2-8}$alkynyl, substituted $C_{2-8}$alkynyl, $C_{3-7}$cycloalkyl, $C_{3-7}$cycloalkenyl, aryl, heteroaryl, and heterocyclo; or (ii) where possible, $R_{15}$ is taken together with $R_{16}$ to form a heteroaryl or heterocyclo ring; p is 0, 1 and 2.

12. A pharmaceutical composition comprising a compound as defined in claim 1 and a pharmaceutically acceptable carrier therefor.

13. A method of reduction or amelioration, partial or complete, of a disease or disorder selected from an endocrine disorder, rheumatic disorder, collagen disease, dermatologic disease, allergic disease, ophthalmic disease, respiratory disease, hematologic disease, gastrointestinal disease, inflammatory disease, immune disease, neoplastic disease and metabolic disease, which comprise administering to a patient in need of treatment, a therapeutically effective amount of a compound as defined in claim 1.

14. The method as defined in claim 13 wherein the disease or disorder is an inflammatory or autoimmune disease selected from transplant rejection of kidney, liver, heart, lung, pancreas, bone marrow, cornea, small bowel, skin allografts, skin homografts, heart valve xenograft, serum sickness, and graft vs. host disease, rheumatoid arthritis, psoriatic arthritis, multiple sclerosis, asthma, inflammatory bowel disease, Crohn's disease, ulcerative colitis, pyoderma gangrenum, systemic lupus erythematosis, myasthenia gravis, psoriasis, dermatitis, dermatomyositis; eczema, seborrhoea, pulmonary inflammation, eye uveitis, hepatitis, Graves' disease, Hashimoto's thyroiditis, autoimmune thyroiditis, Behcet's or Sjögren's syndrome, pernicious or immunohaemolytic anemia, atherosclerosis, Addison's disease, idiopathic adrenal insufficiency, autoimmune polyglandular disease, glomerulonephritis, scleroderma, morphea, lichen planus, vitiligo, alopecia areata, autoimmune alopecia, autoimmune hypopituitarism, Guillain-Barre syndrome, and alveolitis; contact hypersensitivity, delayed-type hypersensitivity, contact dermatitis, urticaria, skin allergies, respiratory allergies, hay fever, allergic rhinitis and gluten-sensitive enteropathy, osteoarthritis, acute pancreatitis, chronic pancreatitis, acute respiratory distress syndrome, Sezary's syndrome, restenosis, stenosis and atherosclerosis, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetitformis, severe erythema multiforme, exfoliative dermatitis, psoriasis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, ulcerative colitis, regional enteritis, Crohn's disease, Sjögren's syndrome, autoimmune vasculitis, multiple sclerosis, myasthenia gravis, sepsis, and chronic obstructive pulmonary disease.

15. The method as defined in claim 14 wherein the disease or disorder is selected from transplant rejection, rheumatoid arthritis, psoriatic arthritis, multiple sclerosis, asthma, inflammatory bowel disease, systemic lupus, erythematosis, and psoriasis.

* * * * *